(12) United States Patent
Gustine et al.

(10) Patent No.: US 8,992,579 B1
(45) Date of Patent: Mar. 31, 2015

(54) LATERAL FIXATION CONSTRUCTS AND RELATED METHODS

(75) Inventors: Seth Gustine, Encinitas, CA (US); Spencer Pettine, San Diego, CA (US); Kade T. Huntsman, Salt Lake City, UT (US)

(73) Assignee: NuVasive, Inc., San Diego, CA (US)

( * ) Notice: Subject to any disclaimer, the term of this patent is extended or adjusted under 35 U.S.C. 154(b) by 94 days.

(21) Appl. No.: 13/415,769

(22) Filed: Mar. 8, 2012

Related U.S. Application Data

(60) Provisional application No. 61/450,595, filed on Mar. 8, 2011.

(51) Int. Cl.
*A61B 17/70* (2006.01)

(52) U.S. Cl.
CPC .................. *A61B 17/7062* (2013.01)
USPC ....................................................... 606/278

(58) Field of Classification Search
USPC ............. 606/246–278, 53–59; 403/167, 169, 403/174–175, 177, 186
See application file for complete search history.

(56) References Cited

U.S. PATENT DOCUMENTS

| | | | |
|---|---|---|---|
| 3,196,876 A | 7/1965 | Miller | |
| 3,741,205 A | 6/1973 | Markolf | |
| 3,788,318 A | 1/1974 | Kim | |
| 3,997,138 A * | 12/1976 | Crock et al. | 248/67.5 |
| 4,047,524 A | 9/1977 | Hall | |
| 4,289,123 A | 9/1981 | Dunn | |
| 4,545,374 A | 10/1985 | Jacobson | |
| 4,611,581 A | 9/1986 | Steffee | |
| 4,620,533 A * | 11/1986 | Mears | 606/54 |
| 4,648,388 A | 3/1987 | Steffee | |
| 4,653,481 A * | 3/1987 | Howland et al. | 606/261 |
| 4,773,402 A | 9/1988 | Asher | |
| 5,024,213 A | 6/1991 | Asher | |
| 5,074,864 A | 12/1991 | Cozad | |
| 5,085,660 A | 2/1992 | Lin | |
| 5,108,395 A | 4/1992 | Laurain | |
| 5,129,899 A | 7/1992 | Small | |
| 5,137,509 A | 8/1992 | Freitas | |
| 5,147,360 A * | 9/1992 | Dubousset | 606/250 |
| 5,147,361 A | 9/1992 | Ojima | |
| 5,152,303 A | 10/1992 | Allen | |
| 5,158,543 A | 10/1992 | Lazarus | |
| 5,242,427 A | 9/1993 | Bilweis | |
| 5,261,909 A | 11/1993 | Sutterlin | |
| 5,306,275 A | 4/1994 | Bryan | |
| 5,324,290 A | 6/1994 | Zdeblick | |
| 5,330,473 A * | 7/1994 | Howland | 606/250 |
| 5,364,399 A | 11/1994 | Lowery | |
| 5,368,594 A * | 11/1994 | Martin et al. | 606/252 |

(Continued)

FOREIGN PATENT DOCUMENTS

| CN | 2162921 | 4/1994 |
|---|---|---|
| CN | 202342145 | 7/2012 |

(Continued)

*Primary Examiner* — Mary Hoffman
*Assistant Examiner* — M. C. E.
(74) *Attorney, Agent, or Firm* — Jonathan Spangler; Rory Schermerhorn

(57) ABSTRACT

This disclosure describes a several examples of a surgical fixation system including a plurality of anchor assemblies connected by one or more spinal rods. The anchor assemblies include a staple, bone anchor, staple cap, and lock nut. The surgical fixation system is configured for implantation on a lateral aspect of the spine.

12 Claims, 33 Drawing Sheets

(56) References Cited

U.S. PATENT DOCUMENTS

| | | | | |
|---|---|---|---|---|
| 5,380,323 | A | 1/1995 | Howland | |
| 5,380,324 | A | 1/1995 | Muller | |
| 5,380,325 | A | 1/1995 | Lahille | |
| 5,401,247 | A | 3/1995 | Yoon | |
| 5,445,617 | A | 8/1995 | Yoon | |
| 5,476,467 | A | 12/1995 | Benoist | |
| 5,520,690 | A | 5/1996 | Errico | |
| 5,549,608 | A | 8/1996 | Errico | |
| 5,569,289 | A | 10/1996 | Yoon | |
| 5,573,511 | A | 11/1996 | Yoon | |
| 5,603,714 | A | 2/1997 | Kaneda | |
| 5,613,968 | A * | 3/1997 | Lin | 606/320 |
| 5,620,443 | A * | 4/1997 | Gertzbein et al. | 606/252 |
| 5,662,652 | A * | 9/1997 | Schafer et al. | 606/261 |
| 5,662,653 | A * | 9/1997 | Songer et al. | 606/270 |
| 5,665,072 | A | 9/1997 | Yoon | |
| 5,667,509 | A | 9/1997 | Westin | |
| 5,672,176 | A | 9/1997 | Harms et al. | |
| 5,681,312 | A | 10/1997 | Yuan | |
| 5,690,629 | A | 11/1997 | Asher | |
| 5,697,947 | A | 12/1997 | Wolf | |
| 5,702,395 | A * | 12/1997 | Hopf | 606/250 |
| 5,704,936 | A | 1/1998 | Mazel | |
| 5,713,898 | A * | 2/1998 | Stucker et al. | 606/60 |
| 5,713,900 | A | 2/1998 | Benzel | |
| 5,728,127 | A | 3/1998 | Asher | |
| 5,766,254 | A | 6/1998 | Gelbard | |
| 5,772,678 | A | 6/1998 | Thomason | |
| 5,800,435 | A | 9/1998 | Errico | |
| 5,842,478 | A | 12/1998 | Benderev | |
| 5,882,350 | A | 3/1999 | Ralph | |
| 5,899,902 | A | 5/1999 | Brown | |
| 5,899,904 | A | 5/1999 | Errico | |
| 5,899,905 | A | 5/1999 | Errico | |
| 5,925,047 | A | 7/1999 | Errico | |
| 5,928,233 | A | 7/1999 | Apfelbaum | |
| 5,928,243 | A | 7/1999 | Guyer | |
| 5,947,969 | A | 9/1999 | Errico | |
| 5,976,135 | A | 11/1999 | Sherman | |
| 5,976,146 | A | 11/1999 | Ogawa | |
| 6,004,322 | A | 12/1999 | Bernstein | |
| 6,033,420 | A | 3/2000 | Hahnen | |
| 6,063,090 | A | 5/2000 | Schlapfer | |
| 6,066,140 | A * | 5/2000 | Gertzbein et al. | 606/250 |
| 6,083,224 | A * | 7/2000 | Gertzbein et al. | 606/250 |
| 6,090,110 | A | 7/2000 | Metz-Stavenhagen | |
| 6,117,135 | A | 9/2000 | Schläpfer | |
| 6,123,706 | A * | 9/2000 | Lange | 606/264 |
| 6,126,660 | A | 10/2000 | Dietz | |
| 6,126,691 | A | 10/2000 | Kasra | |
| 6,132,431 | A | 10/2000 | Nilsson | |
| 6,136,000 | A * | 10/2000 | Louis et al. | 606/250 |
| 6,136,002 | A * | 10/2000 | Shih et al. | 606/250 |
| 6,152,927 | A | 11/2000 | Farris | |
| 6,176,861 | B1 | 1/2001 | Bernstein | |
| 6,179,838 | B1 * | 1/2001 | Fiz | 606/278 |
| 6,187,005 | B1 | 2/2001 | Brace | |
| 6,206,879 | B1 * | 3/2001 | Marnay et al. | 606/53 |
| 6,214,006 | B1 | 4/2001 | Metz-Stavenhagen | |
| 6,224,602 | B1 | 5/2001 | Hayes | |
| 6,234,705 | B1 | 5/2001 | Troxell | |
| 6,254,603 | B1 * | 7/2001 | Gertzbein et al. | 606/250 |
| 6,261,265 | B1 | 7/2001 | Mosseri | |
| 6,261,288 | B1 | 7/2001 | Jackson | |
| 6,280,445 | B1 | 8/2001 | Johnson et al. | |
| 6,283,967 | B1 | 9/2001 | Kumar et al. | |
| 6,287,308 | B1 | 9/2001 | Drewry et al. | |
| 6,296,643 | B1 * | 10/2001 | Hopf et al. | 606/263 |
| 6,299,613 | B1 * | 10/2001 | Ogilvie et al. | 606/279 |
| 6,379,357 | B1 | 4/2002 | Bernstein | |
| 6,395,007 | B1 | 5/2002 | Bhatnagar | |
| 6,416,515 | B1 | 7/2002 | Wagner | |
| 6,447,483 | B1 | 9/2002 | Steube | |
| 6,471,704 | B2 * | 10/2002 | Gertzbein et al. | 606/250 |
| 6,471,706 | B1 | 10/2002 | Schumacher | |
| 6,482,207 | B1 | 11/2002 | Errico | |
| 6,488,682 | B2 | 12/2002 | Kikuchi | |
| 6,524,311 | B2 * | 2/2003 | Gaines, Jr. | 606/278 |
| 6,524,315 | B1 | 2/2003 | Selvitelli | |
| 6,533,786 | B1 | 3/2003 | Needham | |
| 6,533,787 | B1 | 3/2003 | Lenke | |
| 6,537,276 | B2 | 3/2003 | Metz-Stavenhagen | |
| 6,551,320 | B2 | 4/2003 | Lieberman | |
| 6,565,569 | B1 * | 5/2003 | Assaker et al. | 606/250 |
| 6,569,164 | B1 * | 5/2003 | Assaker et al. | 606/250 |
| 6,572,622 | B1 * | 6/2003 | Schafer et al. | 606/272 |
| 6,576,016 | B1 | 6/2003 | Hochshuler | |
| 6,585,740 | B2 | 7/2003 | Schläpfer | |
| 6,602,254 | B2 * | 8/2003 | Gertzbein et al. | 606/250 |
| 6,616,669 | B2 * | 9/2003 | Ogilvie et al. | 606/279 |
| 6,623,484 | B2 | 9/2003 | Betz | |
| 6,626,906 | B1 * | 9/2003 | Young | 606/278 |
| 6,641,564 | B1 | 11/2003 | Kraus | |
| 6,641,614 | B1 | 11/2003 | Wagner | |
| 6,645,207 | B2 | 11/2003 | Dixon | |
| 6,652,525 | B1 | 11/2003 | Assaker | |
| 6,656,179 | B1 * | 12/2003 | Schaefer et al. | 606/267 |
| 6,663,631 | B2 | 12/2003 | Kuntz | |
| 6,669,700 | B1 | 12/2003 | Farris | |
| 6,702,817 | B2 * | 3/2004 | Beger et al. | 606/86 B |
| 6,706,044 | B2 | 3/2004 | Kuslich | |
| 6,746,450 | B1 | 6/2004 | Wall | |
| 6,749,612 | B1 * | 6/2004 | Conchy et al. | 606/250 |
| 6,755,839 | B2 | 6/2004 | Van Hoeck | |
| 6,780,186 | B2 | 8/2004 | Errico | |
| 6,786,875 | B2 | 9/2004 | Barker | |
| 6,858,029 | B2 | 2/2005 | Yeh | |
| 6,872,209 | B2 * | 3/2005 | Morrison | 606/278 |
| 6,881,215 | B2 * | 4/2005 | Assaker et al. | 606/250 |
| 6,899,714 | B2 | 5/2005 | Vaughan | |
| 6,902,565 | B2 | 6/2005 | Berger | |
| 6,916,319 | B2 * | 7/2005 | Munting | 606/278 |
| 6,916,320 | B2 | 7/2005 | Michelson | |
| 6,945,972 | B2 | 9/2005 | Frigg | |
| 6,945,975 | B2 | 9/2005 | Dalton | |
| 6,960,212 | B2 * | 11/2005 | Richelsoph et al. | 403/342 |
| 6,969,390 | B2 | 11/2005 | Michelson | |
| 6,979,334 | B2 | 12/2005 | Dalton | |
| 7,001,387 | B2 | 2/2006 | Farris | |
| 7,001,396 | B2 | 2/2006 | Glazier | |
| 7,008,423 | B2 * | 3/2006 | Assaker et al. | 606/250 |
| 7,022,085 | B2 | 4/2006 | Cooke | |
| 7,094,238 | B2 | 8/2006 | Morrison | |
| 7,115,129 | B2 | 10/2006 | Heggeness | |
| 7,137,984 | B2 | 11/2006 | Michelson | |
| 7,166,108 | B2 * | 1/2007 | Mazda et al. | 606/305 |
| 7,172,600 | B2 * | 2/2007 | Beger et al. | 606/104 |
| 7,172,612 | B2 | 2/2007 | Ishikawa | |
| 7,186,255 | B2 | 3/2007 | Baynham | |
| 7,241,074 | B2 * | 7/2007 | Thomke et al. | 403/385 |
| 7,250,054 | B2 | 7/2007 | Allen | |
| 7,252,670 | B2 | 8/2007 | Morrison | |
| 7,255,699 | B2 | 8/2007 | Paul | |
| 7,291,151 | B2 | 11/2007 | Alvarez | |
| 7,311,712 | B2 | 12/2007 | Dalton | |
| 7,344,537 | B1 * | 3/2008 | Mueller | 606/278 |
| 7,377,923 | B2 | 5/2008 | Purcell | |
| 7,455,684 | B2 * | 11/2008 | Gradel et al. | 606/246 |
| 7,491,205 | B1 | 2/2009 | Michelson | |
| 7,507,248 | B2 | 3/2009 | Beaurain | |
| 7,559,929 | B2 | 7/2009 | Denti | |
| 7,572,277 | B2 * | 8/2009 | Roussouly et al. | 606/265 |
| 7,585,299 | B2 * | 9/2009 | Rezach | 606/60 |
| 7,601,167 | B2 | 10/2009 | Lieberman | |
| 7,618,430 | B2 | 11/2009 | Scheib | |
| 7,621,914 | B2 | 11/2009 | Ralph | |
| 7,637,952 | B2 | 12/2009 | Landry | |
| 7,641,701 | B2 | 1/2010 | Kirschman | |
| 7,643,884 | B2 | 1/2010 | Pond, Jr. | |
| 7,651,497 | B2 | 1/2010 | Michelson | |
| 7,658,739 | B2 | 2/2010 | Shluzas | |
| 7,658,754 | B2 | 2/2010 | Zhang | |
| 7,662,185 | B2 | 2/2010 | Alfaro | |
| 7,666,185 | B2 | 2/2010 | Ryan | |

(56) References Cited

U.S. PATENT DOCUMENTS

| | | | |
|---|---|---|---|
| 7,678,113 B2 | 3/2010 | Melkent | |
| 7,682,392 B2 | 3/2010 | Serhan | |
| 7,699,874 B2 | 4/2010 | Young | |
| 7,699,876 B2 | 4/2010 | Barry | |
| 7,704,270 B2 | 4/2010 | de Coninck | |
| 7,704,271 B2 | 4/2010 | Abdou | |
| 7,717,938 B2 | 5/2010 | Kim | |
| 7,722,645 B2* | 5/2010 | Bryan | 606/246 |
| 7,731,734 B2* | 6/2010 | Clement et al. | 606/246 |
| 7,740,633 B2 | 6/2010 | Assell | |
| 7,744,635 B2* | 6/2010 | Sweeney et al. | 606/264 |
| 7,763,051 B2 | 7/2010 | Labrom | |
| 7,763,054 B2* | 7/2010 | Clement et al. | 606/265 |
| 7,789,895 B2* | 9/2010 | Heinz | 606/246 |
| 7,789,897 B2* | 9/2010 | Sanders | 606/278 |
| 7,789,900 B2 | 9/2010 | Levy | |
| 7,803,174 B2* | 9/2010 | Denis et al. | 606/250 |
| 7,806,912 B2* | 10/2010 | Lawton et al. | 606/250 |
| 7,842,038 B2 | 11/2010 | Haddock | |
| 7,862,593 B2* | 1/2011 | Clement et al. | 606/260 |
| D633,208 S * | 2/2011 | Murner | D24/155 |
| 7,883,510 B2 | 2/2011 | Kim | |
| 7,883,531 B2 | 2/2011 | de Coninck | |
| 7,892,260 B2 | 2/2011 | Mahoney | |
| 7,942,902 B2* | 5/2011 | Schwab | 606/250 |
| 7,942,907 B2* | 5/2011 | Richelsoph | 606/257 |
| 7,959,654 B2* | 6/2011 | Mazda et al. | 606/263 |
| RE42,545 E | 7/2011 | Ralph | |
| 7,988,691 B2 | 8/2011 | Schulze | |
| 7,993,380 B2 | 8/2011 | Hawkes | |
| 8,007,520 B2 | 8/2011 | Metz-Stavenhagen | |
| 8,029,546 B2* | 10/2011 | Capote et al. | 606/257 |
| 8,034,082 B2* | 10/2011 | Lee et al. | 606/250 |
| 8,034,085 B2* | 10/2011 | Slivka et al. | 606/266 |
| 8,052,725 B2* | 11/2011 | Biedermann et al. | 606/265 |
| 8,083,778 B2* | 12/2011 | Clement et al. | 606/267 |
| 8,123,749 B2 | 2/2012 | Serhan | |
| 8,131,346 B2 | 3/2012 | Chesbrough | |
| 8,133,283 B2 | 3/2012 | Wilson | |
| 8,147,527 B2 | 4/2012 | Hoffman | |
| 8,162,988 B2* | 4/2012 | Delecrin et al. | 606/266 |
| 8,167,899 B2 | 5/2012 | Justis | |
| 8,197,516 B2 | 6/2012 | Biyani | |
| 8,202,216 B2 | 6/2012 | Melkent | |
| 8,206,291 B2 | 6/2012 | Fischvogt | |
| D663,030 S * | 7/2012 | Murner et al. | D24/143 |
| 8,211,151 B2* | 7/2012 | Schwab et al. | 606/264 |
| 8,211,152 B2 | 7/2012 | Snyder | |
| 8,221,457 B2* | 7/2012 | Delecrin et al. | 606/246 |
| 8,221,468 B2 | 7/2012 | Gaines | |
| 8,231,659 B2* | 7/2012 | Zolotov | 606/278 |
| 8,241,285 B2* | 8/2012 | Mullaney | 606/59 |
| 8,262,626 B2 | 9/2012 | Levendusky | |
| 8,262,710 B2 | 9/2012 | Freedman | |
| 8,298,269 B2* | 10/2012 | Null et al. | 606/267 |
| 8,313,459 B2 | 11/2012 | Kiehne | |
| 8,317,835 B2* | 11/2012 | Tornier | 606/265 |
| 8,323,318 B2* | 12/2012 | Baccelli et al. | 606/263 |
| 8,323,319 B2* | 12/2012 | Mazda et al. | 606/279 |
| 8,328,836 B2 | 12/2012 | Conlon | |
| 8,337,527 B2* | 12/2012 | Hawkins et al. | 606/278 |
| 8,361,130 B2 | 1/2013 | Daly | |
| 8,382,804 B2* | 2/2013 | Thomke et al. | 606/267 |
| 8,388,661 B2 | 3/2013 | Schlaepfer | |
| 8,414,616 B2* | 4/2013 | Berrevoets et al. | 606/250 |
| 8,430,916 B1* | 4/2013 | Winslow et al. | 606/278 |
| D682,426 S * | 5/2013 | Dominik et al. | D24/143 |
| D683,461 S * | 5/2013 | Murner et al. | D24/171 |
| 8,435,267 B2* | 5/2013 | Chin et al. | 606/264 |
| 8,454,658 B2* | 6/2013 | Lindner | 606/246 |
| 8,469,963 B2 | 6/2013 | Shoham | |
| 8,470,000 B2* | 6/2013 | Trautwein et al. | 606/249 |
| 8,506,598 B1* | 8/2013 | Tohmeh | 606/264 |
| 8,506,602 B2* | 8/2013 | Slivka et al. | 606/266 |
| 8,518,087 B2 | 8/2013 | Lopez | |
| 8,523,923 B2* | 9/2013 | Thomke et al. | 606/324 |
| 8,568,456 B2* | 10/2013 | Black | 606/250 |
| 8,585,741 B2* | 11/2013 | Gabelberger et al. | 606/264 |
| 2001/0001119 A1* | 5/2001 | Lombardo | 606/73 |
| 2001/0010000 A1* | 7/2001 | Gertzbein et al. | 606/61 |
| 2002/0068940 A1* | 6/2002 | Gaines, Jr. | 606/75 |
| 2002/0193795 A1* | 12/2002 | Gertzbein et al. | 606/61 |
| 2003/0120275 A1* | 6/2003 | Lenke et al. | 606/61 |
| 2003/0144665 A1* | 7/2003 | Munting | 606/61 |
| 2003/0171752 A1* | 9/2003 | Assaker et al. | 606/61 |
| 2003/0187438 A1* | 10/2003 | Assaker et al. | 606/61 |
| 2004/0138661 A1* | 7/2004 | Bailey | 606/61 |
| 2004/0147928 A1* | 7/2004 | Landry et al. | 606/61 |
| 2004/0147929 A1* | 7/2004 | Biedermann et al. | 606/61 |
| 2004/0162558 A1* | 8/2004 | Hegde et al. | 606/61 |
| 2004/0236333 A1 | 11/2004 | Lin | |
| 2004/0254574 A1* | 12/2004 | Morrison et al. | 606/61 |
| 2004/0267262 A1 | 12/2004 | Link | |
| 2005/0010215 A1* | 1/2005 | Delecrin et al. | 606/61 |
| 2005/0038433 A1* | 2/2005 | Young | 606/61 |
| 2005/0154388 A1* | 7/2005 | Roussouly et al. | 606/61 |
| 2005/0171537 A1* | 8/2005 | Mazel et al. | 606/61 |
| 2005/0171538 A1* | 8/2005 | Sgier et al. | 606/61 |
| 2005/0277920 A1* | 12/2005 | Slivka et al. | 606/61 |
| 2006/0004359 A1* | 1/2006 | Kramer et al. | 606/61 |
| 2006/0004360 A1* | 1/2006 | Kramer et al. | 606/61 |
| 2006/0009766 A1* | 1/2006 | Lee et al. | 606/61 |
| 2006/0036250 A1 | 2/2006 | Lange | |
| 2006/0052811 A1 | 3/2006 | Blanco | |
| 2006/0079892 A1* | 4/2006 | Roychowdhury et al. | 606/61 |
| 2006/0079899 A1* | 4/2006 | Ritland | 606/61 |
| 2006/0116676 A1* | 6/2006 | Gradel et al. | 606/61 |
| 2006/0167455 A1* | 7/2006 | Clement et al. | 606/61 |
| 2006/0206114 A1* | 9/2006 | Ensign et al. | 606/61 |
| 2006/0229606 A1* | 10/2006 | Clement et al. | 606/61 |
| 2006/0229616 A1* | 10/2006 | Albert et al. | 606/61 |
| 2006/0241601 A1* | 10/2006 | Trautwein et al. | 606/61 |
| 2006/0253118 A1* | 11/2006 | Bailey | 606/61 |
| 2007/0049932 A1* | 3/2007 | Richelsoph et al. | 606/61 |
| 2007/0078463 A1 | 4/2007 | Malandain | |
| 2007/0118124 A1* | 5/2007 | Biedermann et al. | 606/61 |
| 2007/0123860 A1* | 5/2007 | Francis et al. | 606/61 |
| 2007/0162006 A1* | 7/2007 | Ritland | 606/61 |
| 2007/0233066 A1* | 10/2007 | Rezach | 606/61 |
| 2007/0255305 A1 | 11/2007 | McMichael | |
| 2007/0270816 A1* | 11/2007 | Rezach | 606/61 |
| 2007/0270817 A1* | 11/2007 | Rezach | 606/61 |
| 2007/0270818 A1 | 11/2007 | Rezach | |
| 2007/0282365 A1 | 12/2007 | Popov | |
| 2007/0299459 A1 | 12/2007 | Way | |
| 2008/0051821 A1 | 2/2008 | Gephart | |
| 2008/0140124 A1 | 6/2008 | Jeon | |
| 2008/0177323 A1* | 7/2008 | Null et al. | 606/267 |
| 2008/0208257 A1* | 8/2008 | Matthys | 606/278 |
| 2008/0255617 A1* | 10/2008 | Cho et al. | 606/246 |
| 2008/0262553 A1* | 10/2008 | Hawkins et al. | 606/278 |
| 2008/0294203 A1* | 11/2008 | Kovach et al. | 606/308 |
| 2008/0300630 A1* | 12/2008 | Bonnema et al. | 606/246 |
| 2008/0306551 A1* | 12/2008 | Sanders et al. | 606/301 |
| 2009/0099602 A1 | 4/2009 | Aflatoon | |
| 2009/0131985 A1* | 5/2009 | Mazda et al. | 606/246 |
| 2009/0138048 A1* | 5/2009 | Baccelli et al. | 606/263 |
| 2009/0143738 A1 | 6/2009 | Hendriksen | |
| 2009/0149857 A1 | 6/2009 | Culbert | |
| 2009/0163942 A1 | 6/2009 | Cuevas | |
| 2009/0182379 A1* | 7/2009 | Baccelli et al. | 606/263 |
| 2009/0187217 A1* | 7/2009 | Weiman et al. | 606/257 |
| 2009/0216242 A1 | 8/2009 | Riemer | |
| 2009/0264926 A1* | 10/2009 | Taylor et al. | 606/246 |
| 2009/0275970 A1 | 11/2009 | Leibowitz | |
| 2009/0326585 A1* | 12/2009 | Baccelli et al. | 606/263 |
| 2009/0326588 A1* | 12/2009 | Felix et al. | 606/277 |
| 2010/0094346 A1* | 4/2010 | Matityahu | 606/250 |
| 2010/0094358 A1 | 4/2010 | Moore | |
| 2010/0152787 A1 | 6/2010 | Walsh | |
| 2010/0241171 A1* | 9/2010 | Clement et al. | 606/264 |
| 2010/0324488 A1 | 12/2010 | Smith | |
| 2011/0034956 A1* | 2/2011 | Mazda et al. | 606/278 |
| 2011/0071569 A1* | 3/2011 | Black | 606/250 |

(56) References Cited

U.S. PATENT DOCUMENTS

| | | |
|---|---|---|
| 2011/0144687 A1 | 6/2011 | Kleiner |
| 2011/0238118 A1* | 9/2011 | Baccelli et al. ............... 606/263 |
| 2011/0245857 A1 | 10/2011 | Stan |
| 2011/0270325 A1 | 11/2011 | Keyer |
| 2011/0319940 A1* | 12/2011 | Slivka et al. .................. 606/264 |
| 2012/0004665 A1 | 1/2012 | Defossez |
| 2012/0022591 A1* | 1/2012 | Baccelli et al. ............... 606/263 |
| 2012/0022592 A1* | 1/2012 | Belliard ....................... 606/263 |
| 2012/0029566 A1* | 2/2012 | Rezach ......................... 606/264 |
| 2012/0029567 A1* | 2/2012 | Zolotov et al. ................ 606/264 |
| 2012/0065685 A1* | 3/2012 | Lee et al. ...................... 606/250 |
| 2012/0095417 A1 | 4/2012 | Justis |
| 2012/0108926 A1 | 5/2012 | Kassab |
| 2012/0197298 A1* | 8/2012 | Baccelli et al. ............... 606/264 |
| 2012/0290010 A1* | 11/2012 | Zamani et al. ................ 606/264 |
| 2013/0123854 A1* | 5/2013 | Kondrashov et al. ......... 606/264 |
| 2013/0253516 A1* | 9/2013 | Mackall ......................... 606/70 |
| 2013/0261668 A1* | 10/2013 | Douget et al. ................ 606/278 |
| 2013/0268004 A1* | 10/2013 | Rathbun ........................ 606/252 |
| 2013/0325070 A1* | 12/2013 | Larroque-Lahitette et al. ............................ 606/277 |

FOREIGN PATENT DOCUMENTS

| | | |
|---|---|---|
| DE | 4429744 | 2/1996 |
| EP | 0637437 | 2/1995 |
| EP | 0888754 | 1/1999 |
| FR | 2704136 | 10/1994 |
| KR | 20010112139 | 12/2001 |
| WO | WO-9400062 | 1/1994 |
| WO | WO-9632882 | 10/1996 |
| WO | WO-9848719 | 5/1999 |
| WO | WO-0241796 | 5/2002 |
| WO | WO-03096914 | 11/2003 |
| WO | WO-2005004947 | 1/2005 |
| WO | WO-2006111852 | 10/2006 |

* cited by examiner

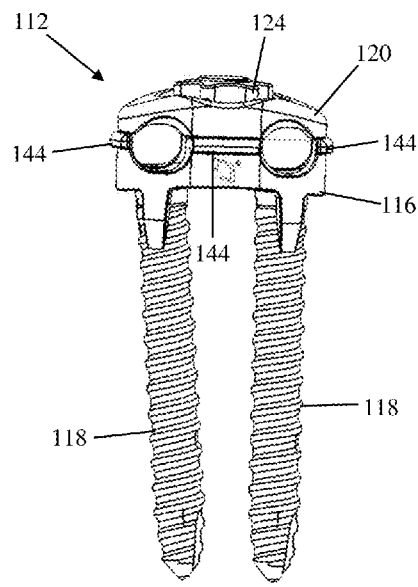
Fig. 15
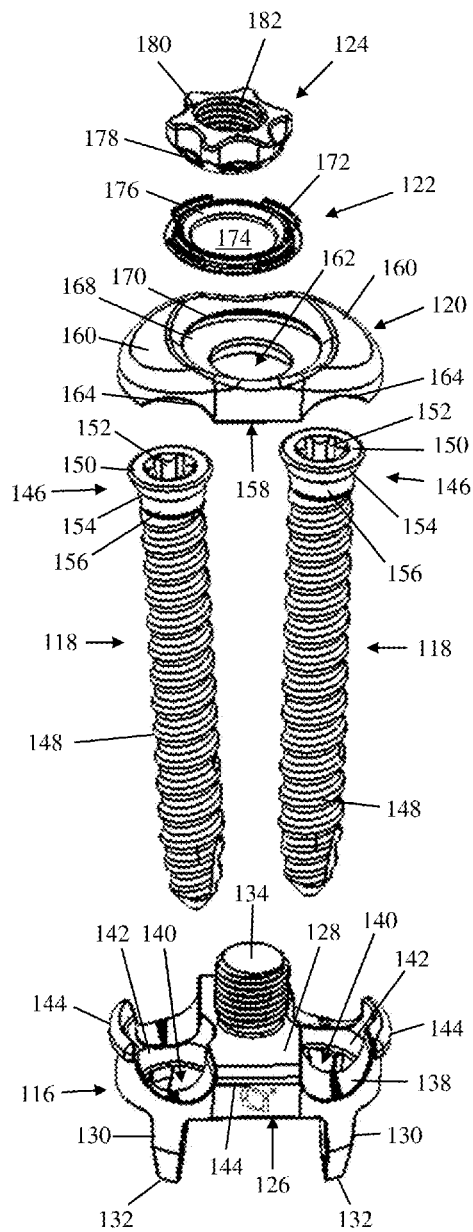
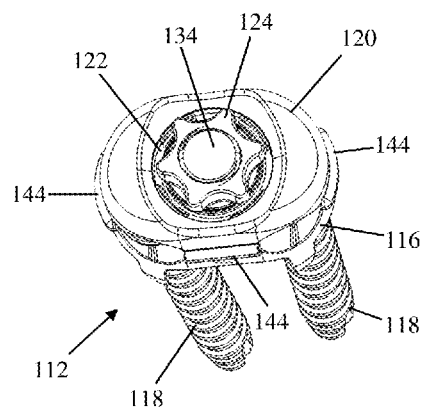
Fig. 16
Fig. 17

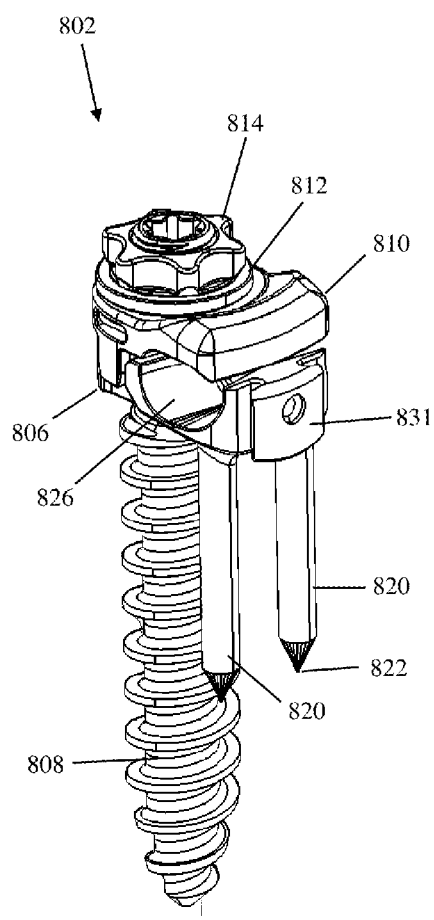
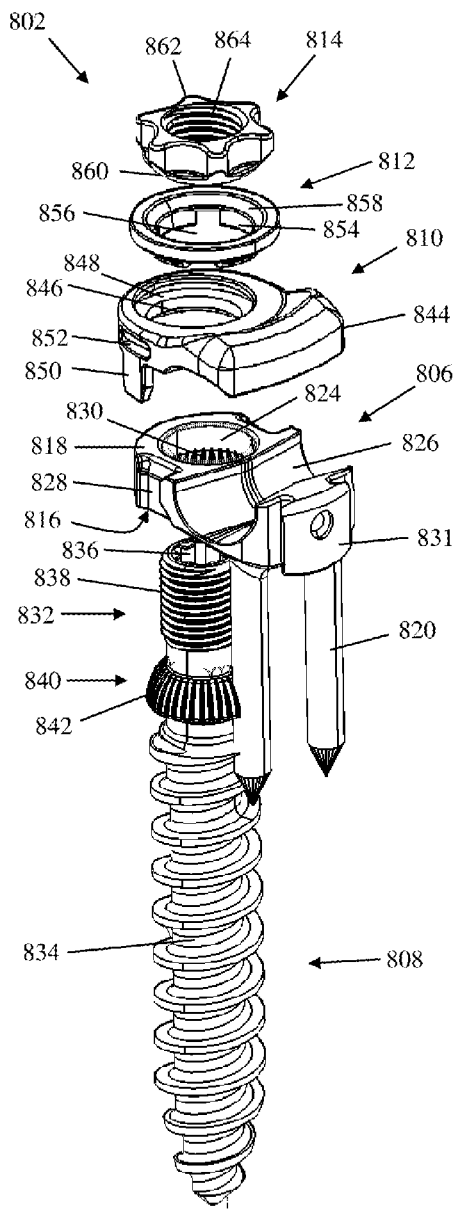
Fig. 82
Fig. 83

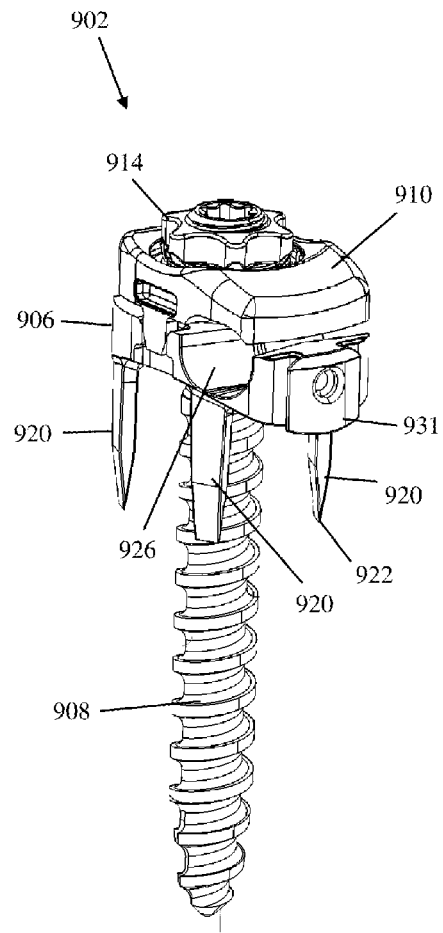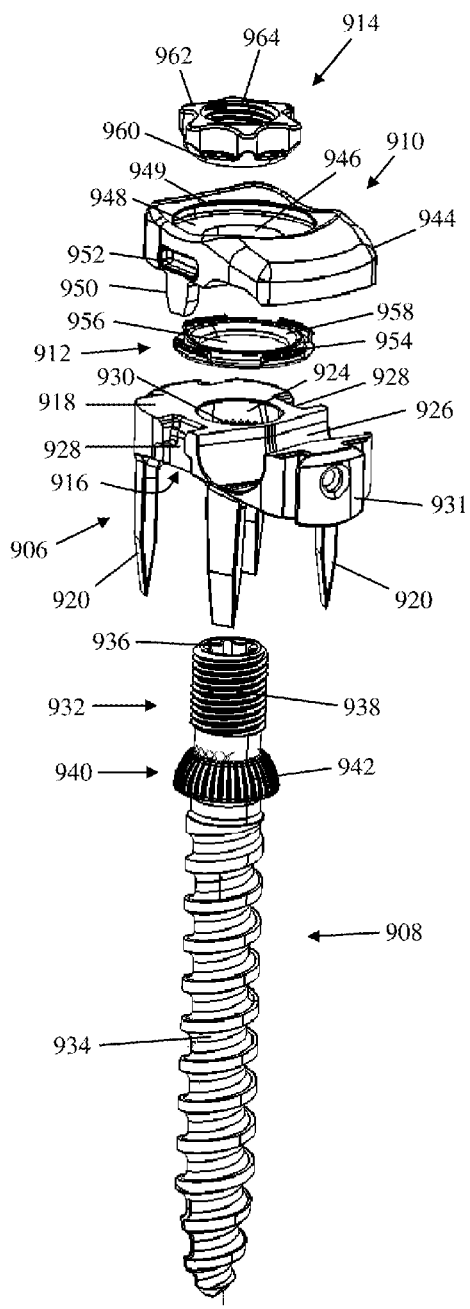
Fig. 84
Fig. 85

US 8,992,579 B1

LATERAL FIXATION CONSTRUCTS AND RELATED METHODS

CROSS REFERENCES TO RELATED APPLICATIONS

The present application is a non-provisional application claiming the benefit of priority under 35 U.S.C. §119(e) from commonly owned and U.S. Provisional Application Ser. No. 61/450,595 filed on Mar. 8, 2011 and entitled "Lateral Fixation Constructs and Related Methods," the entire contents of which is hereby incorporated by reference into this disclosure as if set forth fully herein. This application also incorporates by reference the entire contents of commonly-owned U.S. patent application Ser. No. 10/967,668 entitled "Surgical Access System and Related Methods," filed Oct. 18, 2004 and issued as U.S. Pat. No. 7,905,840 on Mar. 15, 2011.

FIELD

The present application relates generally to implants, instruments, and methods for performing spinal fixation.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g., walking, talking, breathing, etc.). Therefore, it is of great interest and concern to be able to both correct and prevent any ailments of the spine.

Fixation systems are often surgically implanted to stabilize or immobilize a portion of the spine. They are generally utilized during spinal fusion procedures to immobilize the applicable vertebrae until bone growth occurs to effect the fusion and/or to correct vertebral alignment issues. Fixation systems often use a combination of rods, plates, pedicle screws, and bone hooks to attach a fixation construct to the affected vertebrae. The configuration required for each procedure and patient varies due to the ailment being treated, the specific method of treatment (e.g. surgical approach, etc. . . . ) and the patient's specific anatomical characteristics. Thus there remains a need for continued improvements and new systems for spinal fixation.

BRIEF DESCRIPTIONS OF THE DRAWINGS

Many advantages of the present invention will be apparent to those skilled in the art with a reading of this specification in conjunction with the attached drawings, wherein like reference numerals are applied to like elements and wherein:

FIG. 7 is a plan view of a reducer instrument for use with the vertebral fixation system of

Figure 1:
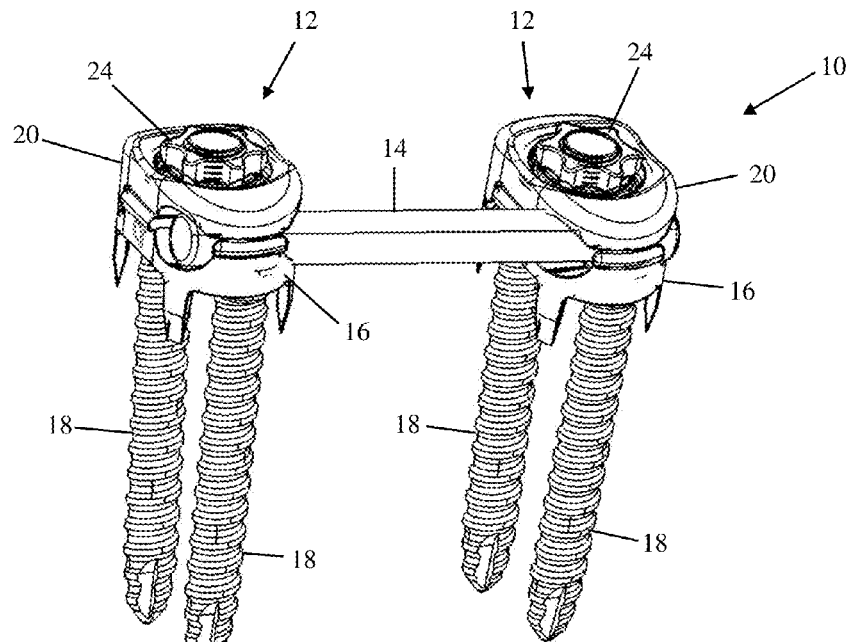
FIGS. 1 and 2 are perspective views of one example of a vertebral fixation system according to a first embodiment of the present invention.
Figure 2:
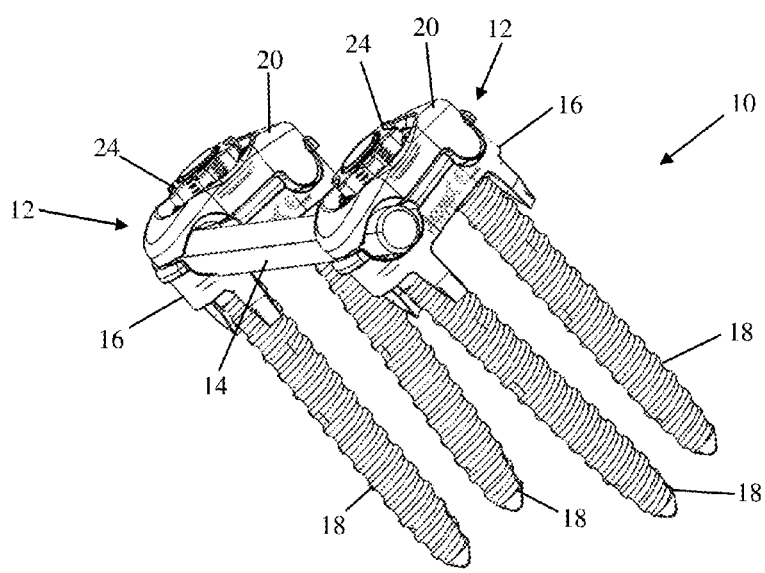
Figure 3:
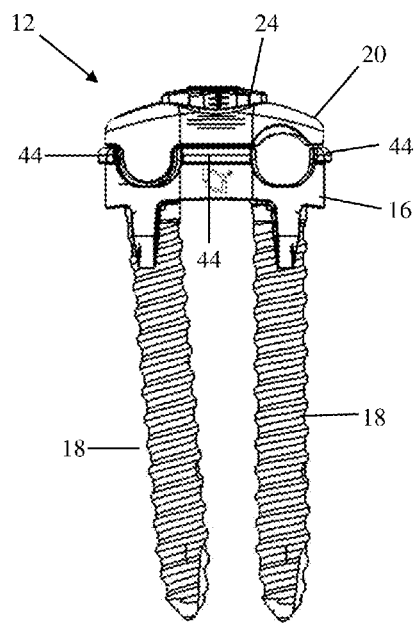
FIGS. 3 and 4 are plan and perspective views, respectively, of an anchor assembly forming part of the vertebral fixation system of FIG. 1.
Figure 4:
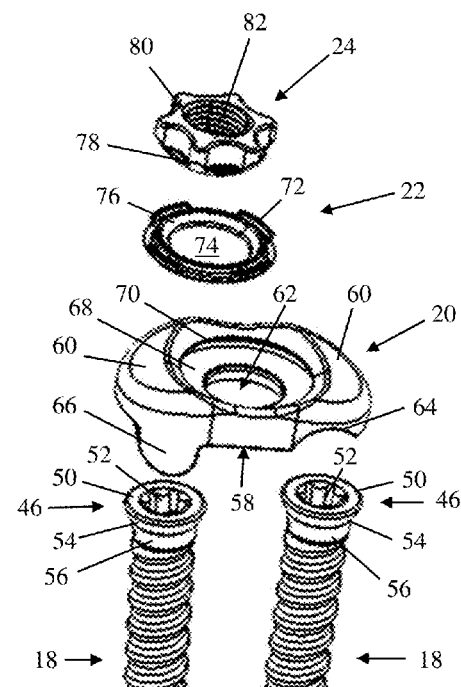
Figure 4:
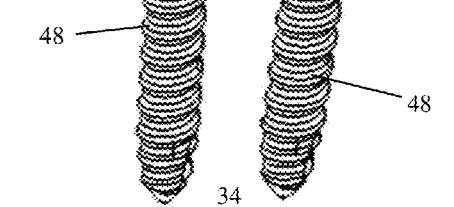
Figure 5:
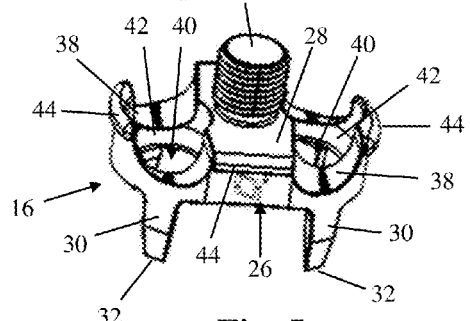
FIG. 5 is an exploded view of the anchor assembly of FIG. 3.
Figure 6:
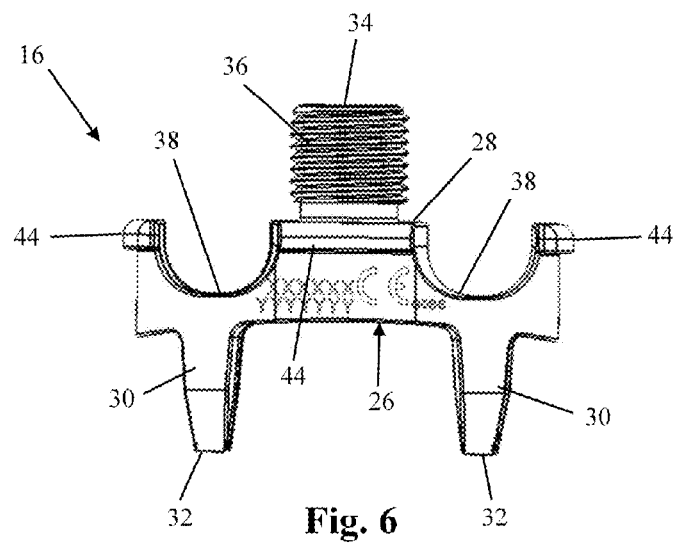
FIG. 6 is a plan view of a staple body forming part of the anchor assembly of FIG. 3.
Figure 7:
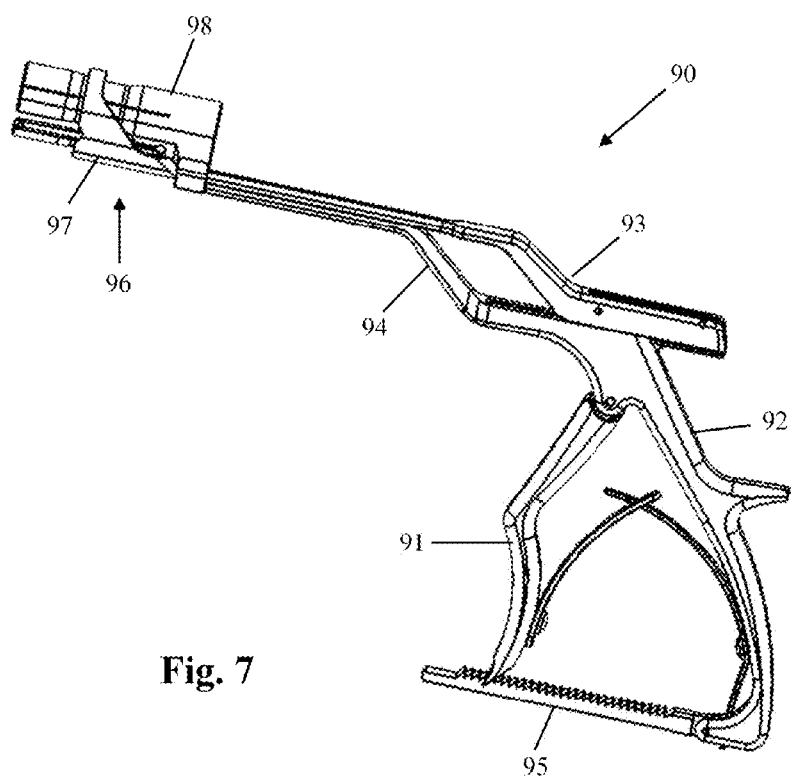
Figure 8:
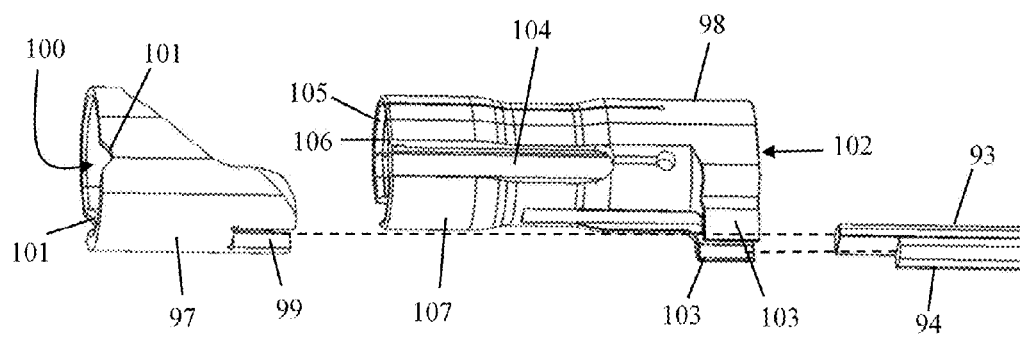
Figure 9:
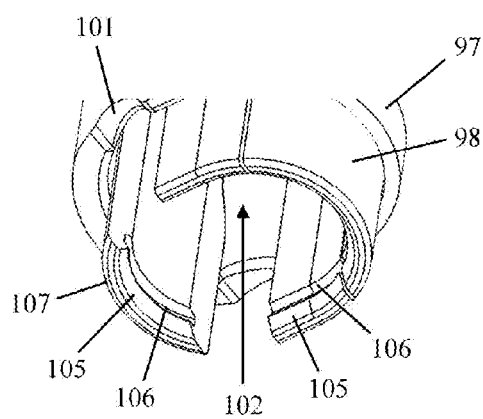
Figure 10:
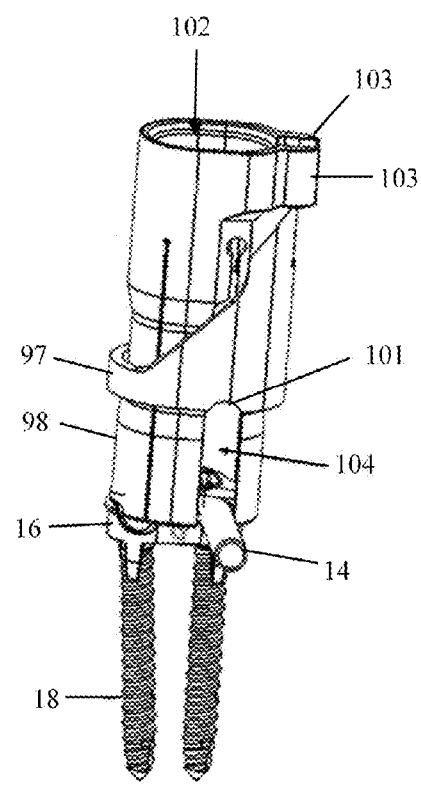
Figure 11:
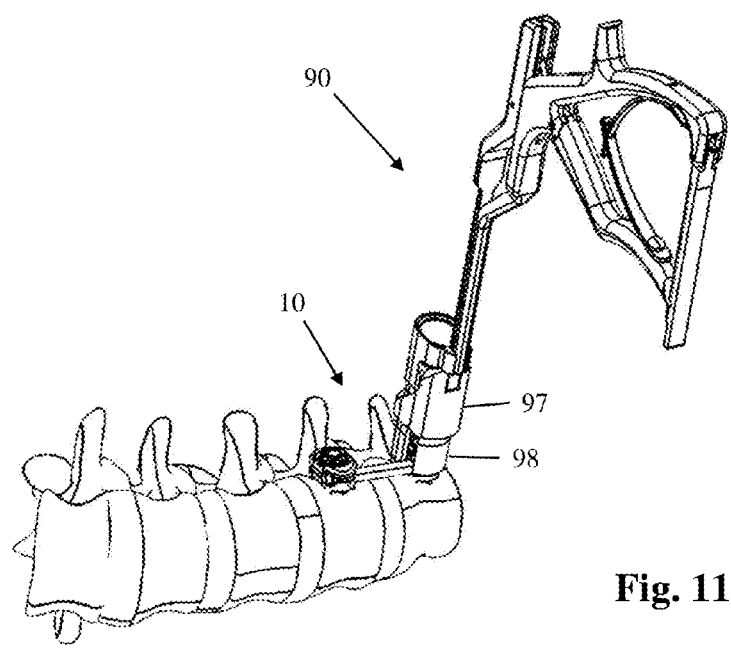
Figure 12:
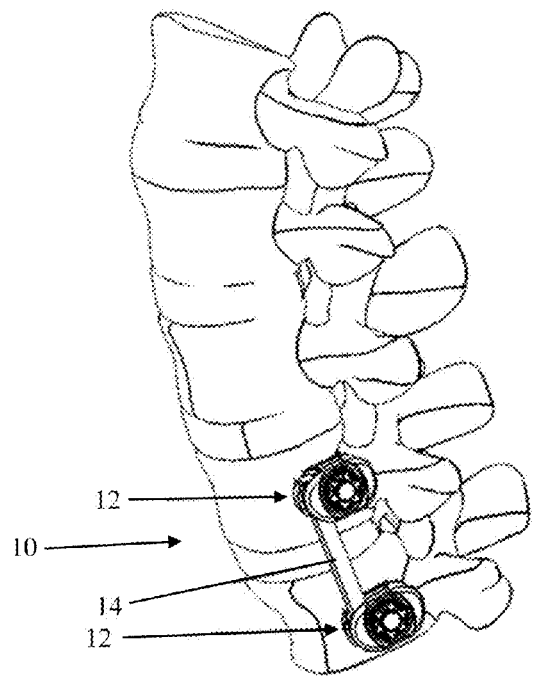
Figure 13:
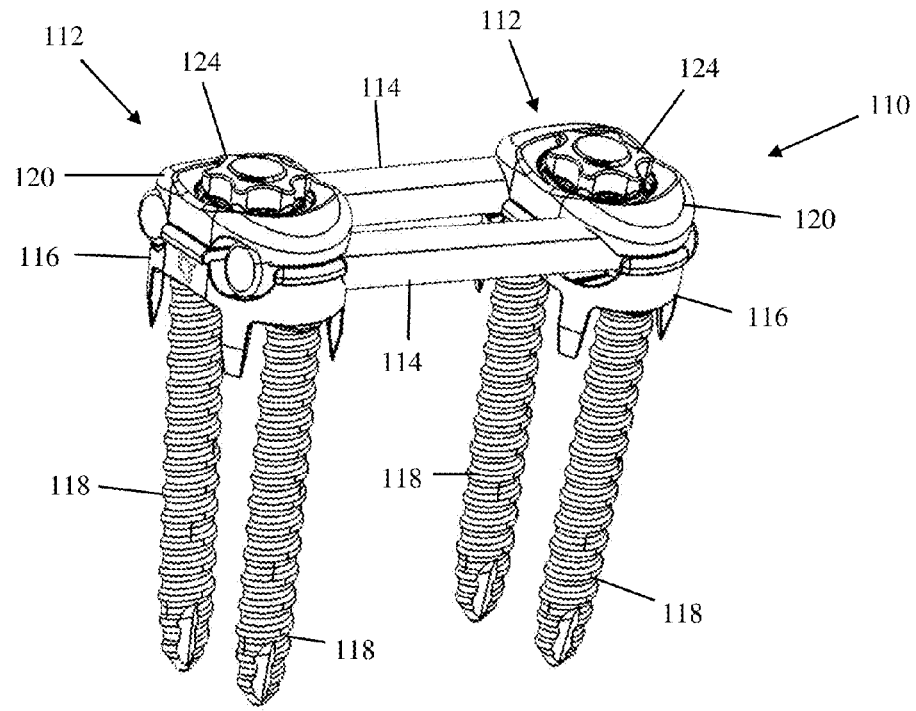
Figure 14:
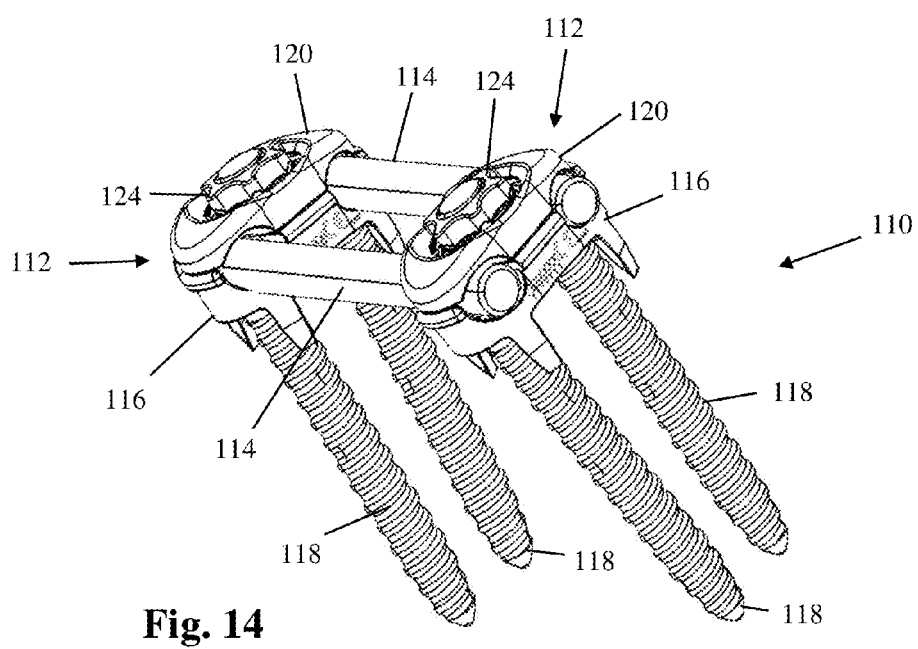
Figure 18:
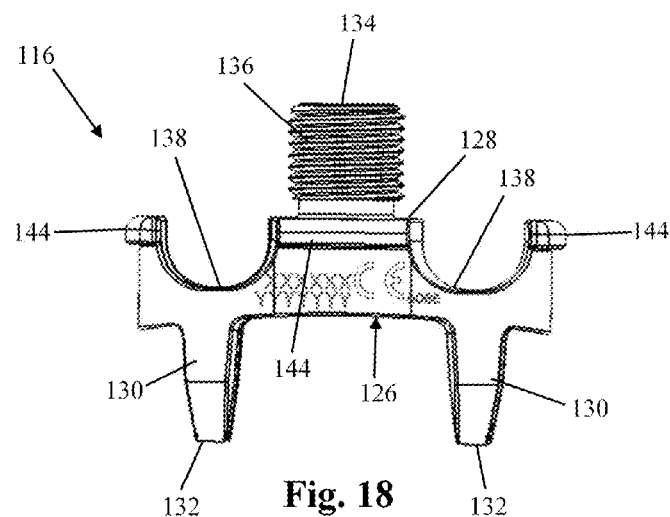
Figure 19:
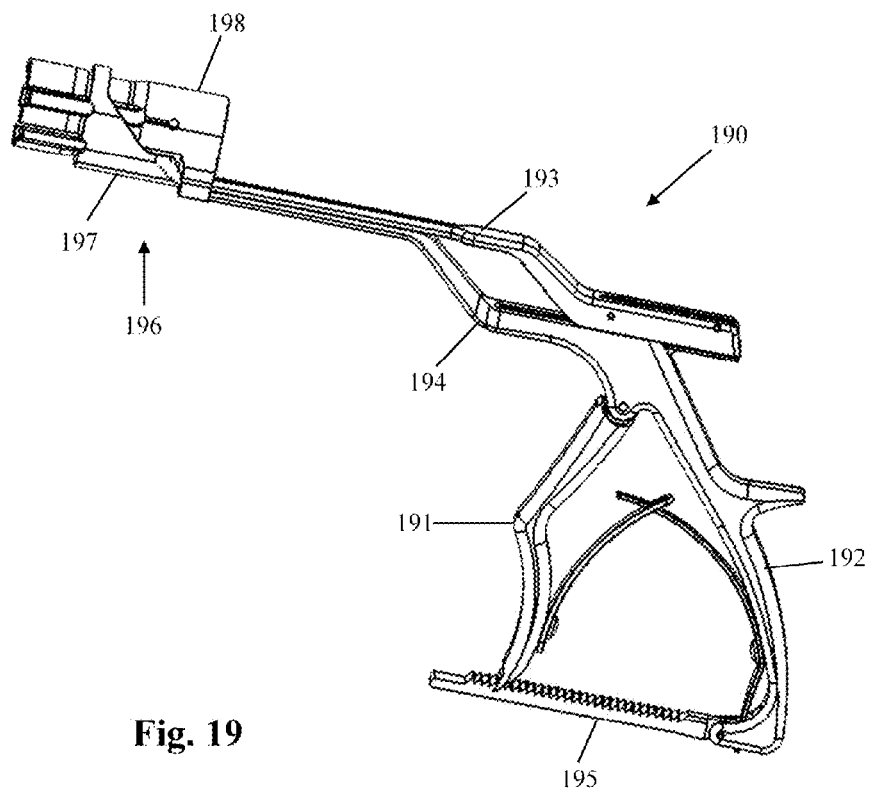
Figure 20:
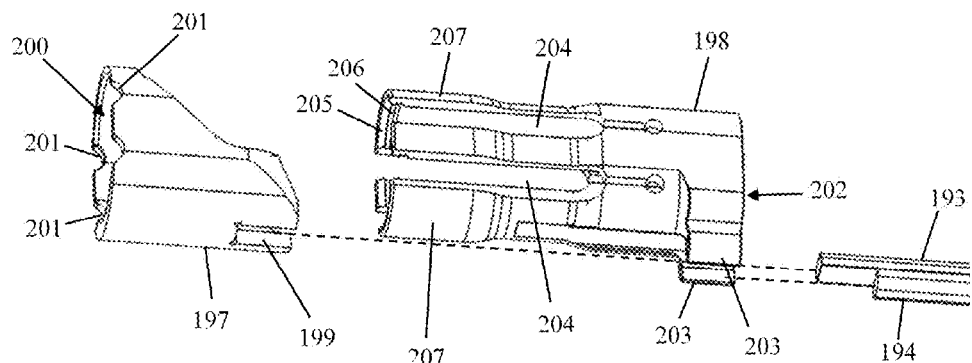
Figure 21:
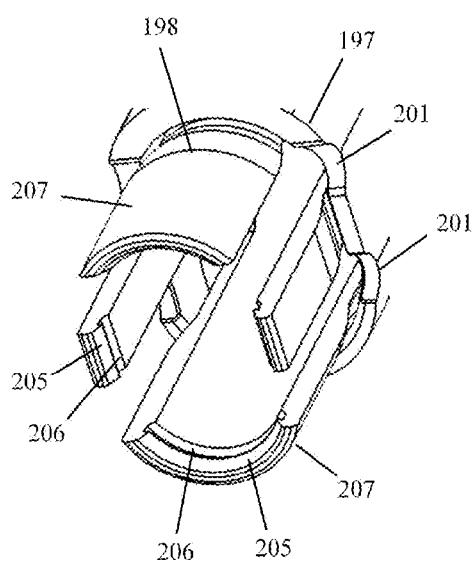
Figure 22:
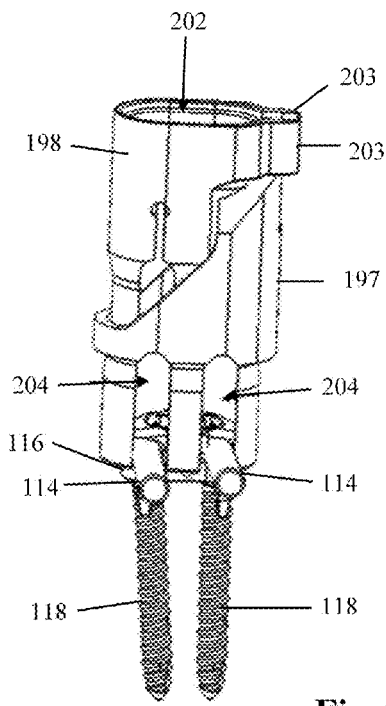
Figure 23:
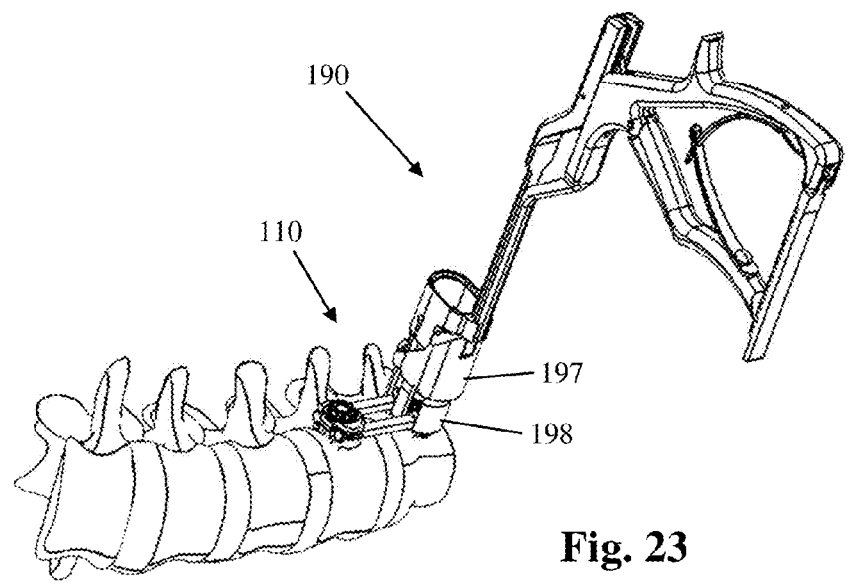
Figure 24:
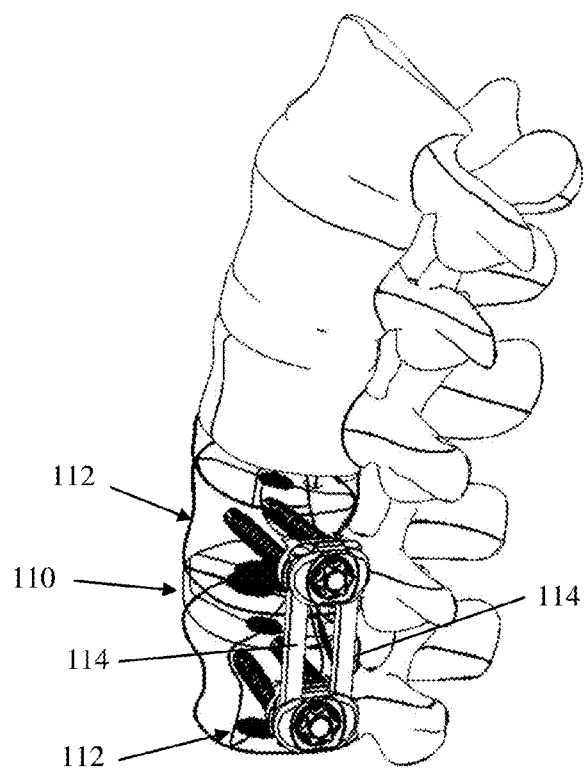
Figure 25:
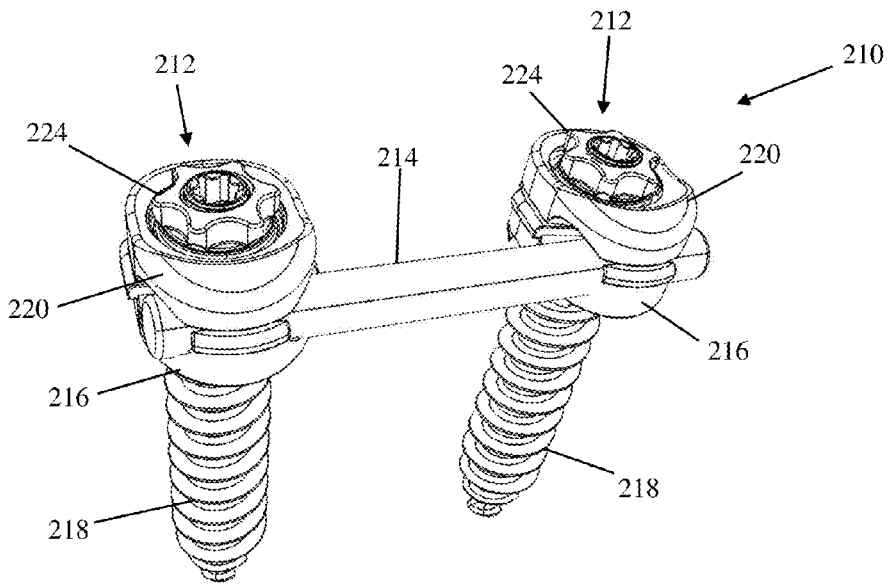
Figure 26:
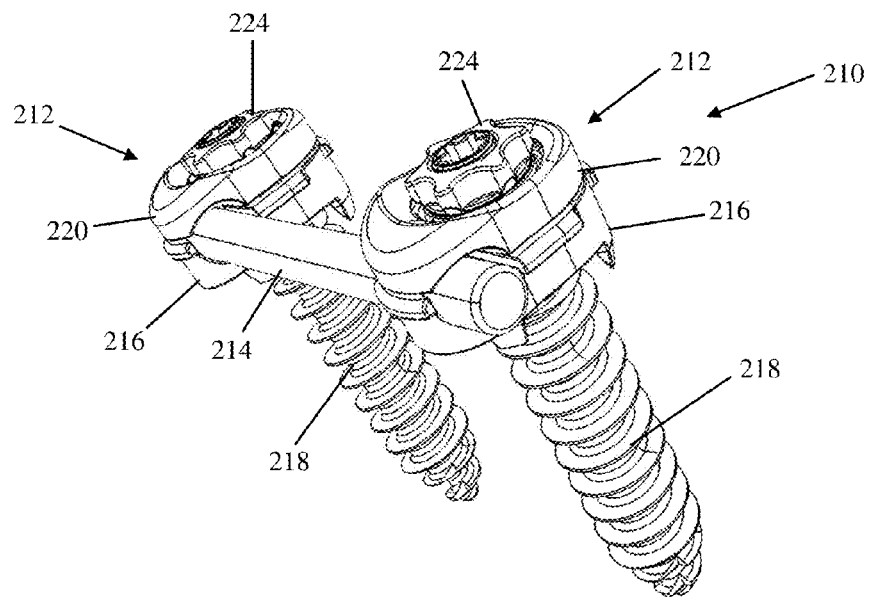
Figure 27:
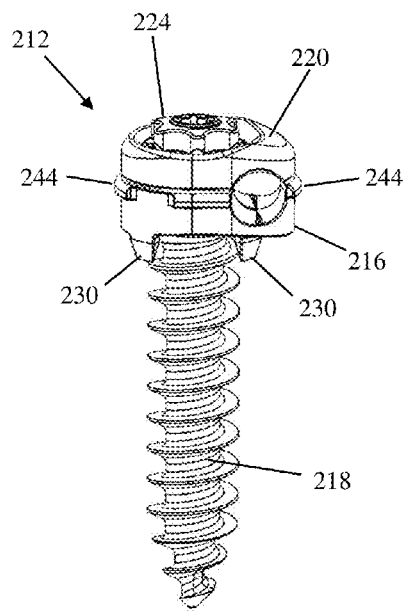
Figure 28:
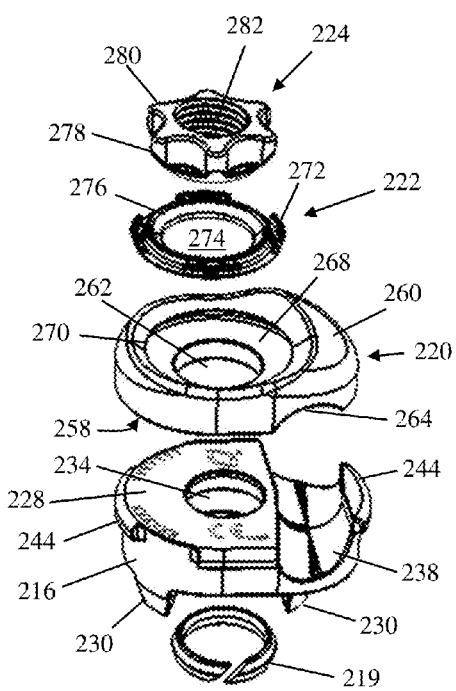
Figure 28:
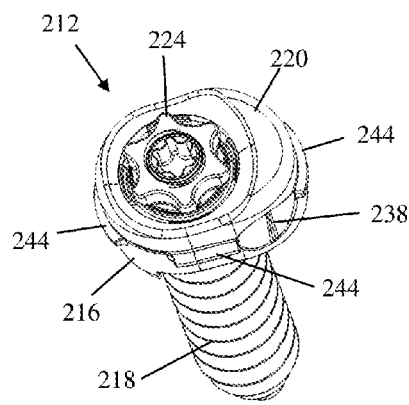
Figure 29:
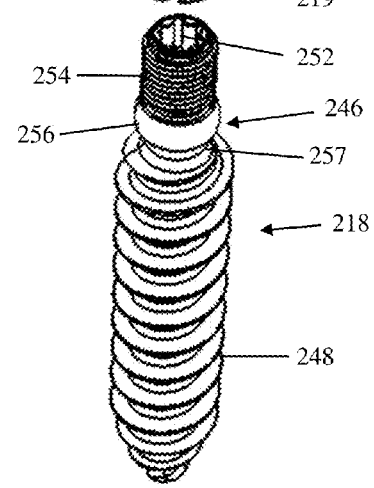
Figure 30:
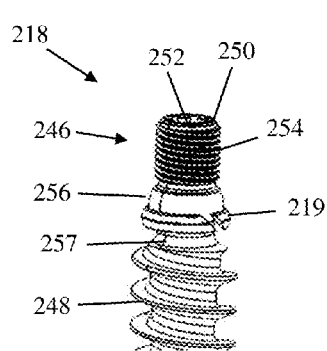
Figure 31:
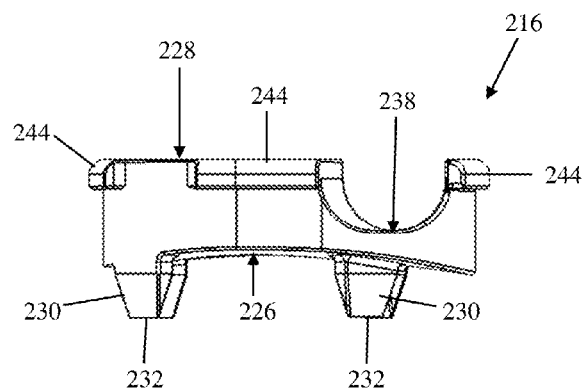
Figure 32:
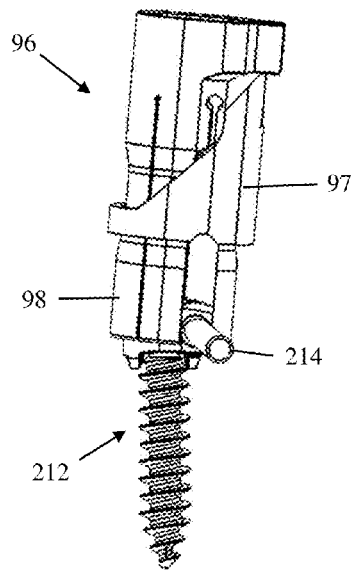
Figure 33:
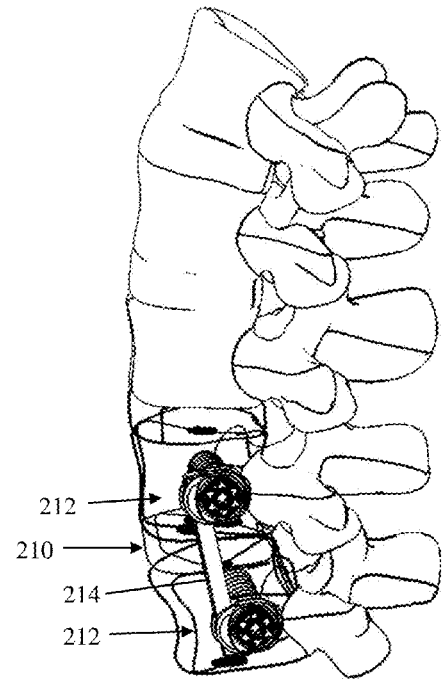
Figure 34:
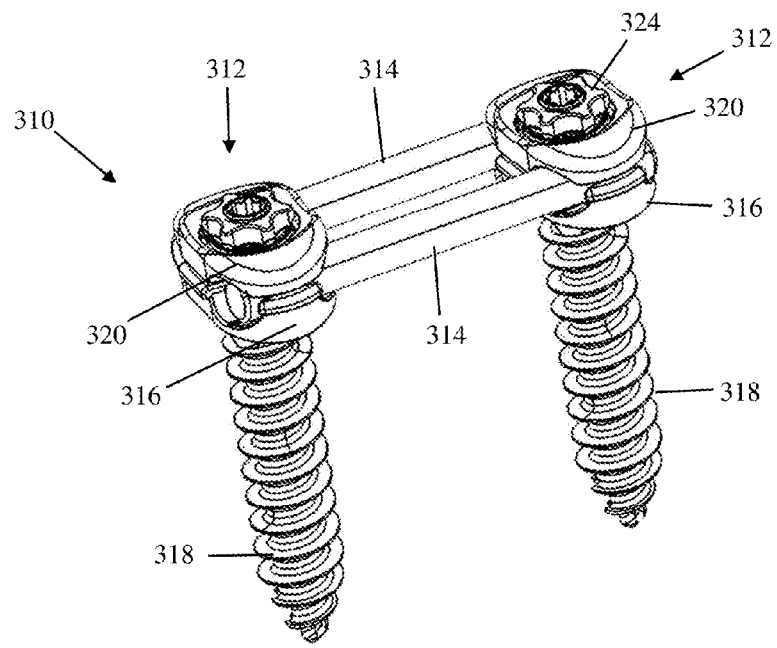
Figure 35:
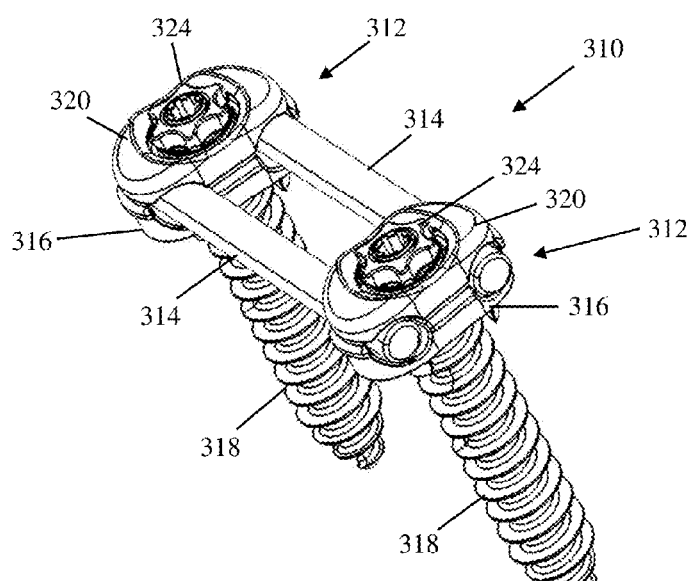
Figure 36:
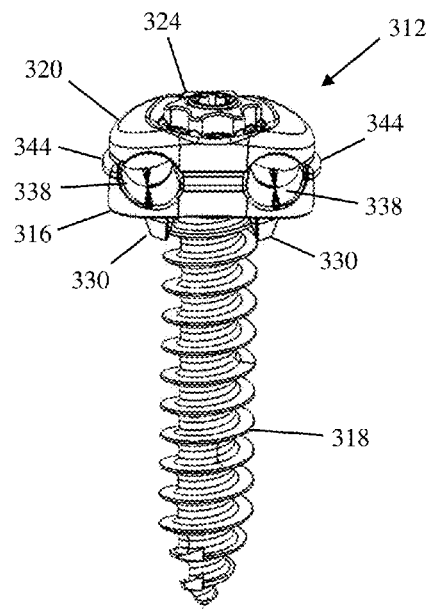
Figure 37:
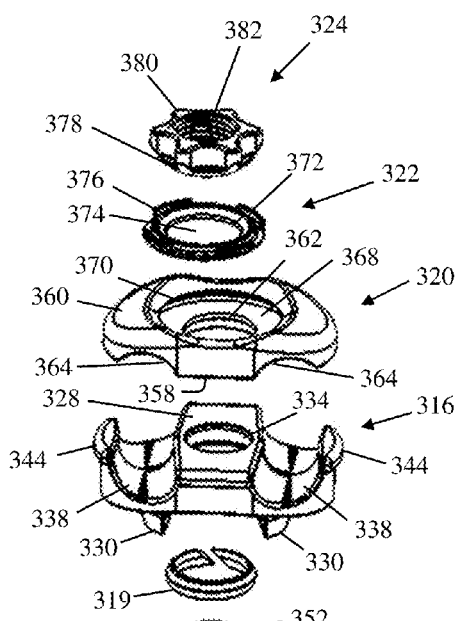
Figure 37:
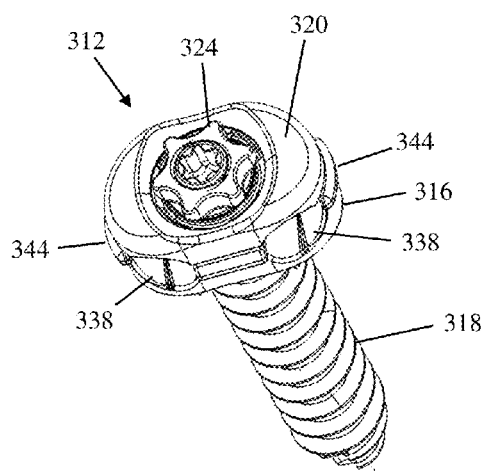
Figure 38:
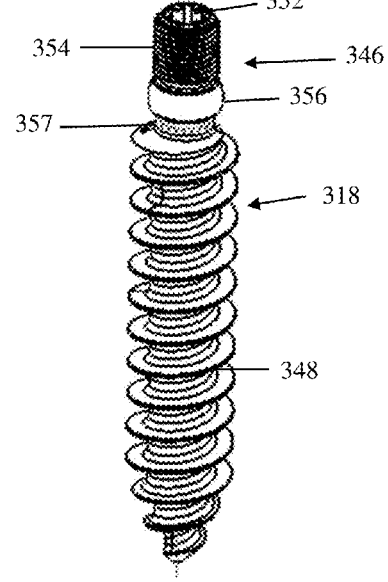
Figure 39:
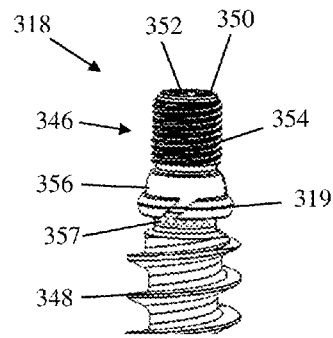
Figure 40:
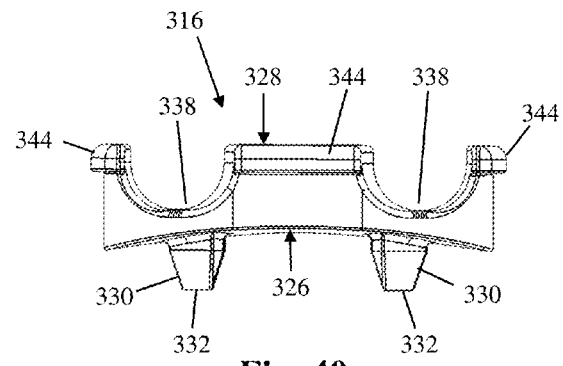
Figure 41:
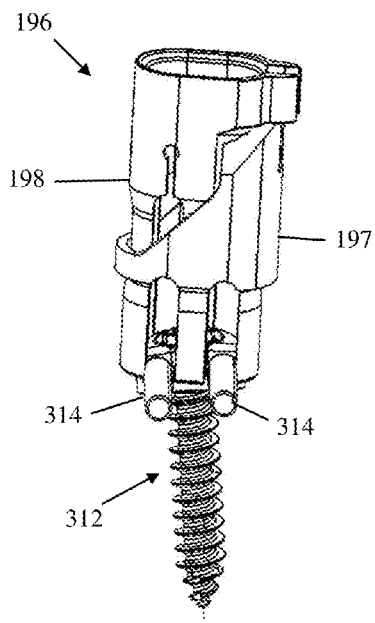
Figure 42:
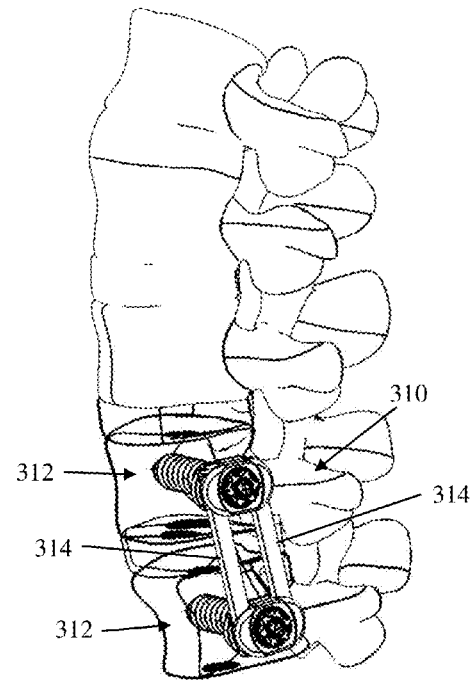
Figure 43:
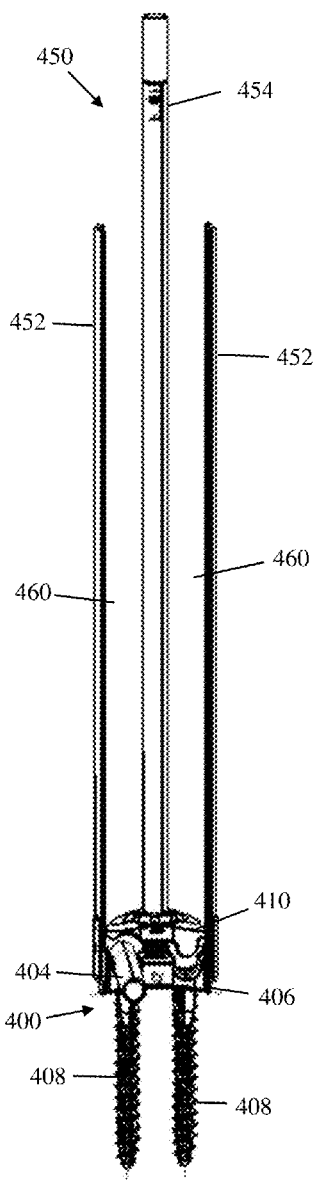
Figure 44:
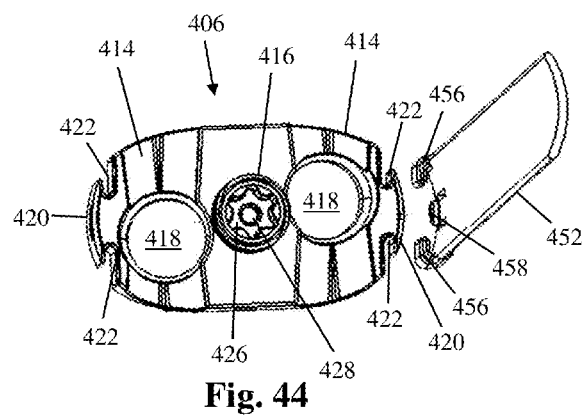
Figure 45:
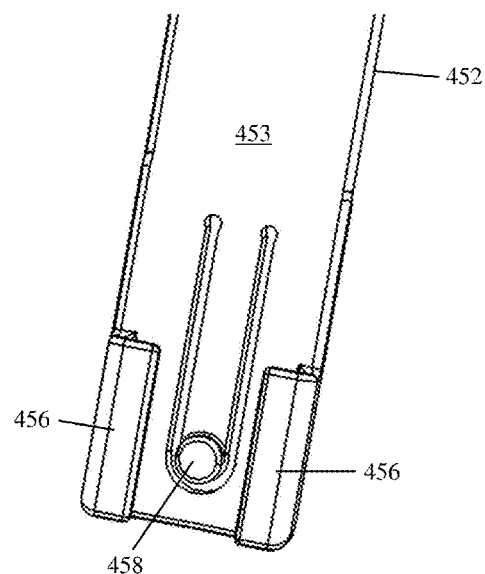
Figure 46:
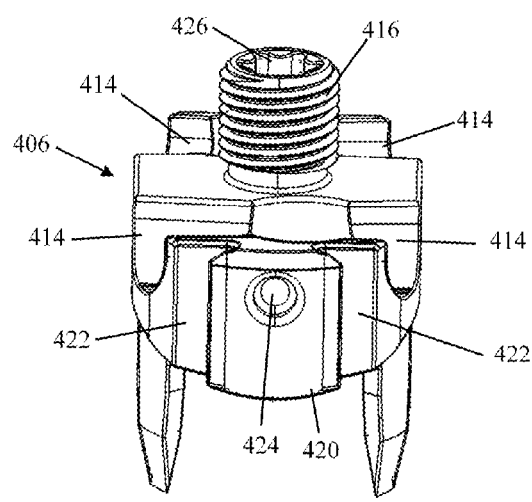
Figure 47:
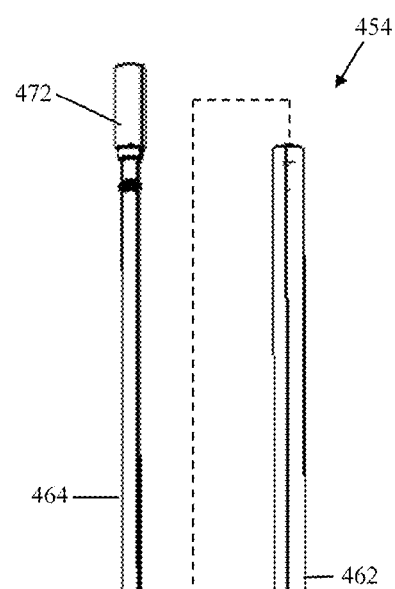
Figure 48:
Figure 49:
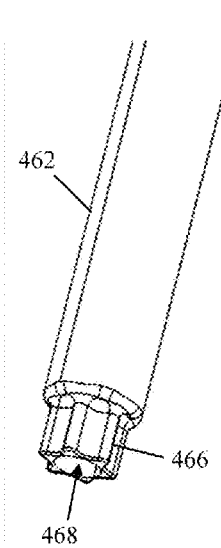
Figure 50:
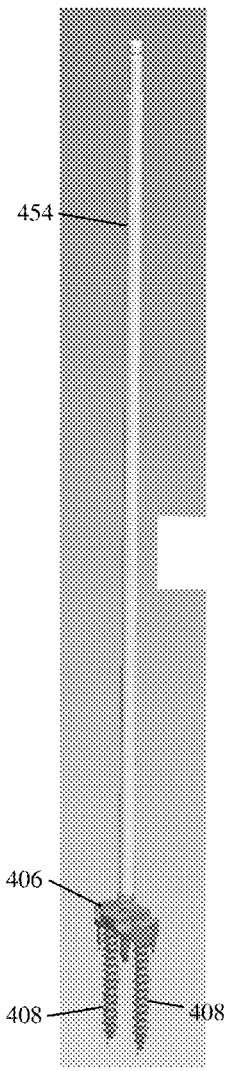
Figure 51:
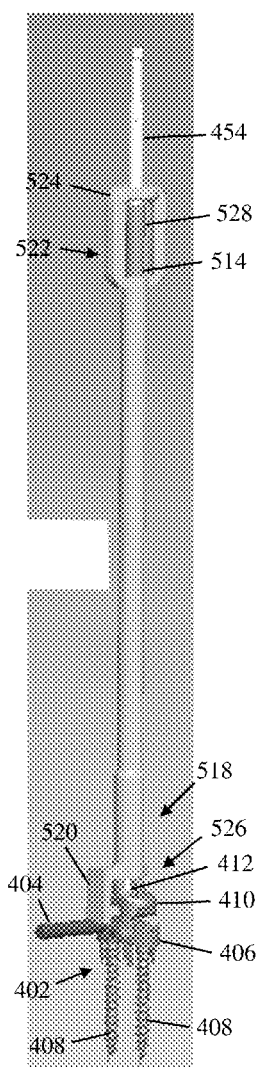
Figure 63:
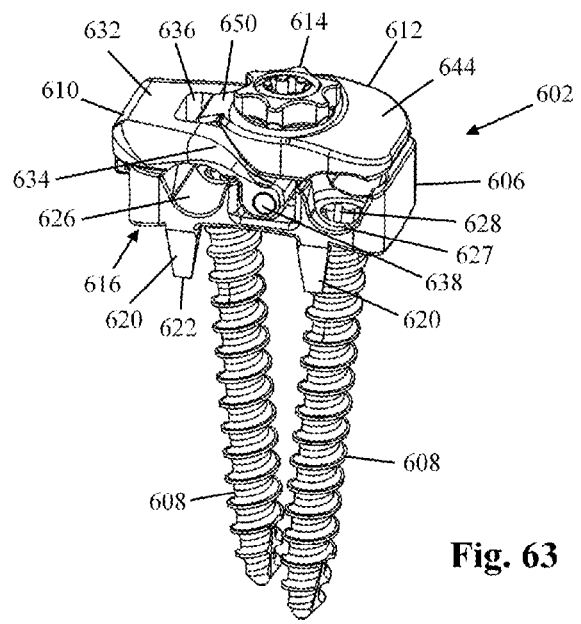
Figure 69:
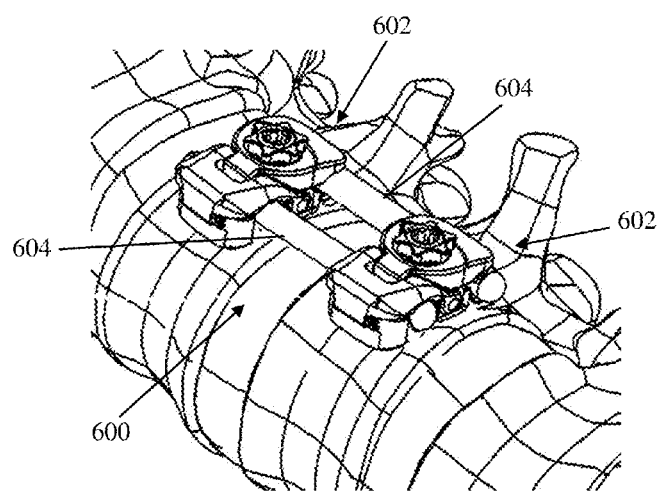
Figure 70:
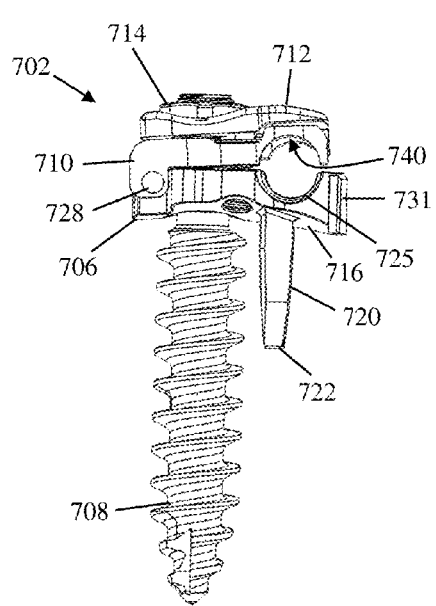
Figure 71:
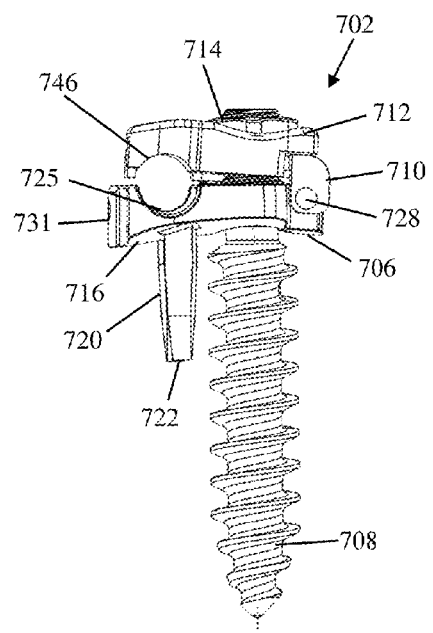
Figure 72:
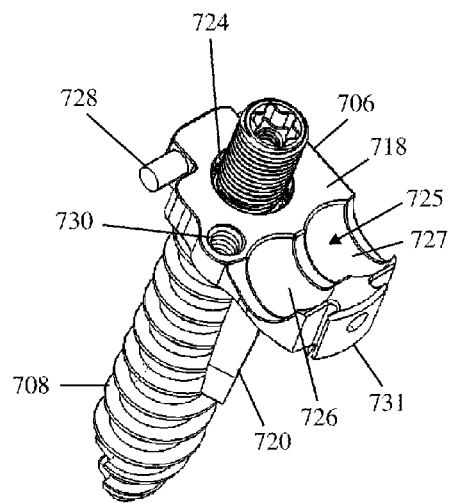
Figure 73:
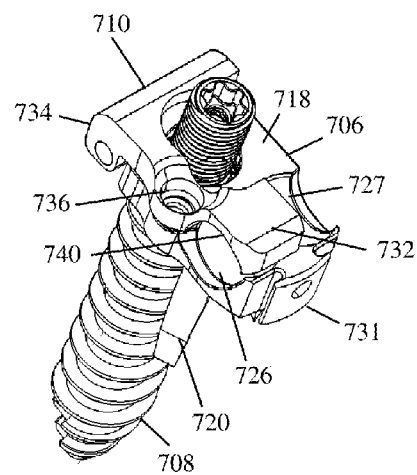
Figure 74:
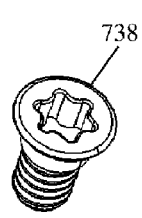
Figure 75:
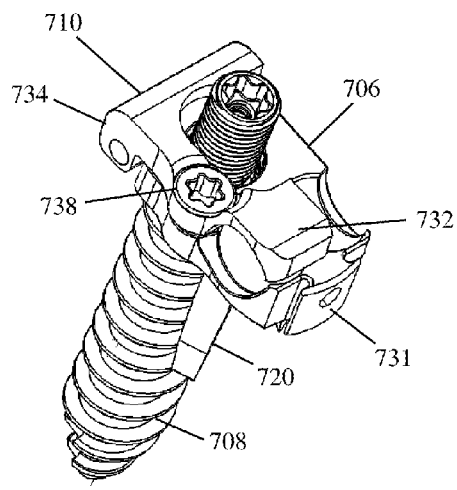
Figure 76:
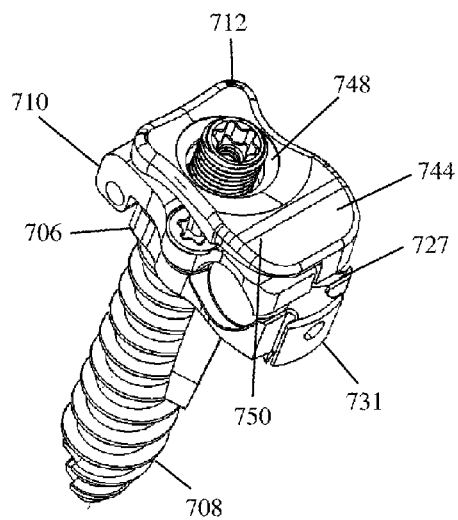
Figure 77:
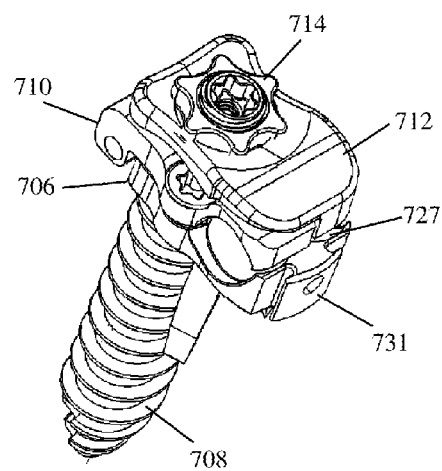
Figure 78:
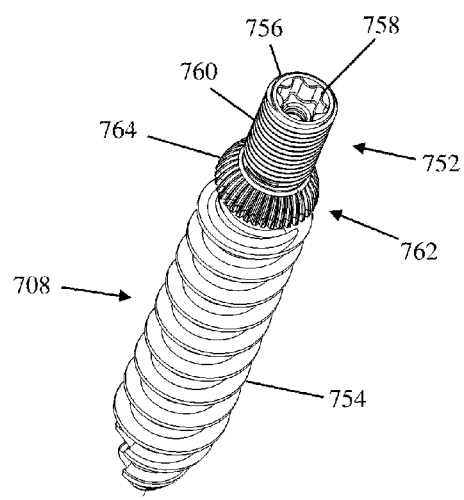
Figure 79:
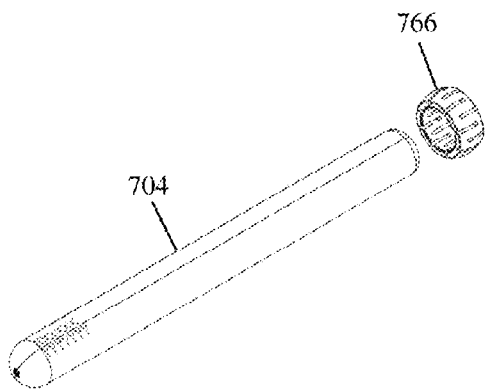
Figure 80:
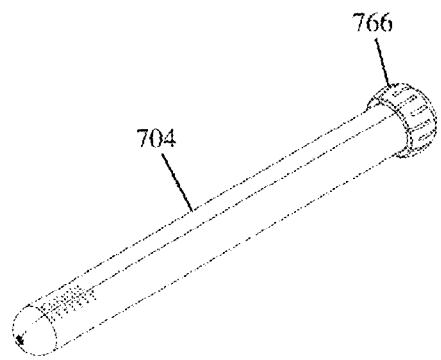
Figure 81:
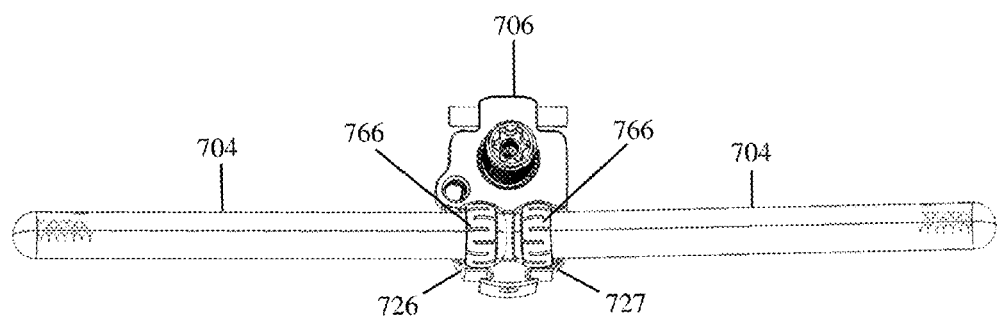
Figure 86:
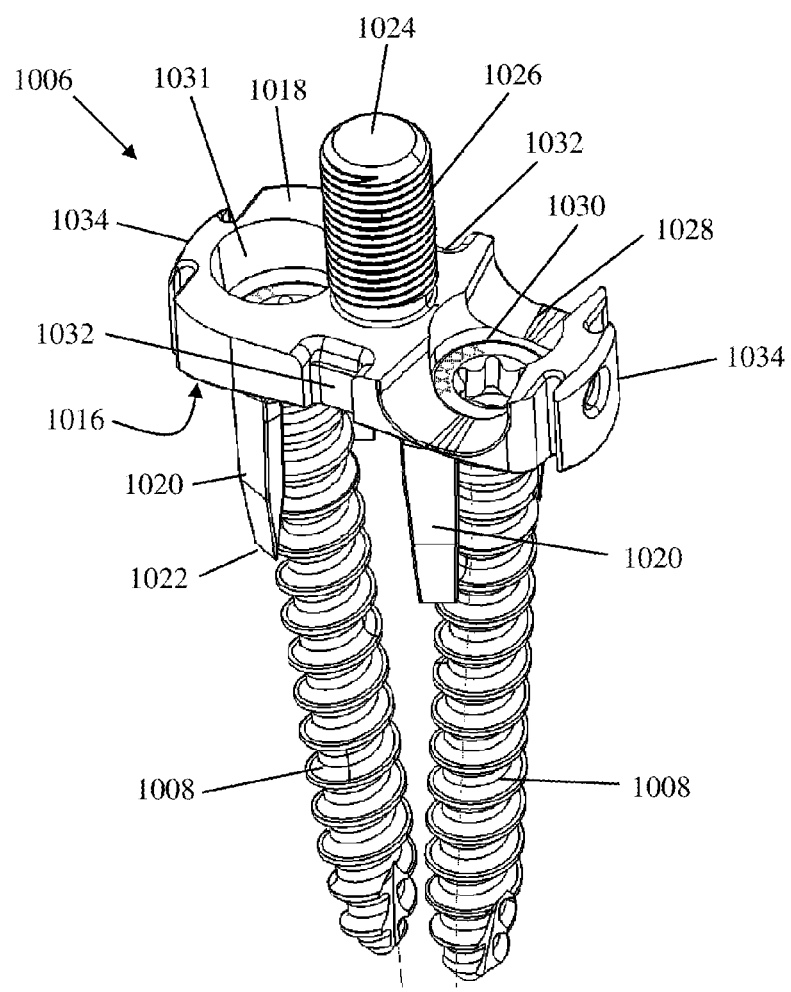

FIG. 1;

FIG. 8 is an exploded view of the distal end of the reducer instrument of FIG. 7;

FIG. 9 is a perspective view of the distal end of the reducer instrument of FIG. 7;

FIG. 10 is a perspective view of the distal end of the reducer instrument of FIG. 7 engaged with the anchor assembly of FIG. 3;

FIG. 11 is a perspective view of the reducer instrument of FIG. 7 engaged with the anchor assembly of FIG. 3 during implantation of the vertebral fixation system into a spine;

FIG. 12 is a perspective view of the vertebral fixation system of FIG. 1 fully implanted into the spine;

FIGS. 13 and 14 are perspective views of one example of a vertebral fixation system according to a second embodiment of the present invention;

FIGS. 15 and 16 are plan and perspective views, respectively, of an anchor assembly forming part of the vertebral fixation system of FIG. 13;

FIG. 17 is an exploded view of the anchor assembly of FIG. 15;

FIG. 18 is a plan view of a staple body forming part of the anchor assembly of FIG. 15;

FIG. 19 is a plan view of a reducer instrument for use with the vertebral fixation system of FIG. 13;

FIG. 20 is an exploded view of the distal end of the reducer instrument of FIG. 19;

FIG. 21 is a perspective view of the distal end of the reducer instrument of FIG. 19;

FIG. 22 is a perspective view of the distal end of the reducer instrument of FIG. 19 engaged with the anchor assembly of FIG. 15;

FIG. 23 is a perspective view of the reducer instrument of FIG. 19 engaged with the anchor assembly of FIG. 15 during implantation of the vertebral fixation system into a spine;

FIG. 24 is a perspective view of the vertebral fixation system of FIG. 13 fully implanted into the spine;

FIGS. 25 and 26 are perspective views of one example of a vertebral fixation system according to a third embodiment of the present invention;

FIGS. 27 and 28 are plan and perspective views, respectively, of an anchor assembly forming part of the vertebral fixation system of FIG. 25;

FIG. 29 is an exploded view of the anchor assembly of FIG. 27;

FIG. 30 is as perspective view of the head region a bone screw forming part of the anchor assembly of FIG. 27;

FIG. 31 is a plan view of a staple body forming part of the anchor assembly of FIG. 27;

FIG. 32 is a perspective view of the distal end of the reducer instrument of FIG. 7 engaged with the anchor assembly of FIG. 27;

FIG. 33 is a perspective view of the vertebral fixation system of FIG. 25 fully implanted into the spine;

FIGS. 34 and 35 are perspective views of one example of a vertebral fixation system according to a fourth embodiment of the present invention;

FIGS. 36 and 37 are plan and perspective views, respectively, of an anchor assembly forming part of the vertebral fixation system of FIG. 34;

FIG. 38 is an exploded view of the anchor assembly of FIG. 36;

FIG. 39 is as perspective view of the head region a bone screw forming part of the anchor assembly of FIG. 36;

FIG. 40 is a plan view of a staple body forming part of the anchor assembly of FIG. 36;

FIG. 41 is a perspective view of the distal end of the reducer instrument of FIG. 19 engaged with the anchor assembly of FIG. 36;

FIG. 42 is a perspective view of the vertebral fixation system of FIG. 34 fully implanted into the spine;

FIG. 43 is a perspective view of an example of a guide assembly according to one embodiment suitable for use with the vertebral fixation system of FIG. 1;

FIG. 44 is a perspective view of a guide sleeve forming part of the guide assembly of FIG. 43 in the process of mating with a staple body forming part of the vertebral fixation assembly of FIG. 1;

FIG. 45 is a perspective view of the distal end of the guide sleeve of FIG. 44;

FIG. 46 is a perspective view of the staple body of FIG. 44;

FIG. 47 is an exploded plan view of a guide post forming part of the guide assembly of FIG. 43;

FIG. 48 is a perspective view of the distal end of the inner rod forming part of the guide post of FIG. 47;

FIG. 49 is a perspective view of the distal end of an outer sleeve forming part of the guide post of FIG. 47;

FIGS. 50-54 illustrate an example of a reduction tool for use with the vertebral fixation system of FIG. 1 and the guide post of FIG. 47, according to one embodiment;

FIGS. 55-62 illustrate an example of an alternative guide assembly for use with the vertebral fixation system of FIG. 1 and the reduction tool of FIG. 51;

FIG. 63 is an example of an anchor assembly forming part of a vertebral fixation system according to a fifth embodiment of the present invention;

FIGS. 64-68 are perspective views of the vertebral fixation system of FIG. 63 during various sequential steps of implantation onto a spine;

FIG. 69 is a perspective view of the vertebral fixation system of FIG. 63 implanted onto a human spine;

FIGS. 70-71 are plan views of an anchor assembly forming part of a vertebral fixation system according to a sixth embodiment of the present invention;

FIG. 72 is a perspective view of a staple body and bone bolt forming part of the vertebral fixation system of FIG. 70;

FIG. 73 is a perspective view of the staple body and bone bolt of FIG. 72 with a first hinge cap added;

FIG. 74 is a perspective view of a setscrew for use with the staple body and hinge cap of FIG. 73;

FIG. 75 is a perspective view of the staple body and bone bolt of FIG. 73 with the first hinge cap secured with the setscrew of FIG. 74;

FIG. 76 is a perspective view of the staple body and bone bolt of FIG. 75 with a second hinge cap added;

FIG. 77 is a perspective view of the staple body and bone bolt of FIG. 76 with a lock nut added;

FIG. 78 is a perspective view of a bone bolt forming part of the vertebral fixation system of FIG. 70;

FIGS. 79-80 are exploded perspective and perspective views, respectively, of a spinal rod forming part of the vertebral fixation system of FIG. 70;

FIG. 81 is a top plan view of the staple body and bone bolt of FIG. 72 with a spinal rod of FIG. 79;

FIGS. 82-83 are perspective and exploded perspective views, respectively, of an anchor assembly forming part of a vertebral fixation system according to a seventh embodiment of the present invention;

FIGS. 84-85 are perspective and exploded perspective views, respectively, of an anchor assembly forming part of a vertebral fixation system according to an eighth embodiment of the present invention; and FIG. 86 is a perspective view of an anchor assembly forming part of a vertebral fixation system according to a ninth embodiment of the present invention.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The vertebral fixation system and methods described herein boast a variety of inventive features and components that warrant patent protection, both individually and in combination.

This disclosure provides examples of multiple embodiments of a vertebral fixation system. In each case, the vertebral fixation system includes a plurality of anchor assemblies that are implanted in vertebral bodies at multiple adjacent spinal levels, and are connected and stabilized by one or more elongated rods extending between them. Each embodiment is shown by way of example only as a 2-level construct, having a pair of anchor assemblies connected by a rod. However, it should be understood that the vertebral fixation systems described herein are scalable to accommodate any number of spinal levels that need to be stabilized, and thus any particular embodiment may include any number of anchor assemblies connected by an elongated spinal rod (or multiple rod segments) without departing from the scope of the invention. Moreover, although the vertebral fixation systems described herein may be used along any aspect of the spine (e.g. anterior, posterior, antero-lateral, postero-lateral) they are particularly suited for implantation along a lateral aspect of the spine. Additionally, while not shown, the anchor assemblies according to the different embodiments described below may be used together where appropriate (e.g. single rod constructs may be formed with a combination of any of the differing single rod embodiments and dual rod constructs may be used with a combination of any of the differing dual rod constructs).

FIGS. 1-6 illustrate an example of a vertebral fixation system 10 according to a first embodiment of the present invention. The vertebral fixation system 10 generally is a dual screw, single rod construct. The vertebral fixation system 10 includes at least a pair of anchor assemblies 12 connected by a spinal rod 14. Each anchor assembly 12 includes a staple body 16, a pair of bone screws 18, a staple cap 20, an axial clip 22, and a lock nut 24. The staple body 16 of the instant example has a generally elliptical footprint, however other shapes are possible without departing from the scope of the present invention. The staple body 16 includes a first surface 26 and a second surface 28 opposite the first surface 26. The first surface 26 is configured to engage the vertebral body and thus has a generally concave curvature to better fit the generally convex contour of the lateral aspect of the vertebral body. The staple body 16 includes one or more projections 30 extending generally perpendicularly from the first surface 26 to provide purchase for the staple body 16 within the vertebral body. By way of example, the projections 30 are provided as elongated posts that taper to a sharp distal edge 32 that may be impacted into the vertebral body such that upon implantation of the staple body 16 the first surface 26 rests flush against the lateral surface of the vertebral body. Although shown by way of example as four projections 30 distributed around the outside edge of the staple body 16, the projections 30 may be provided in various alternative numbers and/or configurations from that shown (as goes for all the various staple embodiments described hereafter). For example, the projections may be arranged along the interior of the first surface 26. The number of projections 30 may also vary from the four shown to include a single projection or many smaller projections without departing from the scope of the present invention.

By way of example only, the second surface 28 is generally planar, however other configurations are possible. The staple body 16 includes a post 34 extending generally perpendicularly in a proximal direction from the second surface 28. The post 34 includes a threaded region 36 configured to threadedly engage the lock nut 24. The staple body 16 further includes a pair of rod channels 38 formed within the second surface 28 and positioned with one on each side of the post 34. The rod channels 38 are configured to receive either the spinal rod 14 or the projection 66 of the staple cap 20. Within each recess 38 is an aperture 40 configured to receive a bone screw 18 therethrough. The upper portion of the aperture 40 includes a circumferential surface 42 configured to seat the lower surface 54 of the head portion 46 of the bone screw 18. The circumferential surface 42 may be tapered or concave depending upon the configuration of the lower surface 54 of the bone screw 18 (e.g. tapered to accommodate a fixed angle screw and concave to accommodate a variable angle screw). A lip 44 extends generally circumferentially around the edge of the staple body 16, except in the places where the recesses 38 intersect the edge of the staple body 16. The lip 44 is configured to provide an engagement interface for any number of instruments to aid in the implantation procedure, for example an insertion instrument (e.g. the guide assembly 410 of the kind shown and described in relation to FIGS. 43-49) or a single-rod reducer 90 described below.

Each of the bone screws 18 used with the vertebral fixation system 10 are identical. The bone screw 18 includes a head portion 46 and a threaded shaft 48. The head portion 46 includes a top surface 50 having an engagement recess 52 formed therein that is configured to engage with a suitable driver instrument (not shown). The head portion 46 further includes a lower surface 54 extending circumferentially between the top surface 50 and the neck portion 56. The lower surface 54 can be either tapered or convex depending upon whether the bone screw 18 is a fixed angle or a variable angle screw. In the example shown, the bone screw 18 is a fixed angle screw and the lower surface 54 is tapered to the neck portion 56. Upon assembly of the anchor assembly 12, the lower surface 54 is seated within the circumferential surface 42 of the rod channel 38 of the staple body 16. The neck portion 56 is a generally smooth (e.g. non-threaded) surface extending circumferentially around the bone screw 18. The diameter of the neck portion may be varied depending upon whether the screw is a fixed angle or variable angle screw. For example, the bone screw 18 shown is a fixed angle bone screw and therefore the neck portion 56 has a diameter that is substantially the same as the diameter of the aperture 40 of the staple body 16. This prevents angular movement of the bone screw during insertion. However, a variable angle bone screw would have a smaller diameter than that of the aperture 40 to allow for angular movement of the bone screw during insertion.

The staple cap 20 has a footprint that is identical to that of the staple body 16, in the example provided that footprint is elliptical. The staple cap 20 includes a lower surface 58 that mates with the staple body 16, an upper surface 60 opposite the lower surface 58, and an aperture 62 that extends through the center of the staple cap 20 and is dimensioned to receive the post 34 of the staple body 16 therethrough. The lower surface includes a concave recess 64 on one side of the aperture 62 and an elongated protrusion 66 on the other side of the aperture 62. The concave recess 64 is dimensioned to receive at least a portion of the spinal rod 14 and is configured to cooperate with one of the recesses 38 of the staple body 16 to form a channel for the spinal rod 14 to be seated in. The elongated protrusion 66 is configured to be received within the other recess 38 of the staple body 16. Thus, when fully assembled, one rod channel 38 of the staple body 16 will receive a spinal rod 14 therein and the other rod channel 38 of the staple body 16 will receive the elongated protrusion 66 therein. The upper surface 60 includes a circular recess 68 surrounding the aperture 62 and configured to receive the axial clip 22 therein. The circular recess 68 includes a circumferential lip 70 dimensioned to capture the axial clip 22.

The axial clip 22 acts as a washer. The axial clip 22 includes at least one flexible protrusion 72 that is captured under the lip 70 of the circular recess 68. The axial clip 22 further includes a central aperture 74 and a concave surface 76 surrounding the central aperture 74. The concave surface 76 is configured to seat the lock nut 24 therein. Upon assembly, the axial clip 22 resides in the circular recess 68 of the staple cap 20 and the one or more flexible protrusions 72 are captured under lip 70 to keep the clip 22 in place. The clip 22 moves in a spherical manner relative to the lock nut 24 to ensure that the staple cap 20 and spinal rod 14 are loaded axially rather than from the side or at an angle.

The lock nut 24 includes a lower surface 78, a circumferential purchase region 80, and a threaded aperture 82 extending therethrough. The lower surface 78 is convex and is configured to mate with the concave surface 76 of the axial clip 22. The circumferential purchase region 80 includes a plurality of projections and recesses that are designed to mate with an insertion instrument (not shown). The threaded aperture 82 mates with the post 34 of the staple body 16. The lock nut 24 may be spot welded to the axial clip 22 such that the staple cap 20, axial clip 22 and lock nut 24 are held together as a single piece to aid insertion and limit the number of small pieces and steps required to install the device. Once the lock nut 24 is aligned with the post 34 and appropriate torque is applied, the spot welds are broken and the lock nut 24 may be rotated to tighten the construct.

In use, a vertebral fixation procedure is started with the surgeon creating an operative corridor to a surgical target site. This may be accomplished, for example, via a lateral, transpsoas approach, such as that described in commonly owned U.S. Pat. No. 7,905,840, the entire contents of which are incorporated by reference into this disclosure as if set forth fully herein. Next, the staple body 16 is anchored to a lateral aspect of a vertebral body by first impacting the projections 30 into the vertebral body. Next, a pair of bone screws 18 are inserted through the apertures 40 and driven into the vertebral body for purchase. Once the staple body 16 is in place, the spinal rod 14 is inserted into one of the rod channels 38. At this point, the staple cap 20 with attached axial clip 22 and lock nut 24 are applied to the staple body 16 and a single-rod reducer 90 (described below) is employed to provide the necessary compression force on the spinal rod 14. The lock nut 24 is then rotated (e.g. clockwise) to lock the anchor assembly 12 together. The procedure is completed once the desired number of anchor assemblies 12 have been implanted and connected by one or more spinal rods 14. Upon completion of the implantation steps, the surgeon will remove any instrumentation used to maintain the operative corridor and close the surgical wound.

FIGS. 7-9 illustrate an example of a single-rod reducer instrument 90 for use with the vertebral fixation system 10 described above. The single-rod reducer 90 is employed after the spinal rod 14 has been introduced to provide a compressive force on the spinal rod 14 and anchor assembly 12 while it is locked in place. The single-rod reducer 90 described herein may be used with any of the vertebral fixation system embodiments presently described, however it is optimal for use with a single rod construct such as the vertebral fixation system 10 described immediately above. The single-rod reducer 90 includes a front handle 91, back handle 92, upper sliding arm 93, lower stationary arm 94, handle locking base 95, and reduction assembly 96. By way of example only, squeezing the front handle 91, which is pivotally connected to the upper sliding arm 93, causes the upper sliding arm 93 to translate forward relative to the lower stationary arm 94. The teeth provided on the handle locking base 95 allow the user to release the handle, while the front handle 91 remains locked in the position it was released. This allows the user to use additional instruments during the procedure after releasing the handle.

The reduction assembly 96 is located at the distal end of the upper sliding arm 93 and lower stationary arm 94 and includes a rod reducer 97 and a staple holder 98. The rod reducer 97 and staple holder 98 each have a footprint that correlates to the footprint of the staple body 16. Thus in the example provided the rod reducer 97 and staple holder 98 each have an elliptical footprint. The rod reducer 97 includes a connecting slot 99 at a proximal end that is dimensioned to receive the distal end of the upper sliding arm 93. The rod reducer 97 has a generally elliptical aperture 100 extending therethrough dimensioned to receive staple holder 98 therein. The rod reducer 97 translates along the outside of the staple holder 98 to contact the spinal rod 14. The distal end of the rod reducer includes a pair of semi-circular recesses 101 positioned on either side of the rod reducer 97. The semi-circular recesses 101 are dimensioned to receive a portion of the spinal rod 14 during the reduction process.

By way of example, the staple holder 98 is a generally cylindrical body having a generally elliptical hollow lumen 102 extending therethrough and includes a pair of attachment flanges 103 located at a proximal end. The lumen 102 is configured to allow passage of an insertion instrument (not shown) capable of mating with the lock nut 24 to tighten and secure the anchor assembly 12 once rod reduction has occurred. The attachment flanges 103 attach the staple holder 98 to the lower stationary arm 94 while permitting the upper sliding arm 93 (and the rod reducer 97) to translate without resistance from the staple holder 98. The staple holder 98 further includes a pair of opposing elongated slots 104 extending from the distal end in a proximal direction for a length correlating to between one-half and two-thirds of the length of the staple holder 98. The elongated slots 104 are provided with a width that is greater than the width of the spinal rod 14 as the spinal rod 14 will be received within the elongated slots 104 during rod reduction. The elongated slots 104 are positioned in an offset orientation relative to the axial center of the hollow lumen such that the elongated slots 104 will each match up with the rod channel 38 on the staple body 16 when the staple holder 98 is mated with the staple body 16 during use (as shown in FIG. 10). The distal end of the staple holder 98 includes a tapered surface 105 extending from the distal edge of the staple holder 98 partially into the lumen 102 to allow for the staple holder 98 to pass over the lip 44 on the staple body 16. The staple holder 98 further includes a circumferential recess 106 located on the interior of the lumen 102 near the distal end. The circumferential recess 106 is dimensioned to receive the lip 44 of the staple body 16 therein. The positioning of the elongated recesses 104 creates a deflectable portion 107 of the staple holder 98. As the distal end of the lumen 102 passes over the lip 44 of the staple body 16, the deflectable portion 107 deflects slightly outward to allow this passage. When the lip 44 is fully seated within the circumferential recess 106, the deflectable portion 107 "snaps" back into place and the staple holder 98 is temporarily secured to the staple body 16.

The single-rod reducer 90 is put to use once the staple body 16 is anchored to a lateral aspect of a vertebral body with a pair of bone screws 18, and the spinal rod 14 has been inserted into one of the rod channels 38. At this point, the distal end of the single-rod reducer 90 is advanced down the operative corridor and the staple holder 98 is securely engaged to the staple body 16. As mentioned above, this is accomplished by advancing the staple holder 98 over the staple body 16 until the lip 44 is fully seated within the circumferential recess 106. The staple cap 20 with attached axial clip 22 and lock nut 24 are then engaged with an appropriate insertion instrument (not shown) and advanced distally along the operative corridor. The staple cap 20 (with attached axial clip 22 and lock nut 24) is then advanced through the lumen 102 of the staple holder 98 until it contacts the staple body 16. The single-rod reducer 90 is then operated by squeezing the front handle 91, causing the rod reducer 97 to translate forward relative to the staple holder 98. By doing so, the rod reducer 97 presses the rod 14 into position within the recess 38 of the staple body 16. The lock nut 24 is then rotated (e.g. clockwise) to lock the anchor assembly 12 together. The staple holder 98 can be easily disconnected after the staple cap 20 is secured onto the staple body 16 by pulling the reducer 90 proximally away from the anchor assembly 12. As shown in FIG. 11, the single-rod reducer 90 is then applied the anchor assembly being implanted in the adjacent vertebral level. FIG. 12 illustrates the vertebral fixation system 10 in place on a spine after two anchor assemblies 12 and one segment of the spinal rod 14 have been successfully implanted on the spine. Although shown by way of example as a single level fixation, multiple levels are possible, with one or more spinal rods 14 being employed to link the anchor assemblies 12 together.

FIGS. 13-18 illustrate an example of a vertebral fixation system 110 according to a second embodiment of the present invention. The vertebral fixation system 110 generally is a dual screw, dual rod construct. The vertebral fixation system 110 includes at least a pair of anchor assemblies 112 connected by a pair of spinal rods 114. Each anchor assembly 112 includes a staple body 116, a pair of bone screws 118, a staple cap 120, an axial clip 122, and a lock nut 124. The staple body 116 of the instant example has a generally elliptical footprint, however other shapes are possible without departing from the scope of the present invention. The staple body 116 includes a first surface 126 and a second surface 128 opposite the first surface 126. The first surface 126 is configured to engage the vertebral body and thus has a generally concave curvature to better fit the generally convex contour of the lateral aspect of the vertebral body. The staple body 116 includes one or more projections 130 extending generally perpendicularly from the first surface 126 to provide purchase for the staple body 116 within the vertebral body. By way of example, the projections 130 are provided as elongated posts that taper to a sharp distal edge 132 that may be impacted into the vertebral body such that upon implantation of the staple body 116 the first surface 126 rests flush against the lateral surface of the vertebral body. Although shown by way of example as four projections 130 distributed around the outside edge of the staple body 116, the projections 130 may be provided in various alternative numbers and/or configurations from that shown (as goes for all the various staple embodiments described hereafter). For example, the projections may be arranged along the interior of the first surface 126. The number of projections 130 may also vary from the four shown to include a single projection or many smaller projections without departing from the scope of the present invention.

By way of example only, the second surface 128 is generally planar, however other configurations are possible. The staple body 116 includes a post 134 extending generally perpendicularly in a proximal direction from the second surface 128. The post 134 includes a threaded region 136 configured to threadedly engage the lock nut 124. The staple body 116 further includes a pair of rod channels 138 formed within the second surface 128 and positioned with one on each side of the post 134. The rod channels 138 are configured to receive a spinal rod 114. Within each rod channel 138 is an aperture 140 configured to receive a bone screw 118 therethrough. The upper portion of the aperture 140 includes a circumferential surface 142 configured to seat the lower surface 154 of the head portion 146 of the bone screw 118. The circumferential surface 142 may be tapered or concave depending upon the configuration of the lower surface 154 of the bone screw 118 (e.g. tapered to accommodate a fixed angle screw and concave to accommodate a variable angle screw). A lip 144 extends generally circumferentially around the edge of the staple body 116, except in the places where the rod channels 138 intersect the edge of the staple body 116. The lip 144 is configured to provide an engagement interface for any number of instruments to aid in the implantation procedure, for example an insertion instrument (e.g. the guide assembly 410 of the kind shown and described in relation to FIGS. 43-49) or a dual-rod reducer 190 described below.

Each of the bone screws 118 used with the vertebral fixation system 110 are identical. The bone screw 118 includes a head portion 146 and a threaded shaft 148. The head portion 146 includes a top surface 150 having an engagement recess 152 formed therein that is configured to engage with a suitable driver instrument (not shown). The head portion 146 further includes a lower surface 154 extending circumferentially between the top surface 150 and the neck portion 156. The lower surface 154 can be either tapered or convex depending upon whether the bone screw 118 is a fixed angle or a variable angle screw. In the example shown, the bone screw 118 is a fixed angle screw and the lower surface 154 is tapered to the neck portion 156. Upon assembly of the anchor assembly 112, the lower surface 154 is seated within the circumferential surface 142 of the rod channel 138 of the staple body 116. The neck portion 156 is a generally smooth (e.g. non-threaded) surface extending circumferentially around the bone screw 118. The diameter of the neck portion may be varied depending upon whether the screw is a fixed angle or variable angle screw. For example, the bone screw 118 shown is a fixed angle bone screw and therefore the neck portion 156 has a diameter that is substantially the same as the diameter of the aperture 140 of the staple body 116. This prevents angular movement of the bone screw during insertion. However, a variable angle bone screw would have a smaller diameter than that of the aperture 140 to allow for angular movement of the bone screw during insertion.

The staple cap 120 has a footprint that is identical to that of the staple body 116, in the example provided that footprint is elliptical. The staple cap 120 includes a lower surface 158 that mates with the staple body 116, an upper surface 160 opposite the lower surface 158, and an aperture 162 that extends through the center of the staple cap 120 and is dimensioned to receive the post 134 of the staple body 116 therethrough. The lower surface 158 includes a pair of concave recesses 164, with one concave recess 164 positioned on each side of the aperture 162. The concave recesses 164 are each dimensioned to receive at least a portion of a spinal rod 114 and are configured to cooperate with the rod channels 138 of the staple body 116 to form a pair of channels for the spinal rods 114 to be seated in. Thus, when fully assembled, both rod channels 138 of the staple body 116 will receive a spinal rod 114 therein. The upper surface 160 includes a circular recess 168 surrounding the aperture 162 and configured to receive the axial clip 122 therein. The circular recess 168 includes a circumferential lip 170 dimensioned to capture the axial clip 122.

The axial clip 122 acts as a washer. The axial clip 122 includes at least one flexible protrusion 172 that is captured under the lip 170 of the circular recess 168. The axial clip 122 further includes a central aperture 174 and a concave surface 176 surrounding the central aperture 174. The concave surface 176 is configured to seat the lock nut 124 therein. Upon assembly, the axial clip 122 resides in the circular recess 168 of the staple cap 120 and the one or more flexible protrusions 172 are captured under lip 170 to keep the clip 122 in place. The clip 122 moves in a spherical manner relative to the lock nut 124 to ensure that the staple cap 120 and spinal rods 114 are loaded axially rather than from the side or at an angle.

The lock nut 124 includes a lower surface 178, a circumferential purchase region 180, and a threaded aperture 182 extending therethrough. The lower surface 178 is convex and is configured to mate with the concave surface 176 of the axial clip 122. The circumferential purchase region 180 includes a plurality of projections and recesses that are designed to mate with an insertion instrument (not shown). The threaded aperture 182 mates with the post 134 of the staple body 116. The lock nut 124 may be spot welded to the axial clip 122 such that the staple cap 120, axial clip 122 and lock nut 124 are held together as a single piece to aid insertion and limit the number of small pieces and steps required to install the device. Once the lock nut 124 is aligned with the post 134 and appropriate torque is applied, the spot welds are broken and the lock nut 124 may be rotated to tighten the construct.

In use, a vertebral fixation procedure is started with the surgeon creating an operative corridor to a surgical target site. This may be accomplished, for example, via a lateral, transpsoas approach, such as that described in the above-referenced '840 patent (incorporated by reference). Next, the staple body 116 is anchored to a lateral aspect of a vertebral body by first impacting the projections 130 into the vertebral body. Next, a pair of bone screws 118 are inserted through the apertures 140 and driven into the vertebral body for purchase. Once the staple body 116 is in place, the spinal rods 114 are inserted into each of the rod channels 138. At this point, the staple cap 120 with attached axial clip 122 and lock nut 124 are applied to the staple body 116 and a dual-rod reducer 190 (described below) is employed to provide the necessary compression force on the spinal rods 114. The lock nut 124 is then rotated (e.g. clockwise) to lock the anchor assembly 112 together. The procedure is completed once the desired number of anchor assemblies 112 have been implanted and connected by spinal rods 114. Upon completion of the implantation steps, the surgeon will remove any instrumentation used to maintain the operative corridor and close the surgical wound.

FIGS. 19-21 illustrate an example of a dual-rod reducer 190 for use with the vertebral fixation system 110 described above. The dual-rod reducer 190 is employed after the spinal rods 114 have been introduced to provide a compressive force on the spinal rods 114 and anchor assembly 112 while it is locked in place. The dual-rod reducer 190 described herein may be used with any of the vertebral fixation system embodiments presently described, however it is optimal for use with a dual rod construct such as the vertebral fixation system 110 described immediately above. The dual-rod reducer 190 includes a front handle 191, back handle 192, upper sliding arm 193, lower stationary arm 194, handle locking base 195, and reduction assembly 196. By way of example only, squeezing the front handle 191, which is pivotally connected to the upper sliding arm 193, causes the upper sliding arm 193 to translate forward relative to the lower stationary arm 194. The teeth provided on the handle locking base 195 allow the user to release the handle, while the front handle 191 remains locked in the position it was released. This allows the user to use additional instruments during the procedure after releasing the handle.

The reduction assembly 196 is located at the distal end of the upper sliding arm 193 and lower stationary arm 194 and includes a rod reducer 197 and a staple holder 198. The rod reducer 197 and staple holder 198 each have a footprint that correlates to the footprint of the staple body 116. Thus in the example provided the rod reducer 197 and staple holder 198 each have an elliptical footprint. The rod reducer 197 includes a connecting slot 199 at a proximal end that is dimensioned to receive the distal end of the upper sliding arm 193. The rod reducer 197 has a generally elliptical aperture 200 extending therethrough dimensioned to receive staple holder 198 therein. The rod reducer 197 translates along the outside of the staple holder 198 to contact the spinal rods 114. The distal end of the rod reducer includes two pair of semi-circular recesses 201 positioned on either side of the rod reducer 197. The semi-circular recesses 201 are dimensioned to receive a portion of the spinal rods 114 during the reduction process.

By way of example, the staple holder 198 is a generally cylindrical body having a generally elliptical hollow lumen 202 extending therethrough and includes a pair of attachment flanges 203 located at a proximal end. The lumen 202 is configured to allow passage of an insertion instrument (not shown) capable of mating with the lock nut 124 to tighten and secure the anchor assembly 112 once rod reduction has occurred. The attachment flanges 203 attach the staple holder 198 to the lower stationary arm 194 while permitting the upper sliding arm 193 (and the rod reducer 197) to translate without resistance from the staple holder 198. The staple holder 198 further includes two pair of opposing elongated slots 204 extending from the distal end in a proximal direction for a length correlating to between one-half and two-thirds of the length of the staple holder 198. The elongated slots 204 are provided with a width that is greater than the width of the spinal rods 114 as the spinal rod 114 will be received within the elongated slots 204 during rod reduction. The elongated slots 204 are positioned in an offset orientation relative to the axial center of the hollow lumen such that the elongated slots 204 will each match up with the rod channels 138 on the staple body 116 when the staple holder 198 is mated with the staple body 116 during use (as shown in FIG. 22). The distal end of the staple holder 198 includes a tapered surface 205 extending from the distal edge of the staple holder 198 partially into the lumen 202 to allow for the staple holder 198 to pass over the lip 144 on the staple body 116. The staple holder 198 further includes a circumferential recess 206 located on the interior of the lumen 202 near the distal end. The circumferential recess 206 is dimensioned to receive the lip 144 of the staple body 116 therein. The positioning of the elongated recesses 204 creates a pair of deflectable portions 207 of the staple holder 198. As the distal end of the lumen 202 passes over the lip 144 of the staple body 116, the deflectable portions 207 deflect slightly outward to allow this passage. When the lip 144 is fully seated within the circumferential recess 206, the deflectable portions 207 "snap" back into place and the staple holder 198 is temporarily secured to the staple body 116.

The dual-rod reducer 190 is put to use once the staple body 116 is anchored to a lateral aspect of a vertebral body with a pair of bone screws 118, and the spinal rods 114 have been inserted into the rod channels 138. At this point, the distal end of the dual-rod reducer 190 is advanced down the operative corridor and the staple holder 198 is securely engaged to the staple body 116. As mentioned above, this is accomplished by advancing the staple holder 198 over the staple body 116 until the lip 144 is fully seated within the circumferential recess 206. The staple cap 120 with attached axial clip 122 and lock nut 124 are then engaged with an appropriate insertion instrument (not shown) and advanced distally along the operative corridor. The staple cap 120 (with attached axial clip 122 and lock nut 124) is then advanced through the lumen 202 of the staple holder 198 until it contacts the staple body 116. The dual-rod reducer 190 is then operated by squeezing the front handle 191, causing the rod reducer 197 to translate forward relative to the staple holder 198. By doing so, the rod reducer 197 presses the rods 114 into position within the recesses 138 of the staple body 116. The lock nut 124 is then rotated (e.g. clockwise) to lock the anchor assembly 112 together. The staple holder 198 can be easily disconnected after the staple cap 120 is secured onto the staple body 116 by pulling the dual-rod reducer 190 proximally away from the anchor assembly 112. As shown in FIG. 23, the reducer 190 is then applied the anchor assembly 112 being implanted in the adjacent vertebral level. FIG. 24 illustrates the vertebral fixation system 110 in place on a spine after two anchor assemblies 110 and one segment of the spinal rod 114 has been successfully implanted on the spine. Although shown by way of example as a single level fixation, multiple levels are possible, with two or more spinal rods 114 being employed to link the anchor assemblies 112 together.

FIGS. 25-31 illustrate an example of a vertebral fixation system 210 according to a third embodiment of the present invention. The vertebral fixation system 210 generally is a single screw, single rod construct. The vertebral fixation system 210 includes at least a pair of anchor assemblies 212 connected by a spinal rod 214. Each anchor assembly 212 includes a staple body 216, a bone bolt 218, a split ring 219, a staple cap 220, an axial clip 222, and a lock nut 224. The staple body 216 of the instant example has a generally elliptical footprint, however other shapes are possible without departing from the scope of the present invention. The staple body 216 includes a first surface 226 and a second surface 228 opposite the first surface 226. The first surface 226 is configured to engage the vertebral body and thus has a generally concave curvature to better fit the generally convex contour of the lateral aspect of the vertebral body. The staple body 216 includes one or more projections 230 extending generally perpendicularly from the first surface 226 to provide purchase for the staple body 216 within the vertebral body. By way of example, the projections 230 are provided as elongated posts that taper to a sharp distal edge 232 that may be impacted into the vertebral body such that upon implantation of the staple body 216 the first surface 226 rests flush against the lateral surface of the vertebral body. Although shown by way of example as two projections 230 positioned on opposite sides of the staple body 216, the projections 230 may be provided in various alternative numbers and/or configurations from that shown (as goes for all the various staple embodiments described hereafter). For example, the projections may be arranged along the interior of the first surface 226. The number of projections 230 may also vary from the two shown to include a single projection or many smaller projections without departing from the scope of the present invention. The first surface 226 further includes a recess (not shown) for housing the split ring 219.

By way of example only, the second surface 228 is generally planar, however other configurations are possible. The staple body 216 includes an aperture 234 extending axially therethrough and configured to allow passage of the threaded post 254 of the bone bolt 218 therethrough. The staple body 216 further includes a rod channel 238 formed within the second surface 228 and positioned on one side of the aperture 234. The rod channel 238 is configured to receive at least a portion of the spinal rod 214. A lip 244 extends generally circumferentially around the edge of the staple body 216, except for example in the places where the rod channel 238 intersects the edge of the staple body 216. The lip 244 is configured to provide an engagement interface for any number of instruments to aid in the implantation procedure, for example an insertion instrument (e.g. the guide assembly 410 of the kind shown and described in relation to FIGS. 43-49) or a single-rod reducer 90 described above.

The bone bolt 218 includes a head portion 246 and a threaded shaft 248. The head portion 246 (shown in detail in FIG. 30) includes a top surface 250 having an engagement recess 252 formed therein that is configured to engage with a suitable driver instrument (not shown). The head portion 246 further includes a threaded post 254 dimensioned to engage with the lock nut 224. The neck portion 256 is a generally smooth (e.g. non-threaded) slightly convex surface extending circumferentially around the bone bolt 218. The largest diameter of the neck portion 256 is such that the aperture 234 of the staple body 216 and split ring 219 will allow passage therethrough. A circumferential groove 257 is positioned between the neck portion 256 and the threaded shaft 246 and is dimensioned to seat the split ring 219 when the bolt 218 is fully engaged to the staple body 216. Alternatively, the split ring 219 may be initially provided on the in the groove 257 and staple body 216 may be snapped onto the split ring 219 during implantation to secure the staple body 216 onto the bone bolt 218.

The staple cap 220 has a footprint that is identical to that of the staple body 216, in the example provided that footprint is elliptical. The staple cap 220 includes a lower surface 258 that mates with the staple body 216, an upper surface 260 opposite the lower surface 258, and an aperture 262 that extends through the center of the staple cap 220 and is dimensioned to receive the threaded post 254 of the bone bolt 218 therethrough. The lower surface 258 includes a concave recess 264 on one side of the aperture 262 that is dimensioned to receive at least a portion of the spinal rod 214 and is configured to cooperate with the rod channel 238 of the staple body 216 to form a channel for the spinal rod 214 to be seated in. The upper surface 260 includes a circular recess 268 surrounding the aperture 262 and configured to receive the axial clip 222 therein. The circular recess 268 includes a circumferential lip 270 dimensioned to capture the axial clip 222.

The axial clip 222 acts as a washer. The axial clip 222 includes at least one flexible protrusion 272 that is captured under the lip 270 of the circular recess 268. The axial clip 222 further includes a central aperture 274 and a concave surface 276 surrounding the central aperture 274. The concave surface 276 is configured to seat the lock nut 224 therein. Upon assembly, the axial clip 222 resides in the circular recess 268 of the staple cap 220 and the one or more flexible protrusions 272 are captured under lip 270 to keep the clip 222 in place. The clip 222 moves in a spherical manner relative to the lock nut 224 to ensure that the staple cap 220 and spinal rod 214 are loaded axially rather than from the side or at an angle.

The lock nut 224 includes a lower surface 278, a circumferential purchase region 280, and a threaded aperture 282 extending therethrough. The lower surface 278 is convex and is configured to mate with the concave surface 276 of the axial clip 222. The circumferential purchase region 280 includes a plurality of projections and recesses that are designed to mate with an insertion instrument (not shown). The threaded aperture 282 mates with the threaded post 254 of the bone bolt 218. The lock nut 224 may be spot welded to the axial clip 222 such that the staple cap 220, axial clip 222 and lock nut 224 are held together as a single piece to aid insertion and limit the number of small pieces and steps required to install the device. Once the lock nut 224 is aligned with the threaded post 254 and appropriate torque is applied, the spot welds are broken and the lock nut 224 may be rotated to tighten the construct.

In use, a vertebral fixation procedure is started with the surgeon creating an operative corridor to a surgical target site. This may be accomplished, for example, via a lateral, transpsoas approach, such as that described in the above-referenced '840 patent (incorporated by reference). Next, the bone bolt 218 is driven into the vertebral body at a desired location. The staple body 216 (with snap ring 219 attached) is then inserted such that the threaded post 254 of the bone bolt 218 is passed through the aperture 234 and the snap ring 219 resides within the groove 257 of the bone bolt 218. The staple body 216 is anchored to a lateral aspect of a vertebral body by impacting the projections 230 into the vertebral body. Once the staple body 216 is in place, the spinal rod 214 is inserted into the rod channel 238. At this point, the staple cap 220 with attached axial clip 222 and lock nut 224 are applied to the staple body 216 and a reducer instrument 90 (described above) is employed to provide the necessary compression force on the spinal rod 214. The lock nut 224 is then rotated (e.g. clockwise) to lock the anchor assembly 212 together. The procedure is completed once the desired number of anchor assemblies 212 have been implanted and connected by one or more spinal rods 214. Upon completion of the implantation steps, the surgeon will remove any instrumentation used to maintain the operative corridor and close the surgical wound.

The vertebral fixation system 210 described herein is suitable for use with the single-rod reducer 90 described above (with reference to FIGS. 7-9) and therefore a repeat discussion of the features of the single-rod reducer 90 is unnecessary. FIG. 32 illustrates the reduction assembly 96, including the rod reducer 97 and staple holder 98 engaged with an anchor assembly 212 of the present embodiment. The reducer 90 is put to use once the bone bolt 218 and staple body 216 are anchored to a lateral aspect of a vertebral body, and the spinal rod 214 has been inserted into the rod channel 238. At this point, the distal end of the reducer 90 is advanced down the operative corridor and the staple holder 98 is securely engaged to the staple body 216. This is accomplished by advancing the staple holder 98 over the staple body 216 until the lip 244 is fully seated within the circumferential recess 106. The staple cap 220 with attached axial clip 222 and lock nut 224 are then engaged with an appropriate insertion instrument (not shown) and advanced distally along the operative corridor. The staple cap 220 (with attached axial clip 222 and lock nut 224) is then advanced through the lumen 102 of the staple holder 98 until it contacts the staple body 216. The reducer 90 is then operated by squeezing the front handle 91, causing the rod reducer 97 to translate forward relative to the staple holder 98. By doing so, the rod reducer 97 presses the rod 214 into position within the rod channel 238 of the staple body 216. The lock nut 224 is then rotated (e.g. clockwise) to lock the anchor assembly 212 together. The staple holder 98 can be easily disconnected after the staple cap 220 is secured onto the staple body 216 by pulling the reducer 90 proximally away from the anchor assembly 212. FIG. 33 illustrates the vertebral fixation system 210 in place on a spine after two anchor assemblies 212 and one segment of the spinal rod 214 have been successfully implanted on the spine. Although shown by way of example as a single level fixation, multiple levels are possible, with one or more spinal rods 214 being employed to link the anchor assemblies 212 together.

FIGS. 34-40 illustrate an example of a vertebral fixation system 310 according to a fourth embodiment of the present invention. The vertebral fixation system 310 generally is a single screw, dual rod construct. The vertebral fixation system 310 includes at least a pair of anchor assemblies 312 connected by a spinal rod 314. Each anchor assembly 312 includes a staple body 216, a bone bolt 218, a split ring 219, a staple cap 220, an axial clip 222, and a lock nut 224. The staple body 316 of the instant example has a generally elliptical footprint, however other shapes are possible without departing from the scope of the present invention. The staple body 316 includes a first surface 326 and a second surface 328 opposite the first surface 326. The first surface 326 is configured to engage the vertebral body and thus has a generally concave curvature to better fit the generally convex contour of the lateral aspect of the vertebral body. The staple body 316 includes one or more projections 330 extending generally perpendicularly from the first surface 326 to provide purchase for the staple body 316 within the vertebral body. By way of example, the projections 330 are provided as elongated posts that taper to a sharp distal edge 332 that may be impacted into the vertebral body such that upon implantation of the staple body 316 the first surface 326 rests flush against the lateral surface of the vertebral body. Although shown by way of example as two projections 330 positioned on opposite sides of the staple body 316, the projections 330 may be provided in various alternative numbers and/or configurations from that shown (as goes for all the various staple embodiments described hereafter). The first surface 326 further includes a recess (not shown) for housing the split ring 319.

By way of example only, the second surface 328 is generally planar, however other configurations are possible. The staple body 316 includes an aperture 334 extending axially therethrough and configured to allow passage of the threaded post 354 of the bone bolt 318 therethrough. The staple body 316 further includes a pair of rod channels 338 formed within the second surface 328 and positioned with one on either side of the aperture 334. The rod channels 338 are each configured to receive at least a portion of the spinal rods 314. A lip 344 extends generally circumferentially around the edge of the staple body 316, except for example in the places where the rod channels 338 intersect the edge of the staple body 316.

The lip 344 is configured to provide an engagement interface for any number of instruments to aid in the implantation procedure, for example an insertion instrument (e.g. the guide assembly 410 of the kind shown and described in relation to FIGS. 43-49) or a dual-rod reducer 190 described above.

The bone bolt 318 includes a head portion 346 and a threaded shaft 348. The head portion 346 (shown in detail in FIG. 39) includes a top surface 350 having an engagement recess 352 formed therein that is configured to engage with a suitable driver instrument (not shown). The head portion 346 further includes a threaded post 354 dimensioned to engage with the lock nut 324. The neck portion 356 is a generally smooth (e.g. non-threaded) slightly convex surface extending circumferentially around the bone bolt 318. The largest diameter of the neck portion 356 is such that the aperture 334 of the staple body 316 and split ring 319 will allow passage therethrough. A circumferential groove 357 is positioned between the neck portion 356 and the threaded shaft 346 and is dimensioned to seat the split ring 319 when the bolt 318 is fully engaged to the staple body 316. Alternatively, the split ring 319 may be initially provided on the in the groove 357 and staple body 316 may be snapped onto the split ring 319 during implantation to secure the staple body 316 onto the bone bolt 318.

The staple cap 320 has a footprint that is identical to that of the staple body 316, in the example provided that footprint is elliptical. The staple cap 320 includes a lower surface 358 that mates with the staple body 316, an upper surface 360 opposite the lower surface 358, and an aperture 362 that extends through the center of the staple cap 320 and is dimensioned to receive the threaded post 354 of the bone bolt 318 therethrough. The lower surface 358 includes a pair of concave recesses 364 positioned with one on either side of the aperture 362. The concave recesses 364 are each dimensioned to receive at least a portion of one of the spinal rods 314 and are configured to cooperate with the rod channels 338 of the staple body 316 to form a pair of channels for the spinal rods 314 to be seated in. The upper surface 360 includes a circular recess 368 surrounding the aperture 362 and configured to receive the axial clip 322 therein. The circular recess 368 includes a circumferential lip 370 dimensioned to capture the axial clip 322.

The axial clip 322 acts as a washer. The axial clip 322 includes at least one flexible protrusion 372 that is captured under the lip 370 of the circular recess 368. The axial clip 322 further includes a central aperture 374 and a concave surface 376 surrounding the central aperture 374. The concave surface 376 is configured to seat the lock nut 324 therein. Upon assembly, the axial clip 322 resides in the circular recess 368 of the staple cap 320 and the one or more flexible protrusions 372 are captured under lip 370 to keep the clip 322 in place. The clip 322 moves in a spherical manner relative to the lock nut 324 to ensure that the staple cap 320 and spinal rod 314 are loaded axially rather than from the side or at an angle.

The lock nut 324 includes a lower surface 378, a circumferential purchase region 380, and a threaded aperture 382 extending therethrough. The lower surface 378 is convex and is configured to mate with the concave surface 376 of the axial clip 322. The circumferential purchase region 380 includes a plurality of projections and recesses that are designed to mate with an insertion instrument (not shown). The threaded aperture 382 mates with the threaded post 354 of the bone bolt 318. The lock nut 324 may be spot welded to the axial clip 322 such that the staple cap 320, axial clip 322 and lock nut 324 are held together as a single piece to aid insertion and limit the number of small pieces and steps required to install the device. Once the lock nut 324 is aligned with the threaded post 354 and appropriate torque is applied, the spot welds are broken and the lock nut 324 may be rotated to tighten the construct.

In use, a vertebral fixation procedure is started with the surgeon creating an operative corridor to a surgical target site. This may be accomplished, for example, via a lateral, transpsoas approach, such as that described in the above-referenced '840 patent (incorporated by reference). Next, the bone bolt 318 is driven into the vertebral body at a desired location. The staple body 316 (with snap ring 319 attached) is then inserted such that the threaded post 354 of the bone bolt 318 is passed through the aperture 334 and the snap ring 319 resides within the groove 357 of the bone bolt 318. The staple body 316 is anchored to a lateral aspect of a vertebral body by impacting the projections 330 into the vertebral body. Once the staple body 316 is in place, the spinal rods 314 are inserted into the rod channels 338. At this point, the staple cap 320 with attached axial clip 322 and lock nut 324 are applied to the staple body 316 and a reducer instrument 190 (described above) is employed to provide the necessary compression force on the spinal rod 314. The lock nut 324 is then rotated (e.g. clockwise) to lock the anchor assembly 312 together. The procedure is completed once the desired number of anchor assemblies 312 have been implanted and connected by one or more spinal rods 314. Upon completion of the implantation steps, the surgeon will remove any instrumentation used to maintain the operative corridor and close the surgical wound.

The vertebral fixation system 310 described herein is suitable for use with the dual-rod reducer 190 described above (with reference to FIGS. 19-21) and therefore a repeat discussion of the features of the dual-rod reducer 190 is unnecessary. FIG. 41 illustrates the reduction assembly 196, including the rod reducer 197 and staple holder 198 engaged with an anchor assembly 312 of the present embodiment. The dual-rod reducer 190 is put to use once the bone bolt 318 and staple body 316 are anchored to a lateral aspect of a vertebral body, and the spinal rods 314 have been inserted into the rod channels 338. At this point, the distal end of the reducer 190 is advanced down the operative corridor and the staple holder 198 is securely engaged to the staple body 316. This is accomplished by advancing the staple holder 198 over the staple body 316 until the lip 344 is fully seated within the circumferential recess 206. The staple cap 320 with attached axial clip 322 and lock nut 324 are then engaged with an appropriate insertion instrument (not shown) and advanced distally along the operative corridor. The staple cap 320 (with attached axial clip 322 and lock nut 324) is then advanced through the lumen 202 of the staple holder 198 until it contacts the staple body 316. The dual-rod reducer 190 is then operated by squeezing the front handle 191, causing the rod reducer 197 to translate forward relative to the staple holder 198. By doing so, the rod reducer 197 presses the rods 314 into position within the rod channels 338 of the staple body 316. The lock nut 324 is then rotated (e.g. clockwise) to lock the anchor assembly 312 together. The staple holder 198 can be easily disconnected after the staple cap 320 is secured onto the staple body 316 by pulling the reducer 190 proximally away from the anchor assembly 312. FIG. 42 illustrates the vertebral fixation system 310 in place on a spine after two anchor assemblies 312 and two segments of the spinal rod 314 have been successfully implanted on the spine. Although shown by way of example as a single level fixation, multiple levels are possible, with two or more spinal rods 314 being employed to link the anchor assemblies 312 together.

While specific embodiments have been shown by way of example in the drawings and described herein in detail, it will be appreciated that the invention is susceptible to various modifications and alternative forms. For example, FIGS. 43-49 illustrate the use of an example of a guide assembly 450 including a pair of guide sleeves 452 and a guide post 454. Although shown by way of example only with a vertebral fixation system 400 configured as a dual screw, single rod embodiment, any of the embodiments described above may be modified to utilize the guide assembly 450. By way of example, the vertebral fixation system 400 includes an anchor assembly 402 and at least one spinal rod 404. The anchor assembly includes a stable body 406, a pair of bone screws 408, and a staple cap 410. The staple body 406 includes a pair of rod channels 414, a threaded post 416, and a pair of bone screw apertures 418 situated within the rod channels 414. The structure and function of these specific features are similar to those disclosed with the various examples above and will not be repeated here. The staple body 406 differs from those described above in that it includes a pair of engagement features 420 that are configured to engage with the guide sleeves 452. By way of example, the engagement features 420 are each provided as a pair of recesses 422 that are configured to mate with a pair of hooks 456 positioned at the distal end of the guide sleeves 452. Tab holes 424 are also provided on the outside of the engagement features 420 to provide a positive engagement with a deflectable tab 458 on the guide sleeves 452.

The guide sleeves 452 have a generally concave inner surface 453 to help conform to the shape of the staple body 406. A pair of hooks 456 are provided at the distal end of each guide sleeve 452 to mate with the engagement features 420 of the staple body 406. A deflectable tab 458 is also provided that engages with the tab hole 424 on the staple body 406. The guide sleeves 452 may be positively engaged to the staple body 406 (and inserted with the staple body 406 or inserted after the staple body 406 and subsequently engaged). The positive engagement is created when the hooks 456 slidably engage the engagement features 420 on the staple body 406 and the deflectable tab 458 is seated within the tab hole 424. After the staple body 406 is secured onto the vertebra, pulling on the guide sleeve 452 with force will disengage it from the staple body 406. Together with the guide post 454, the guide sleeves 452 form two passageways 460 to help align the spinal rods 404 within the rod channels during insertion.

FIGS. 47-49 illustrate the guide post 454 in greater detail. The guide post 454 includes an outer tube 462 and an inner rod 464. The outer tube 462 has a shaped distal end 466 that connects to the correspondingly-shaped socket 426 on the threaded post 416 of the staple body 406. The outer tube 462 further includes a lumen 468 extending axially through the entire length of the outer tube 462. The inner rod 464 is received within the lumen 468 of the outer tube 462 and has a threaded distal end 470 that mates with the female threaded socket 428 on the threaded post 416 of the staple body 406. This locks the outer tube 462 in place because the proximal end 472 of the inner rod 464 is at least the same diameter as the outer tube 462, preventing the outer tube 462 from "backing out." The staple cap 410 can then be easily placed into position by sliding the cap 410 down the guide post 454, with the guide post 454 being inside the center hole (not shown) of the staple cap 410. The guide sleeves 452 assist in keeping the staple cap 410 in place while sliding it into position. The guide sleeves 452 further assist in preventing facile tissue creep (e.g. lungs, diaphragm, retroperitoneum, etc. . . . ) when the system is used without an additional tissue retractor. The guide sleeves 452 may be made of plastic (e.g. PEEK, etc. . . . ), metal (e.g. titanium, stainless steel, etc. . . . ), or a combination. The guide sleeves 452 maybe disposable or sterilizable and reusable, or, a portion of the guide sleeve may be sterilizable and reusable and a portion of the guide sleeve 452 may be disposable and the two parts may be removably associated. The guide sleeves generally rigid or they may be flexible. Additionally the guide sleeves may be made out of a shape memory material (e.g. nitinol), such that they are bendable but reusable. At normal temperatures the guide sleeves 452 are bendable. Thus the guide sleeves 452 may be positioned as desired and then bent out of the way to provide better visualization, access, and help to keep tissue from creeping into the staple construct. After use, the guide sleeves 452 may be heated to return them to their original position for reuse.

FIGS. 50-55 illustrate an example of a reducer 510 according to an alternative embodiment of the present invention for use with the vertebral fixation systems shown herein. The reducer 510 is shown and described by way of example only in conjunction with a vertebral fixation system 400 and guide post 454 as described above. However, it should be understood that the reducer 510 is suitable for use with any of the vertebral fixation systems shown by way of example above. By way of example only, the reducer 510 includes an outer tube 512, an elongated inner member 514, and an A/O reducer 516. The outer tube 512 has a distal end 518 and a proximal end 522, with the distal end 518 including at least one arm 520 configured to interface with the spinal rod 404 during the reduction process. The proximal end 522 includes a housing member 524 that allows access to the proximal thumbwheel 528 of the inner member 514 and also an aperture (not shown) located on top of the housing for receiving the distal connector 530 of the A/O reducer 516. The inner member 514 includes a distal engagement end 526 dimensioned to engage a lock nut 412, a proximal thumbwheel 528, and an elongated shaft (not shown) extending between the distal engagement end 526 and proximal thumbwheel 528. The proximal thumbwheel 528 is accessible by a user through the housing 524 of the outer tube 512. The A/O reducer 516 has a distal connector 530 to facilitate attachment to the outer tube 512, a knob 532, and a threaded shaft 534 upon which the knob 532 translates.

Figure 52:
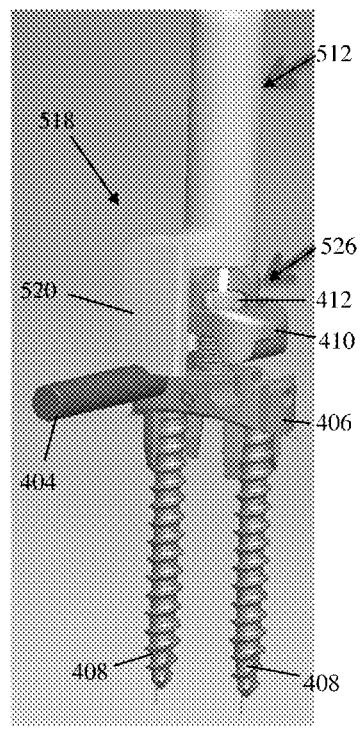
Figure 53:
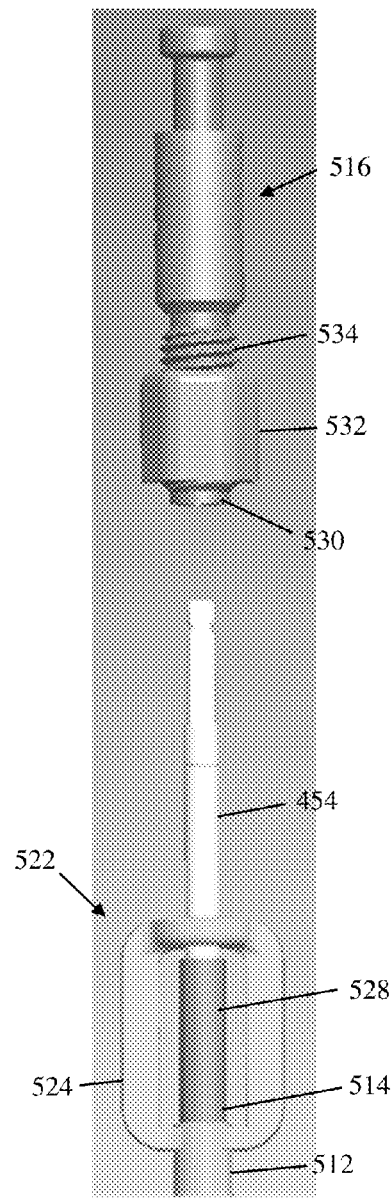
Figure 54:
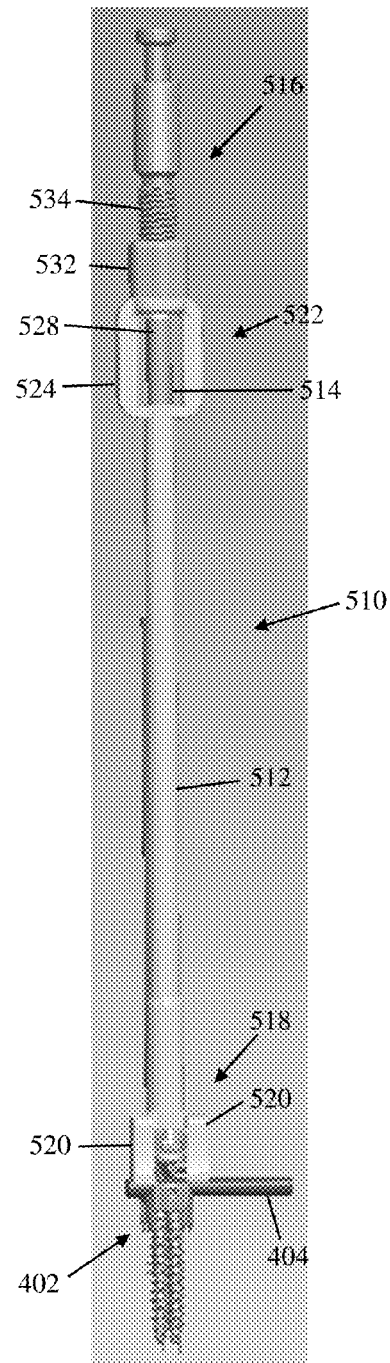

To use the reducer 510, the first step is to implant the staple body 406 and bone screws 408 in a desired location on the vertebral body as described above. Once the staple body 406 and bone screws 408 are in place, the guide post 454 may be attached as described above (and shown in FIG. 50). The spinal rod 404 is then placed within the staple body 406. The reducer 510 is then provided with an attached staple cap 410. As described above in relation to previous embodiments, the staple cap 410 may be provided with the lock nut 412 (and axial clip, which is present but not shown in this embodiment) spot welded onto the staple cap 410 such that when the lock nut 412 is preloaded onto the reducer 510 (via the distal engagement end 526), the staple cap 410 comes with it. In this manner, the staple cap 410 is preloaded onto the reducer 510. The reducer 510 with attached staple cap 410 is then advanced along the guide post 454 until the arm(s) 520 engage the spinal rod 404 (FIGS. 51 & 52). At this point the A/O reducer 516 is attached to the proximal end of the outer tube 512 (FIGS. 53 & 54) and the knob 532 (which may be a T-handle, for example) is rotated about the threaded shaft 534 so that the knob 532 advances in a distal direction until it contacts the outer tube 512. Further advancement of the knob 532 while it is engaged with the outer tube 512 drives the outer tube 512 and inner member 514 downward and thus simultaneously reduces the spinal rod(s) 404 (which are engaged with the arm(s) 520 of the outer tube 512) and the staple cap 410 (which is engaged to the distal engagement end 526 of the inner member 514 via the lock nut 512). When the rod 404 is fully seated within the staple body 506 (as described above) the thumbwheel 528 is actuated which causes the lock nut 412 to rotate, breaking the spot welds (if any) and tightening the lock nut 412 onto the staple body post (or bone screw head, depending on the embodiment used) to lock the vertebral fixation system 400 together. The reducer 510 and guide post 454 are then removed from the operative corridor.

Figures 55, 56:
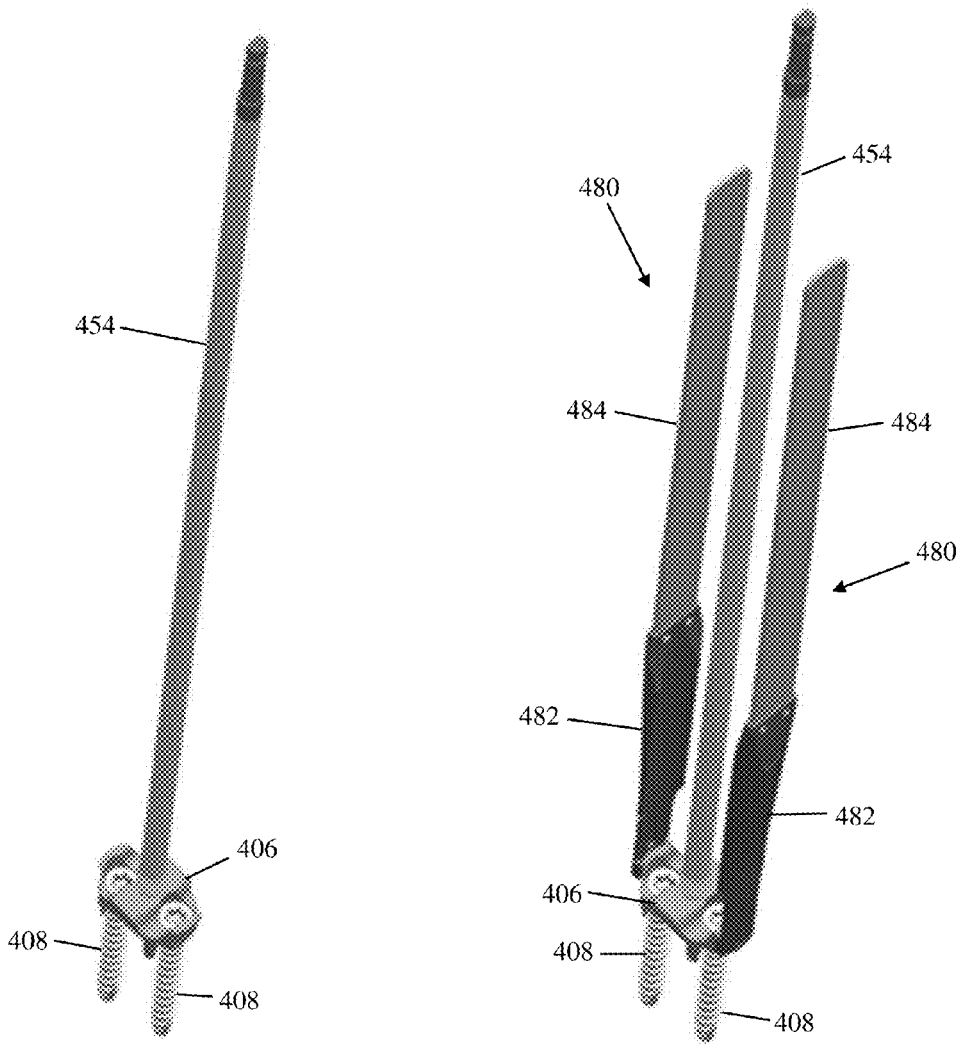

FIGS. 55-56 illustrate an example of alternate embodiment of the guide assembly 450 used with the vertebral fixation system 400 as shown and described above, with alternative guide sleeves 480 being the only structural difference. The guide sleeves 480 are similar to the guide sleeves 454 in every way (such that repeat description is not necessary) except that the guide sleeves 480 each include a lower portion 482 and an upper portion 484. The lower portion 482 is made of a rigid metal (e.g. stainless steel, titanium, and the like). The upper portion 484 is made of a shape memory material (e.g. nitinol). At normal temperatures the upper portion 484 of the guide sleeve 480 is bendable. Thus the guide sleeves 480 may be positioned as desired and then bent out of the way to provide better visualization, access, and help to keep tissue from creeping into the staple construct. After use, the guide sleeves 480 may be heated to return them to their original position for reuse.

Figure 57:
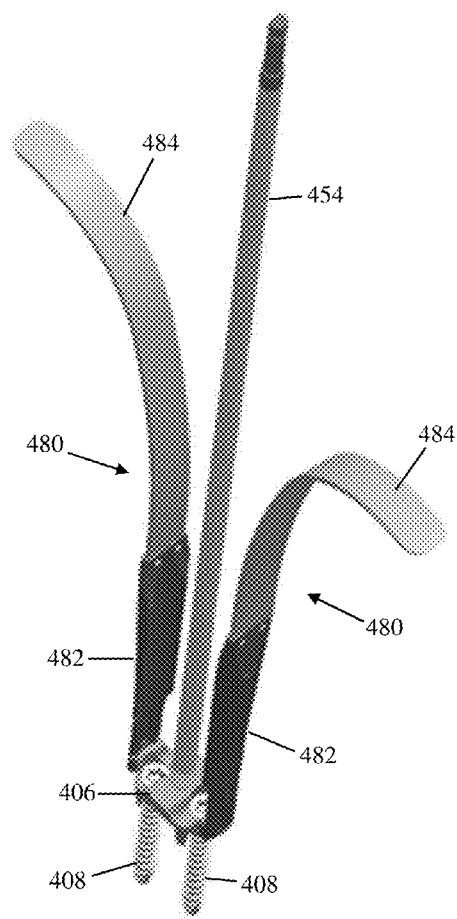
Figure 58:
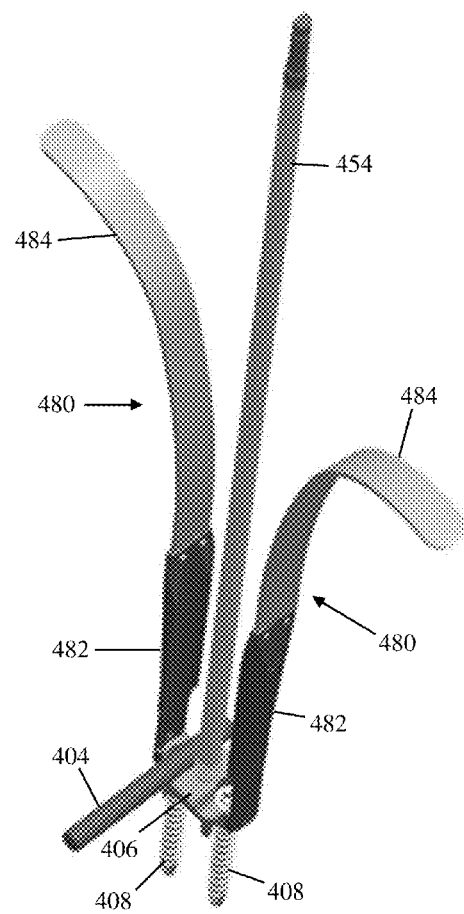
Figure 59:
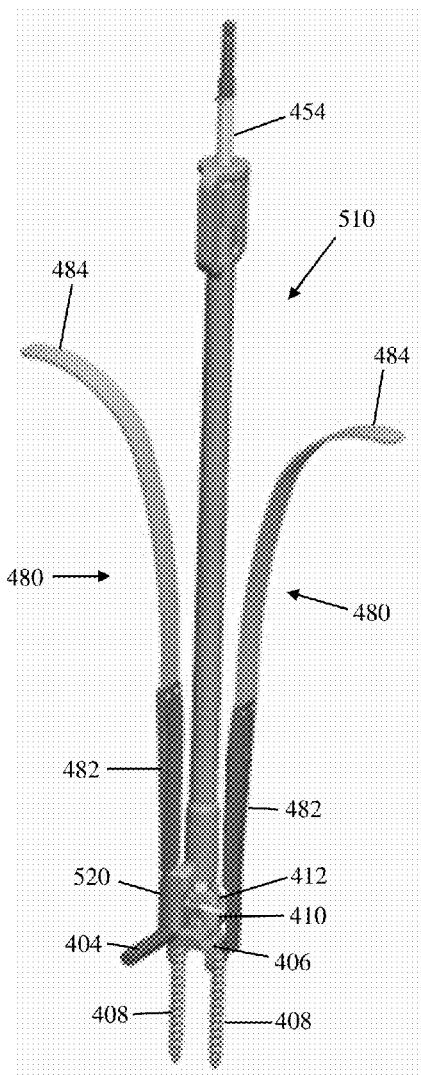
Figure 60:
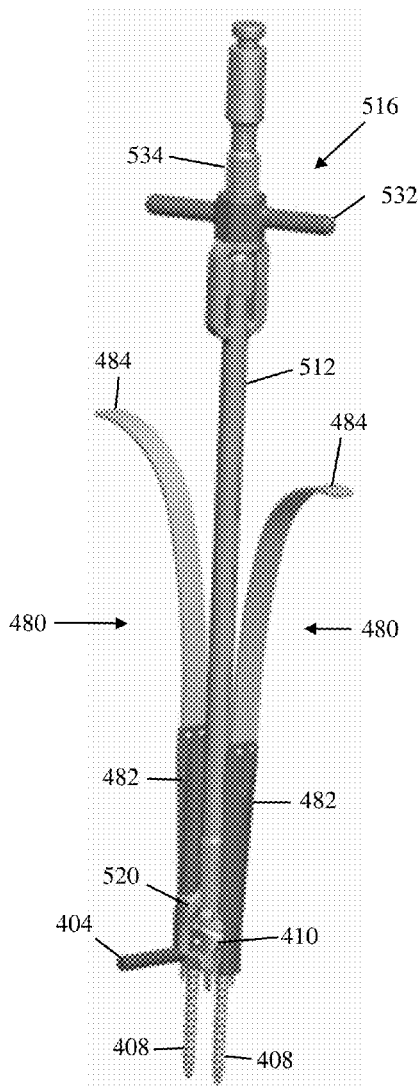
Figures 61, 62:
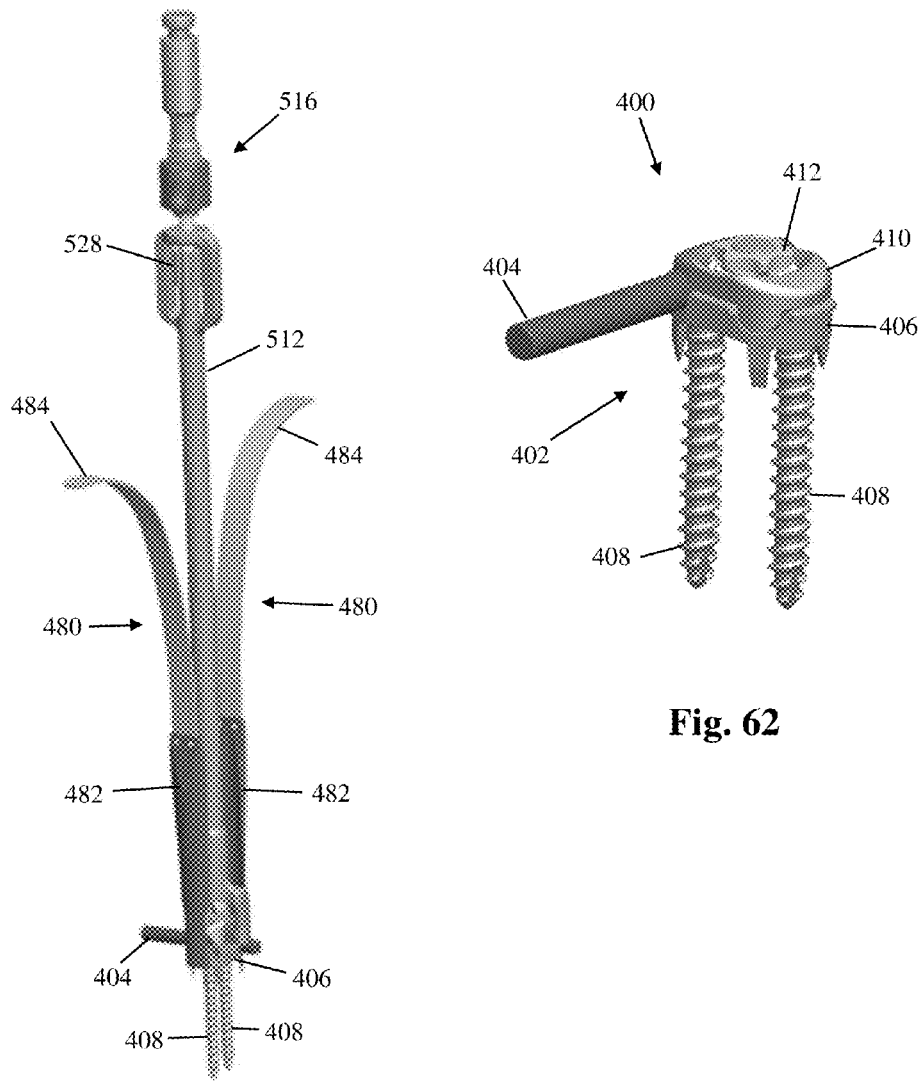

With reference to FIGS. 55-62, the guide assembly 450 with guide sleeves 480 may be used with the vertebral fixation system 400, as well as with the reducer 510 as described above. The first step is to implant the staple body 406 and bone screws 408 in a desired location on the vertebral body as described above. Once the staple body 406 and bone screws 408 are in place, the guide post 454 may be attached as described above (and shown in FIG. 55). The guide sleeves 480 may be positively engaged to the staple body 406 as shown in FIG. 56 and described above (and either inserted with the staple body 406 or inserted after the staple body 406 and subsequently engaged). For example, the positive engagement is created when the hooks slidably engage the engagement features on the staple body 406 and the deflectable tab is seated within the tab hole. The initial position of the upper portion 484 of the guide sleeves 480 is straight for insertion down the operative corridor. As shown in FIG. 57, once the guide sleeves 480 are attached the upper portion 484 may be bent outward (e.g. away from the operative corridor). The spinal rod 404 is then placed within the staple body 406 in the manner described above and as illustrated in FIG. 58. If a dual rod construct is being used, a second spinal rod 404 is also placed within the staple body 406 at this point. As shown in FIG. 59, the reducer 510 is then provided with an attached staple cap 410 as described above, and advanced along the guide post 454 until the arm(s) 520 engage the spinal rod 404. At this point the A/O reducer 516 is attached to the proximal end of the outer tube 512 (FIG. 60) and the knob 532 (which may be a T-handle, for example) is rotated about the threaded shaft 534 so that the knob 532 advances in a distal direction until it contacts the outer tube 512. Further advancement of the knob 532 while it is engaged with the outer tube 512 drives the outer tube 512 and inner member 514 downward and thus simultaneously reduces the spinal rod(s) 404 (which are engaged with the arm(s) 520 of the outer tube 512) and the staple cap 410 (which is engaged to the distal engagement end 526 of the inner member 514 via the lock nut 512). When the rod 404 is fully seated within the staple body 506 (as described above) the thumbwheel 528 is actuated which causes the lock nut 412 to rotate, breaking the spot welds (if any) and tightening the lock nut 412 onto the staple body post (or bone screw head, depending on the embodiment used) to lock the vertebral fixation system 400 together (FIG. 61). The reducer 510 and guide post 454 are then removed from the operative corridor, leaving the fully assembled and implanted vertebral fixation system 400 in place on the spine (FIG. 62).

FIGS. 63-69 illustrate an example of a vertebral fixation system 600 according to a fifth embodiment of the present invention. By way of example only, the vertebral fixation system 600 is presented as a dual screw, dual rod construct however other configurations are possible. As with the various embodiments described previously, the vertebral fixation system 600 includes a plurality of anchor assemblies 602 that are implanted into two or more adjacent vertebral bodies and then connected by a pair of spinal rods 604. Each anchor assembly 602 includes a staple body 606, a pair of bone screws 608, a hinge cap 610, a secondary cap 612, and a lock nut 614. Generally, the vertebral fixation system 600 of the current embodiment allows for the sequential securing of a pair of spinal rods by providing a hinge cap 610 capable of being moved from a first "open" position (which allows for insertion of the spinal rod 604 into a first rod-receiving recess 626 on the staple body 606) to a second "closed" position once the first spinal rod 604 is in place. The second spinal rod 604 may then be inserted into the second rod-receiving recess 627 and then secured with a secondary cap 612 and lock nut 614 (which locks the entire anchor assembly 602 together).

The staple body 606 includes a first surface 616 and a second surface 618 opposite the first surface 616. The first surface 616 is configured to engage the vertebral body and thus has a generally concave curvature to better fit the generally convex contour of the lateral aspect of the vertebral body. The staple body 606 includes one or more projections 620 extending generally perpendicularly from the first surface 616 to provide purchase for the staple body 606 within the vertebral body. By way of example, the projections 620 are provided as elongated posts that taper to a sharp distal edge 622 that may be impacted into the vertebral body such that upon implantation of the staple body 606 the first surface 616 rests flush against the lateral surface of the vertebral body. Although shown by way of example as four projections 620 distributed around the outside edge of the staple body 606, the projections 620 may be provided in various alternative numbers and/or configurations from that shown. For example, the projections may be arranged along the interior of the first surface 616. The number of projections 620 may also vary from the four shown to include a single projection or many smaller projections without departing from the scope of the present invention.

By way of example only, the second surface 618 is generally planar, however other configurations are possible. The staple body 606 includes a threaded post 624 extending generally perpendicularly in a proximal direction from the second surface 618 and configured to threadedly engage the lock nut 614. The staple body 606 further includes a pair of rod-receiving recesses 626, 627 formed within the second surface 618 and positioned with one on each side of the post 624. The recesses 626, 627 are each configured to receive a spinal rod 604. The first recess 626 is configured to receive the first spinal rod 604 during implantation, while the second recess 627 is configured to receive the second spinal rod 604 during implantation. Within each recess 626, 627 is an aperture 628 configured to receive a bone screw 608 therethrough. A friction element 630 is provided on the side of the staple body 606 that is adjacent the first recess 626. The friction element 630 is provided to frictionally lock the hinge cap 610 in place. Alternatively to the friction element 630, the hinge cap 610 may be locked in place via any other suitable method, for example a snap lock or a setscrew (not shown). By way of example only, the friction element 630 is provided as a series of ridges, however other friction elements are possible without departing from the scope of the invention. The hinge cap 610 is hingedly attached to the stable body 606, as described below.

The hinge cap 610 includes a cap portion 632, a hinge connector 634, a hinge window 636, and a hinge cap pin 638. The hinge cap portion 632 (when the hinge cap 610 is in a "closed" position) extends over the first rod receiving recess 626 to prevent ejection of the spinal rod 604 from the recess 626. The hinge cap 610 has a generally concave rod-interfacing surface 640 on the underside of the hinge cap portion 632. The hinge cap portion 632 further has a locking element 642 configured to interact with the friction element 630 on the staple body 606 to lock the hinge cap 610 in a "closed" position. By way of example only the locking element 632 is provided as a latch member configured to interact with the friction element 630, however other configurations are possible. The hinge connector 634 is provided as a pair of arms that extend from the hinge cap portion 632 to the staple body 606. The arms of the hinge connector 634 are spaced apart forming a hinge window 636 between them. The hinge window 636 ensures that other structure (e.g. post 624) do not inhibit the ability of the hinge cap 610 to migrate from the "open" position to the "closed" position. The arms of the hinge connector 634 are attached to the staple body 606 on either side of the threaded post 624 and in between the recesses 626, 627. A hinge cap pin 638 is laser welded to the hinge cap 610 and extends through the staple body 606 under the threaded post 624.

The secondary cap 612 has a cap portion 644 that extends over the second rod-receiving recess 627 and has a generally concave rod interfacing surface 646 positioned on the underside of the cap portion 644. The secondary cap 612 further has a lock nut aperture 648 dimensioned to seat the lock nut 614 therein, and a flange 650 configured to reside within the hinge window 636 when the secondary cap 612 is fully installed on the construct.

The lock nut 614 is similar to the lock nut 24 shown and described in relation to FIG. 3 such that a repeat discussion is not necessary. Likewise, each of the bone screws 608 used with the vertebral fixation system 600 are identical, and are similar to the bone screws 18 shown and described in relation to FIG. 3 such that a repeat discussion is not necessary.

Figure 64:
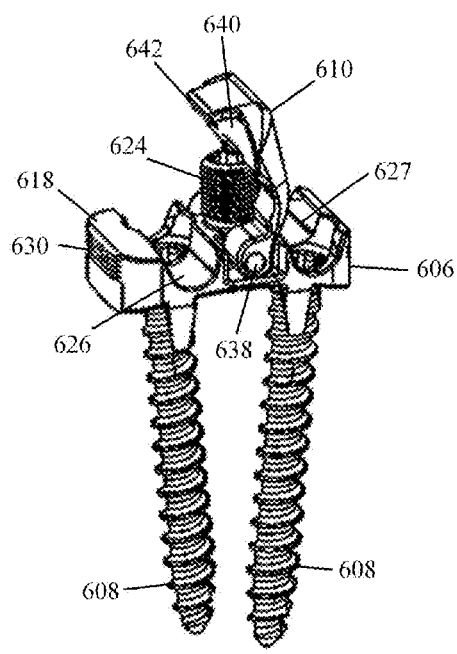
Figure 65:
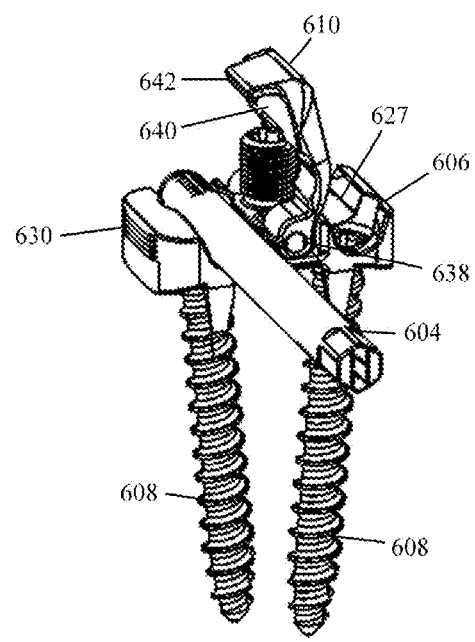
Figure 66:
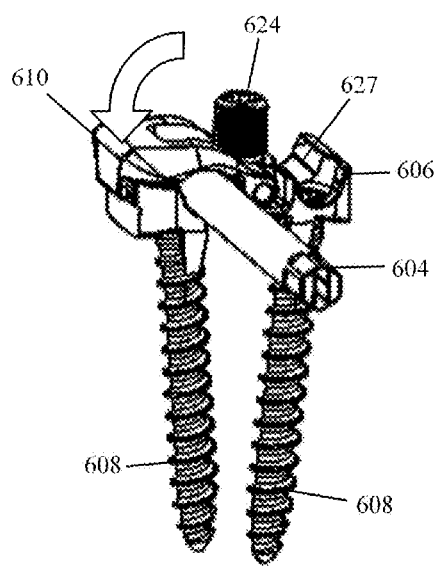
Figure 67:
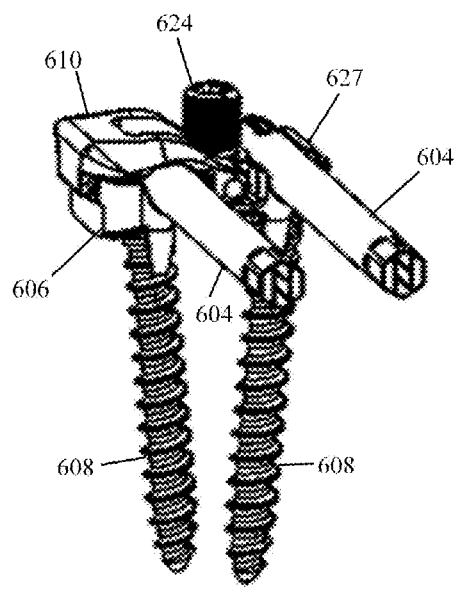
Figure 68:
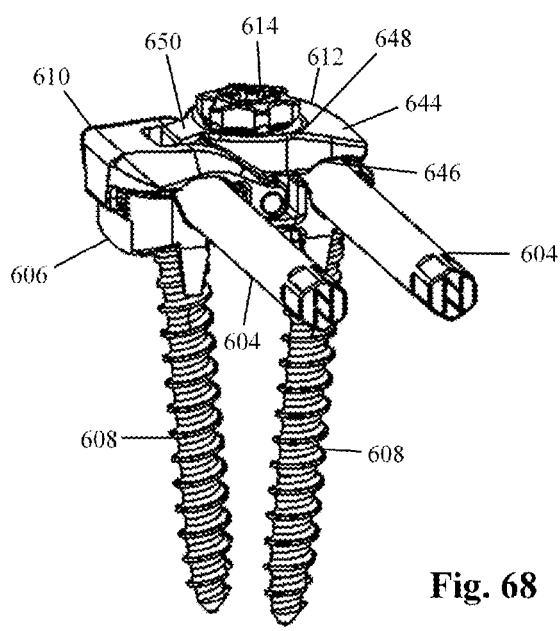

In use, a vertebral fixation procedure is started with the surgeon creating an operative corridor to a surgical target site. This may be accomplished, for example, via a lateral, transpsoas approach, such as that described in the above-referenced '840 patent (incorporated by reference). Next, the staple body 606 is anchored to a lateral aspect of a vertebral body by first impacting the projections 620 into the vertebral body. With the hinge cap 610 in the "open" position, a pair of bone screws 608 are inserted through the apertures 628 and driven into the vertebral body for purchase (FIG. 64). Once the staple body 606 is in place, the spinal rods 604 are inserted into each of the rod-receiving recesses 626, 627. This is done sequentially, with a first spinal rod 604 being inserted in to the first recess 626 with the hinge cap 610 in the "open" position (FIG. 65). Once the first spinal rod 604 is seated, the hinge cap 610 is moved to the "closed" position and locked into place as described above (FIG. 66). The second spinal rod 604 is then inserted into the second rod-receiving recess 627 (FIG. 67). At this point, the supplemental cap 612 is attached and the lock nut 614 is tightened on the threaded post 624 to lock the anchor assembly 602 together (FIG. 68). The procedure is completed once the desired number of anchor assemblies 602 have been implanted and connected by spinal rods 604 (FIG. 69). Upon completion of the implantation steps, the surgeon will remove any instrumentation used to maintain the operative corridor and close the surgical wound.

FIGS. 70-81 illustrate an example of a vertebral fixation system 700 according to a sixth embodiment of the present invention. The vertebral fixation system 700 is particularly suited for segmental insertion. That is, the vertebral fixation system 700 is capable of being implanted one vertebral level at a time through multiple exposures, as will be described in further detail below. Although the vertebral fixation system 700 is shown and described as a single bolt, single rod construct, other configurations are possible (for example such as any of the above-disclosed configurations) without departing from the scope of the invention.

By way of example only, the vertebral fixation system 700 includes a plurality of anchor assemblies 702 that are implanted into two or more adjacent vertebral bodies and then connected by a plurality of spinal rods 704. Each anchor assembly 702 includes a staple body 706, a bone bolt 708, a hinge cap 710, a secondary cap 712, and a lock nut 714. Generally, the vertebral fixation system 700 of the current embodiment allows for the sequential securing of at least a pair of spinal rods by providing a hinge cap 710 capable of being moved from a first "open" position (which allows for insertion of a first spinal rod 704 into a first rod-receiving recess 726 on the staple body 706) to a second "closed" position once the first spinal rod 704 is in place. The second spinal rod 704 may then be inserted into the second rod-receiving recess 727 and then secured with a secondary cap 712 and lock nut 714 (which locks the entire anchor assembly 702 together).

The staple body 706 includes a first surface 716 and a second surface 718 opposite the first surface 716. The first surface 716 is configured to engage the vertebral body and thus has a generally concave curvature to better fit the generally convex contour of the lateral aspect of the vertebral body. The staple body 706 includes one or more projections 720 extending generally perpendicularly from the first surface 716 to provide purchase for the staple body 706 within the vertebral body. By way of example, the projections 720 are provided as elongated posts that taper to a sharp distal edge 722 that may be impacted into the vertebral body such that upon implantation of the staple body 706 the first surface 716 rests flush against the lateral surface of the vertebral body.

By way of example only, the second surface 718 is generally planar, however other configurations are possible. The staple body 706 includes a main aperture 724 offset from the midline of the staple body 706 and configured to allow passage of the threaded post 760 of the bone bolt 708. The staple body 706 further includes a rod channel 725 formed in the second surface 718 and offset from the midline of the staple body 706 opposite the main aperture 724. The rod channel 725 includes a pair of concave recesses 726, 727 that are each dimensioned to seat a collet 766 of a spinal rod 704. The first recess 726 is configured to receive the first spinal rod 704 during implantation, while the second recess 727 is configured to receive the second spinal rod 704 during implantation. A hinge pin 728 is provided on the side of the staple body 706 opposite rod channel 725. The hinge pin 728 is the means (by way of example only) by which the hinge cap 710 is hingedly attached to the staple body 706. The staple body 706 further includes a threaded aperture 730 configured to receive a setscrew 738. The staple body 706 further includes an attachment element 731 configured to interface with an instrument, for example a guide sleeve or reducer as described above. The attachment element 731 is identical in structure and function to the engagement feature 420 of the staple body 406 described above with reference to FIG. 44 such that a repeat discussion is not necessary.

The hinge cap 710 includes a cap portion 732, a hinge connector 734, and a threaded aperture 736. The hinge cap portion 732 (when the hinge cap 710 is in a "closed" position) extends over the first rod receiving recess 726 to prevent ejection of the spinal rod 704 from the recess 726. In a significant aspect of the invention, the hinge cap portion 732 does not cover any portion of the second rod receiving recess 727 so that a second spinal rod 704 may be inserted into the second rod receiving recess 727 after the hinge cap 710 has been locked in the "closed" position. The hinge cap 710 has a generally concave rod-interfacing surface 740 on the underside of the hinge cap portion 732. The hinge connector 734 is configured to engage the hinge pin 728 on the staple body 706 to form the hinged attachment of the hinge cap 710. The threaded aperture 736 is configured to receive the setscrew 738 to lock the hinge cap 710 in the "closed" position.

The secondary cap 712 has a cap portion 744 that extends over the second rod receiving recess 727 and has a generally concave rod interfacing surface 746 positioned on the underside of the cap portion 744. The secondary cap 712 further has a lock nut aperture 748 dimensioned to seat the lock nut 714 therein, and a flange 750 that extends over the top of the hinge cap 710 (including at least a portion of the setscrew 738) when the secondary cap 712 is fully installed on the construct. The lock nut 714 is similar to the lock nut 24 shown and described in relation to FIG. 3 such that a repeat discussion is not necessary.

Referring to FIG. 78, the bone bolt 708 includes a head portion 752 and a threaded shaft 754. The head portion 752 includes a top surface 756 having an engagement recess 758 formed therein that is configured to engage with a suitable driver instrument (not shown). The head portion 752 further includes a threaded post 760 dimensioned to engage with the lock nut 714. The neck portion 762 includes a generally convex surface 764 extending circumferentially around the bone bolt 708. The generally convex surface 764 is provided with a frictional element in the form of (and by way of example only) a plurality of splines extending radially (e.g. in a sunburst pattern) from the shaft of the bone bolt 708. When the bone bolt 708 is fully engaged to the staple body 706, the neck portion 762 is seated within a bolt recess (not shown) formed in the first surface 716 of the staple body 706 around the main aperture 724. The bolt recess is provided with a complementary set of splines arranged in a sunburst pattern. The splines interact to ensure that the bone bolt 708 does not rotate relative to the staple body 706 during implantation of the anchor assembly 702.

Referring to FIGS. 79-81, the spinal rod 704 is a generally cylindrical rod segment that is sized to span only one vertebral level. That is, the spinal rod 704 is sized to extend between two vertebra (that is, the spinal rod 704 is sized to extend between a pair of anchor assemblies 702 implanted into adjacent vertebra). A collet 766 may be added to at least one end of the spinal rod 704 to aid in insertion. The collet 766 has an outer surface with a generally convex curvature. The collet 766 is configured to be seated within the rod receiving recesses 726, 727 of the staple body 706. Preferably, the end with the collet 766 is inserted first, into rod receiving recess 726 as shown in FIG. 81. This allows the angle of the spinal rod 704 to be adjustable during alignment with the adjacent anchor assembly 702 while also preventing the spinal rod 704 from becoming dislodged from the rod channel 725. Optionally, a second collet 766 may be provided on the other end of the spinal rod 704.

Generally, implantation of the vertebral fixation system 700 involves the sequential implantation of a series of anchor assemblies 702 connected by a series of rod segments 704. Because of the modular design, implantation of the system at each vertebral level may be achieved through an independent operative corridor. One example of a vertebral fixation procedure using the vertebral fixation system 700 is started with the surgeon creating a first minimally invasive operative corridor to a surgical target site. By way of example, the minimally invasive exposure will include portions of first and second adjacent vertebral bodies. This may be accomplished, for example, via a lateral, trans-psoas approach such as that described in the above-referenced '840 patent (incorporated by reference). A first bone bolt 708 and first staple body 706 are anchored to a lateral aspect of the vertebral body. By way of example, the first anchor assembly 702 in the series may be implanted with the hinge cap 710 in the "closed" and locked position even though no rod segment occupies the first rod-receiving recess 726. The first end of a first spinal rod 704 (including collet 766) is inserted into the second rod receiving recess 727 on the first staple body 706 and the other end of the spinal rod 704 (with collet 766) is inserted into the first rod receiving recess 727 of the second staple body 706 (on the second vertebral body, and with the hinge cap 710 of the second anchor assembly 702 in the "open" position). Once the first spinal rod 704 is seated, the hinge cap 710 on the second staple body 706 is moved to the "closed" position and locked into place with a setscrew 738. The secondary cap 712 and lock nut 714 may be applied to the first anchor assembly 702 at this point to lock the construct together since (by way of example only) the first anchor assembly 702 comprises the terminus of a segmented construct. At this point, the first rod segment 704 is locked to both the first anchor assembly 702 (via the application of the secondary cap 712 and lock nut 714 to fully assembly the first anchor assembly) and the second anchor assembly 702 (via the locked hinge cap 710). Since fixation at the first spinal level is completed, the first operative corridor may be closed.

A second spinal level, including the second staple 706 (already implanted with the first spinal rod segment locked in place with the hinge cap 710) and associated vertebra and a third vertebra may then be exposed through a second minimally invasive exposure. A third staple body 706 is then attached to the third vertebra. With the hinge cap 710 of the third staple body 706 in the "open" position, a first end of a second spinal rod 704 (including collet 766) is inserted into the second rod receiving recess 727 on the second staple body 706 and the other end of the spinal rod 704 (with collet 766) is inserted into the first rod receiving recess 726 of the third staple body 706 (on the third vertebral body). Once the second spinal rod 704 is seated, the hinge cap 710 on the third staple body 706 is moved to the "closed" position and locked into place with a setscrew 738. The secondary cap 712 and lock nut 714 may be applied to the second anchor assembly 702 at this point to lock the construct together since (by way of example only) the second anchor assembly 702 is completed at this level. At this point, the second rod segment 704 is locked to both the second anchor assembly 702 (via the application of the secondary cap 712 and lock nut 714 to fully assembly the second anchor assembly) and the third anchor assembly 702 (via the locked hinge cap 710). Since fixation at the second spinal level is completed, the second operative corridor may be closed. These steps may be repeated across multiple levels of the spine. The procedure is completed once the desired number of anchor assemblies 702 have been implanted and connected by spinal rod segments 704.

FIGS. 82-83 illustrate an example of an anchor assembly 802 according to a seventh embodiment of the present invention for use with any of the above-described examples of the vertebral fixation system. The anchor assembly 802 generally is a single screw, single rod construct. The anchor assembly 802 includes a staple body 806, a bone bolt 808, a staple cap 810, an axial clip 812, and a lock nut 814. The staple body 806 includes a first surface 816 and a second surface 818 opposite the first surface 816. The first surface 816 is configured to engage the vertebral body and thus has a generally concave curvature to better fit the generally convex contour of the lateral aspect of the vertebral body. The staple body 806 includes one or more projections 820 extending generally perpendicularly from the first surface 816 to provide purchase for the staple body 806 within the vertebral body. By way of example, the projections 820 are provided as elongated cylindrical posts with a conical tip 822 that may be impacted into the vertebral body such that upon implantation of the staple body 806 the first surface 816 rests flush against the lateral surface of the vertebral body.

By way of example only, the second surface 818 is generally planar, however other configurations are possible. The staple body 806 includes an aperture 824 extending axially therethrough and configured to allow passage of the threaded post 838 of the bone bolt 808 therethrough. The staple body 806 further includes a rod channel 826 formed within the second surface 818 and positioned on one side of the aperture 824. The rod channel 826 is configured to receive at least a portion of the spinal rod (not shown). The staple body 806 includes a pair of lateral recesses 828 positioned on opposite side surfaces of the staple body 806. The lateral recesses 828 are configured to receive the flanges 850 of the staple cap 810 to ensure proper alignment and engagement of the staple cap 810 and staple body 806. The staple body 806 further includes an attachment element 831 configured to interface with an instrument, for example a guide sleeve or reducer as described above. The attachment element 831 is identical in structure and function to the engagement feature 420 of the staple body 406 described above with reference to FIG. 44 such that a repeat discussion is not necessary.

The bone bolt 808 includes a head portion 832 and a threaded shaft 834. The head portion 832 includes a top surface having an engagement recess 836 formed therein that is configured to engage with a suitable driver instrument (not shown). The head portion 832 further includes a threaded post 838 dimensioned to engage with the lock nut 814. The neck portion 840 includes a generally convex surface 842 extending circumferentially around the bone bolt 808. The generally convex surface 842 is provided with a frictional element in the form of (and by way of example only) a plurality of splines extending radially (e.g. in a sunburst pattern) from the shaft of the bone bolt 808. When the bone bolt 808 is fully engaged to the staple body 806, the neck portion 840 is seated within a bolt recess 830 formed in the first surface 816 of the staple body 806 around the aperture 824. The bolt recess 830 is provided with a complementary set of splines arranged in a sunburst pattern. The splines interact to ensure that the bone bolt 808 does not rotate relative to the staple body 806 during implantation of the anchor assembly 802.

The staple cap 810 is configured to mate with the staple body 806, and includes a cap portion 844, an aperture 846 that extends through the center of the staple cap 810 and is dimensioned to receive the threaded post 838 of the bone bolt 808 therethrough. The underside of the cap portion 844 includes a concave recess (not shown) dimensioned to receive at least a portion of the spinal rod and is configured to form an upper boundary of the rod channel 826 of the staple body 806. The staple cap 810 further includes a circular recess 848 surrounding the aperture 846 and configured to receive the axial clip 812 therein. The staple cap 810 further includes a pair of flanges 850 positioned on either side of the staple cap 810 and extending in a distal direction. The flanges 850 are configured to mate with the lateral recesses 828 on either side of the staple body 806 to ensure proper alignment and engagement of the staple cap 810 and staple body 806. A pair of engagement recesses 852 are formed within the side of the staple cap 810 proximal of the flanges 850. The engagement recesses 852 are configured to facilitate engagement with any number of auxiliary instruments (not shown) that may be used with the anchor assembly 802, for example including but not limited to an inserter, rod reducer, and the like.

The axial clip 812 acts as a washer. The axial clip 812 includes at least one flexible protrusion 854 that is snaps into the aperture 846 of the staple cap 810. The axial clip 812 further includes a central aperture 856 and a concave surface 858 surrounding the central aperture 856. The concave surface 858 is configured to seat the lock nut 814 therein. Upon assembly, the axial clip 814 resides in the circular recess 848 of the staple cap 810 and the one or more flexible protrusions 854 are captured within the aperture 846 to keep the clip 812 in place.

The lock nut 214 includes a lower surface 860, a circumferential purchase region 862, and a threaded aperture 864 extending therethrough. The lower surface 860 is convex and is configured to mate with the concave surface 858 of the axial clip 812. The circumferential purchase region 862 includes a plurality of projections and recesses that are designed to mate with an insertion instrument (not shown). The threaded aperture 864 mates with the threaded post 838 of the bone bolt 808. The lock nut 814 may be spot welded to the axial clip 812 such that the staple cap 810, axial clip 812 and lock nut 814 are held together as a single piece to aid insertion and limit the number of small pieces and steps required to install the device. Once the lock nut 814 is aligned with the threaded post 838 and appropriate torque is applied, the spot welds are broken and the lock nut 814 may be rotated to tighten the construct.

In use, a vertebral fixation procedure is started with the surgeon creating an operative corridor to a surgical target site. This may be accomplished, for example, via a lateral, transpsoas approach, such as that described in the above-referenced '840 patent (incorporated by reference). Next, the bone bolt 808 is driven into the vertebral body at a desired location. The staple body 806 is then inserted such that the threaded post 838 of the bone bolt 808 is passed through the aperture 824 and convex surface 842 of the neck region 840 of the bone bolt 808 resides within the recess 830 of the staple body 806. The radial splines on the bone bolt 808 interact with the radial splines in the recess 830 to prevent rotation of the staple body 806 relative to the bone bolt 808. The staple body 806 is anchored to a lateral aspect of a vertebral body by impacting the projections 820 into the vertebral body. Once the staple body 806 is in place, a spinal rod is inserted into the rod channel 826. At this point, the staple cap 810 with attached axial clip 812 and lock nut 814 are applied to the staple body 806 and a reducer instrument (described above) is employed to provide the necessary compression force on the spinal rod. The lock nut 814 is then rotated (e.g. clockwise) to lock the anchor assembly 802 together. The procedure is completed once the desired number of anchor assemblies 802 have been implanted and connected by one or more spinal rods. Upon completion of the implantation steps, the surgeon will remove any instrumentation used to maintain the operative corridor and close the surgical wound.

FIGS. 84-85 illustrate an example of an anchor assembly 902 according to an eighth embodiment of the present invention for use with any of the above-described examples of the vertebral fixation system. The anchor assembly 902 generally is a single screw, single rod construct. The anchor assembly 902 includes a staple body 906, a bone bolt 908, a staple cap 910, an axial clip 912, and a lock nut 914. The staple body 906 includes a first surface 916 and a second surface 918 opposite the first surface 916. The first surface 916 is configured to engage the vertebral body and thus has a generally concave curvature to better fit the generally convex contour of the lateral aspect of the vertebral body. The staple body 906 includes one or more projections 920 extending generally perpendicularly from the first surface 916 to provide purchase for the staple body 906 within the vertebral body. By way of example, the projections 920 are provided as elongated posts that taper to a sharp distal edge 922 that may be impacted into the vertebral body such that upon implantation of the staple body 906 the first surface 916 rests flush against the lateral surface of the vertebral body. Although shown by way of example as four projections 920 distributed around the outside edge of the staple body 906, the projections 920 may be provided in various alternative numbers and/or configurations from that shown. For example, the projections may be arranged along the interior of the first surface 916. The number of projections 920 may also vary from the four shown to include a single projection or many smaller projections without departing from the scope of the present invention.

By way of example only, the second surface 918 is generally planar, however other configurations are possible. The staple body 906 includes an aperture 924 extending axially therethrough and configured to allow passage of the threaded post 938 of the bone bolt 908 therethrough. The staple body 906 further includes a rod channel 926 formed within the second surface 918 and positioned on one side of the aperture 924. The rod channel 926 is configured to receive at least a portion of the spinal rod (not shown). The staple body 906 includes a pair of lateral recesses 928 positioned on opposite side surfaces of the staple body 906. The lateral recesses 928 are configured to receive the flanges 950 of the staple cap 910 to ensure proper alignment and engagement of the staple cap 910 and staple body 906. The staple body 906 further includes an attachment element 931 configured to interface with an instrument, for example a guide sleeve or reducer as described above. The attachment element 931 is identical in structure and function to the engagement feature 420 of the staple body 406 described above with reference to FIG. 44 such that a repeat discussion is not necessary.

The bone bolt 908 includes a head portion 932 and a threaded shaft 934. The head portion 932 includes a top surface having an engagement recess 936 formed therein that is configured to engage with a suitable driver instrument (not shown). The head portion 932 further includes a threaded post 938 dimensioned to engage with the lock nut 914. The neck portion 940 includes a generally convex surface 942 extending circumferentially around the bone bolt 908. The generally convex surface 942 is provided with a frictional element in the form of (and by way of example only) a plurality of splines extending radially (e.g. in a sunburst pattern) from the shaft of the bone bolt 908. When the bone bolt 908 is fully engaged to the staple body 906, the neck portion 940 is seated within a bolt recess 930 formed in the first surface 916 of the staple body 906 around the aperture 924. The bolt recess 930 is provided with a complementary set of splines arranged in a sunburst pattern. The splines interact to ensure that the bone bolt 908 does not rotate relative to the staple body 906 during implantation of the anchor assembly 902.

The staple cap 910 is configured to mate with the staple body 906, and includes a cap portion 944, an aperture 946 that extends through the center of the staple cap 910 and is dimensioned to receive the threaded post 938 of the bone bolt 908 therethrough. The underside of the cap portion 944 includes a concave recess (not shown) dimensioned to receive at least a portion of the spinal rod and is configured to form an upper boundary of the rod channel 926 of the staple body 906. The staple cap 910 further includes a circular recess 948 surrounding the aperture 946 and configured to receive the axial clip 912 therein. The circular recess 948 includes a circumferential lip 949 dimensioned to capture the axial clip 912. The staple cap 910 further includes a pair of flanges 950 positioned on either side of the staple cap 910 and extending in a distal direction. The flanges 950 are configured to mate with the lateral recesses 928 on either side of the staple body 906 to ensure proper alignment and engagement of the staple cap 910 and staple body 906. A pair of engagement recesses 952 are formed within the side of the staple cap 910 proximal of the flanges 950. The engagement recesses 952 are configured to facilitate engagement with any number of auxiliary instruments (not shown) that may be used with the anchor assembly 902, for example including but not limited to an inserter, rod reducer, and the like.

The axial clip 912 acts as a washer. The axial clip 912 includes at least one flexible protrusion 954 that is snaps into the aperture 946 of the staple cap 910. The axial clip 912 further includes a central aperture 956 and a concave surface 958 surrounding the central aperture 956. The concave surface 958 is configured to seat the lock nut 914 therein. Upon assembly, the axial clip 914 resides in the circular recess 948 of the staple cap 910 and the one or more flexible protrusions 954 are captured under lip 949 to keep the clip 912 in place.

The lock nut 214 includes a lower surface 960, a circumferential purchase region 962, and a threaded aperture 964 extending therethrough. The lower surface 960 is convex and is configured to mate with the concave surface 958 of the axial clip 912. The circumferential purchase region 962 includes a plurality of projections and recesses that are designed to mate with an insertion instrument (not shown). The threaded aperture 964 mates with the threaded post 938 of the bone bolt 908. The lock nut 914 may be spot welded to the axial clip 912 such that the staple cap 910, axial clip 912 and lock nut 914 are held together as a single piece to aid insertion and limit the number of small pieces and steps required to install the device. Once the lock nut 914 is aligned with the threaded post 938 and appropriate torque is applied, the spot welds are broken and the lock nut 914 may be rotated to tighten the construct.

In use, a vertebral fixation procedure is started with the surgeon creating an operative corridor to a surgical target site. This may be accomplished, for example, via a lateral, transpsoas approach, such as that described in the above-referenced '840 patent (incorporated by reference). Next, the bone bolt 908 is driven into the vertebral body at a desired location. The staple body 906 is then inserted such that the threaded post 938 of the bone bolt 908 is passed through the aperture 924 and convex surface 942 of the neck region 940 of the bone bolt 908 resides within the recess 930 of the staple body 906. The radial splines on the bone bolt 908 interact with the radial splines in the recess 930 to prevent rotation of the staple body 906 relative to the bone bolt 908. The staple body 906 is anchored to a lateral aspect of a vertebral body by impacting the projections 920 into the vertebral body. Once the staple body 906 is in place, a spinal rod is inserted into the rod channel 926. At this point, the staple cap 910 with attached axial clip 912 and lock nut 914 are applied to the staple body 906 and a reducer instrument (described above) is employed to provide the necessary compression force on the spinal rod. The lock nut 914 is then rotated (e.g. clockwise) to lock the anchor assembly 902 together. The procedure is completed once the desired number of anchor assemblies 902 have been implanted and connected by one or more spinal rods. Upon completion of the implantation steps, the surgeon will remove any instrumentation used to maintain the operative corridor and close the surgical wound.

The various inventive features of the vertebral fixation system have been described above with regards to specific examples. However, it should be understood that the possible combinations of the various features are not limited to the specific examples and combinations in which they are presented. Any feature described with respect to any of the above examples may be used in combination with any other feature or example described herein without departing from the scope of the invention. For example, FIG. 86 illustrates a portion of an anchor assembly in which several features from the anchor assembly 802 described with reference to FIGS. 82-83 above are combined with the anchor assembly 12 described with reference to FIGS. 1-6 above.

More specifically, FIG. 86 illustrates an example of a staple body 1002 suitable for use with in a single rod, dual screw construct. The staple body 1006 includes a first surface 1016 and a second surface 1018 opposite the first surface 1016. The first surface 1016 is configured to engage the vertebral body and thus has a generally concave curvature to better fit the generally convex contour of the lateral aspect of the vertebral body. The staple body 1006 includes one or more projections 1020 extending generally perpendicularly from the first surface 1016 to provide purchase for the staple body 1006 within the vertebral body. By way of example, the projections 1020 are provided as elongated posts that taper to a sharp distal edge 1022 that may be impacted into the vertebral body such that upon implantation of the staple body 1006 the first surface 1016 rests flush against the lateral surface of the vertebral body.

By way of example only, the second surface 1018 is generally planar, however other configurations are possible. The staple body 1006 includes a post 1024 extending generally perpendicularly in a proximal direction from the second surface 1018. The post 1024 includes a threaded region 1026 configured to threadedly engage the lock nut (not shown but identical in all respects to the lock nut 24 in FIG. 1). The staple body 1006 further includes a rod channel 1028 formed within the second surface 1018 and positioned on one side of the post 1024. The rod channel 1028 is configured to receive at least a portion of a spinal rod (not shown). Within the rod channel 1028 is an aperture 1030 configured to receive a bone screw 1008 therethrough (identical to bone screw 18 described above in all respects). The staple body 1006 has a second aperture 1031 extending therethrough and positioned on the opposite side of the post 1024. The second aperture 1031 is also configured to receive a bone screw 1008 therein. The staple body 1006 includes a pair of lateral recesses 1032 positioned on opposite side surfaces of the staple body 1006. The lateral recesses 1032 are configured to receive the flanges on the staple cap (not shown, however for example like flanges 950 of the staple cap 910 describe above) to ensure proper alignment and engagement of the staple cap and staple body 1006. The staple body 1006 further includes a pair of attachment elements 1034 positioned on either end of the staple body 1006 and configured to interface with an instrument, for example a guide sleeve or reducer as described above. The attachment element 1034 is identical in structure and function to the engagement feature 420 of the staple body 406 described above with reference to FIG. 44 such that a repeat discussion is not necessary. Other modifications are possible. Furthermore, although not shown, the vertebral fixation system of the present embodiment includes a staple cap, axial clip, lock nut, and spinal rod such as described in the various embodiments above.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

We claim:

1. A spinal fixation system configured for implantation on a lateral aspect of a human spine for immobilizing at least two adjacent spinal levels relative to one another, comprising:
   at least three anchor assemblies, each anchor assembly comprising:
   a staple base having a first rod-receiving recess coaxially aligned with a second rod-receiving recess, the first and second rod-receiving recesses dimensioned to receive an end portion of different spinal rod segments;
   a first blocking element hingedly attached to the staple base and moveable from a first position to a second position, the first position allowing placement of a first rod segment within the first rod-receiving recess, the second position covering the first rod-receiving recess while allowing placement of a second rod within the second rod-receiving recess;
   a second blocking element having a first portion covering the second rod-receiving recess and a second portion covering at least a portion of the first blocking element, the second blocking element attachable to the staple base subsequent to the movement of the first blocking element from the first position to the second position; an anchor element configured to anchor the anchor assembly to the vertebral body, the anchor element including an elongated threaded shaft for gaining purchase within a vertebra and a post element extending proximally from the shaft; and
   a locking element attachable to the post element, the locking element configured to apply a compressive force on the staple base, first blocking element, and second blocking element to lock the anchor assembly together; and
   at least two spinal rod segments, each spinal rod segment having a size sufficient to span the distance between a first anchor assembly implanted in a first vertebral body and a second anchor assembly implanted in a second vertebral body, the first spinal rod segment having an end portion dimensioned to be received in the first rod-receiving recess of the second anchor assembly, the second spinal rod segment having an end portion dimensioned to be received in the second rod-receiving recess of the second anchor assembly.

2. The spinal fixation system of claim 1, wherein the staple base includes at least one supplemental anchor element extending generally perpendicularly from a bottom surface of the staple base, the supplemental anchor element configured to penetrate a vertebral body.

3. The spinal fixation of claim 1, wherein the first blocking element is independently lockable to the staple base prior to the application of the second blocking element and locking element.

4. The spinal fixation system of claim 3, further comprising a setscrew configured to lock the first blocking element to the staple base when the first blocking element is in the second position.

5. The spinal fixation system of claim 1, wherein the staple base includes an aperture dimensioned to receive the post element there through.

6. The spinal fixation system of claim 5, wherein the staple base further includes a recess surrounding the aperture, the recess having a concave surface, the concave surface being provided with a first anti-migration feature.

7. The spinal fixation system of claim 6, wherein the anchor element has a neck portion having a convex surface, the convex surface dimensioned to mate with the concave surface of the recess, the convex surface being provided with a second anti-migration feature.

8. The spinal fixation system of claim 7, wherein the anti-migration feature comprises a plurality of splines radially arranged on the concave surface, the second anti-migration feature comprises a plurality of splines radially arranged on the convex surface, and the first and second anti-migration features cooperate to prevent rotation of the anchor element relative to the staple body.

9. A method for performing spine surgery, comprising:
   establishing a first minimally invasive operative corridor to a first spinal target site, the first spinal target site comprising at least a portion of a lateral aspect of a first vertebral body and at least a portion of a lateral aspect of a second vertebral body, the first and second vertebral bodies being adjacent one another;
   implanting a first anchor assembly in the lateral aspect of the first vertebral body, the first anchor assembly including a staple base having a first rod-receiving recess coaxially aligned with a second rod-receiving recess, the first and second rod-receiving recesses dimensioned to receive an end portion of different spinal rod segments, a first blocking element hingedly attached to the staple base and moveable from a first position to a second position, the first position allowing placement of a spinal rod segment within the first rod-receiving recess, the second position covering the first rod-receiving recess while allowing placement of a different spinal rod segment within the second rod-receiving recess, a second blocking element having a first portion covering the second rod-receiving recess and a second portion covering at least a portion of the first blocking element, the second blocking element attachable to the staple base subsequent to the movement of the first blocking element from the first position to the second position, and an anchor element configured to anchor the anchor assembly to the first vertebral body;
   implanting a second anchor assembly in the lateral aspect of the second vertebral body, the second anchor assembly including a staple base having a first rod-receiving recess coaxially aligned with a second rod-receiving recess, the first and second rod-receiving recesses dimensioned to receive an end portion of different spinal rod segments, a first blocking element hingedly attached to the staple base and moveable from a first position to a second position, the first position allowing placement of a spinal rod segment within the first rod-receiving recess, the second position covering the first rod-receiving recess while allowing placement of a different spinal rod segment within the second rod-receiving recess, a second blocking element having a first portion covering the second rod-receiving recess and a second portion covering at least a portion of the first blocking element, the second blocking element attachable to the staple base subsequent to the movement of the first blocking element from the first position to the second position, and an anchor element configured to anchor the anchor assembly to the second vertebral body;

introducing a first spinal rod segment such that the first end of the first spinal rod segment is placed within the second rod-receiving recess of the first anchor assembly and the second end of the first spinal rod segment is placed within the first rod-receiving recess of the second anchor assembly;

hingedly locking the first spinal rod segment to the second anchor assembly by moving the first blocking element on the second anchor assembly from the first position to the second position;

closing the first minimally invasive operative corridor;

establishing a second minimally invasive operative corridor to a second spinal target site, the second spinal target site comprising at least the portion of the lateral aspect of the second vertebral body having the implanted second anchor assembly and at least a portion of a lateral aspect of a third vertebral body, the second and third vertebral bodies being adjacent one another;

implanting a third anchor assembly in the lateral aspect of the third vertebral body, the third anchor assembly including a staple base having a first rod-receiving recess coaxially aligned with a second rod-receiving recess, the first and second rod-receiving recesses dimensioned to receive an end portion of different spinal rod segments, a first blocking element hingedly attached to the staple base and moveable from a first position to a second position, the first position allowing placement of a spinal rod segment within the first rod-receiving recess, the second position covering the first rod-receiving recess while allowing placement of a different spinal rod segment within the second rod-receiving recess, a second blocking element having a first portion covering the second rod-receiving recess and a second portion covering at least a portion of the first blocking element, the second blocking element attachable to the staple base subsequent to the movement of the first blocking element from the first position to the second position, and an anchor element configured to anchor the anchor assembly to the third vertebral body;

introducing a second spinal rod segment such that the first end of the second spinal rod segment is placed within the second rod-receiving recess of the second anchor assembly and the second end of the second spinal rod is placed within the first rod-receiving recess of the third anchor assembly;

hingedly locking the second spinal rod segment to the third anchor assembly by moving the first blocking element on the third anchor assembly from the first position to the second position; and closing the second minimally invasive operative corridor.

10. The method of claim 9, wherein at least one of the first, second, and third minimally invasive operative corridors is established using a lateral trans-psoas approach.

11. The method of claim 9, comprising the further steps of:

independently locking the first blocking element of the second anchor assembly to the second staple base using a setscrew; and independently locking the first blocking element of the third anchor assembly to the third staple base using a setscrew.

12. The method of claim 9, comprising the further step of:

locking the first spinal rod segment to the first staple base by attaching a second blocking element to the first anchor assembly; and locking the second spinal rod segment to the second staple base by attaching a second blocking element to the second anchor assembly.

\* \* \* \* \*